United States Patent
Makkouk et al.

(10) Patent No.: US 11,291,674 B2
(45) Date of Patent: Apr. 5, 2022

(54) ARGINASE INHIBITOR COMBINATION THERAPIES

(71) Applicant: CALITHERA BIOSCIENCES, INC., South San Francisco, CA (US)

(72) Inventors: Amani Makkouk, Mountain View, CA (US); Matthew I. Gross, Walnut Creek, CA (US); Francesco Parlati, San Francisco, CA (US)

(73) Assignee: CALITHERA BIOSCIENCES, INC., South San Francisco, CA (US)

( * ) Notice: Subject to any disclaimer, the term of this patent is extended or adjusted under 35 U.S.C. 154(b) by 256 days.

(21) Appl. No.: 15/807,357

(22) Filed: Nov. 8, 2017

(65) Prior Publication Data

US 2018/0161349 A1    Jun. 14, 2018

Related U.S. Application Data

(60) Provisional application No. 62/419,250, filed on Nov. 8, 2016, provisional application No. 62/559,931, filed on Sep. 18, 2017.

(51) Int. Cl.

| | |
|---|---|
| *A61K 31/69* | (2006.01) |
| *A61K 35/17* | (2015.01) |
| *A61P 35/00* | (2006.01) |
| *A61K 31/7076* | (2006.01) |
| *A61K 38/20* | (2006.01) |
| *A61K 31/4245* | (2006.01) |
| *A61K 31/675* | (2006.01) |

(Continued)

(52) U.S. Cl.
CPC .......... *A61K 31/69* (2013.01); *A61K 31/4245* (2013.01); *A61K 31/675* (2013.01); *A61K 31/7076* (2013.01); *A61K 35/17* (2013.01); *A61K 38/2013* (2013.01); *A61K 38/2086* (2013.01); *A61K 45/06* (2013.01); *A61P 35/00* (2018.01); *C12N 5/0638* (2013.01); *C12N 5/0646* (2013.01); *A61K 2300/00* (2013.01)

(58) Field of Classification Search
None
See application file for complete search history.

(56) References Cited

U.S. PATENT DOCUMENTS

| | | |
|---|---|---|
| 8,894,970 B2 | 11/2014 | Tomczuk et al. |
| 9,200,011 B2 | 12/2015 | Van Zandt et al. |
| 9,233,985 B2 | 1/2016 | Van Zandt et al. |

(Continued)

FOREIGN PATENT DOCUMENTS

| | | |
|---|---|---|
| CA | 2431080 A1 | 12/2004 |
| CN | 103068830 A | 4/2013 |

(Continued)

OTHER PUBLICATIONS

Lorvik et al., Cancer Research, vol. 76, No. 23, Sep. 12, 2016 (Sep. 12, 2016), pp. 6864-6876 (Year: 2016).*

(Continued)

*Primary Examiner* — Karl J Puttlitz
(74) *Attorney, Agent, or Firm* — Hugo Garrido; Carl Morales; Fenwick & West LLP

(57) ABSTRACT

The disclosure relates to methods of treating or preventing a disease in a subject by conjointly administering to the subject an arginase inhibitor disclosed herein and a composition comprising immune cells disclosed herein.

35 Claims, 25 Drawing Sheets

Figure 1A:
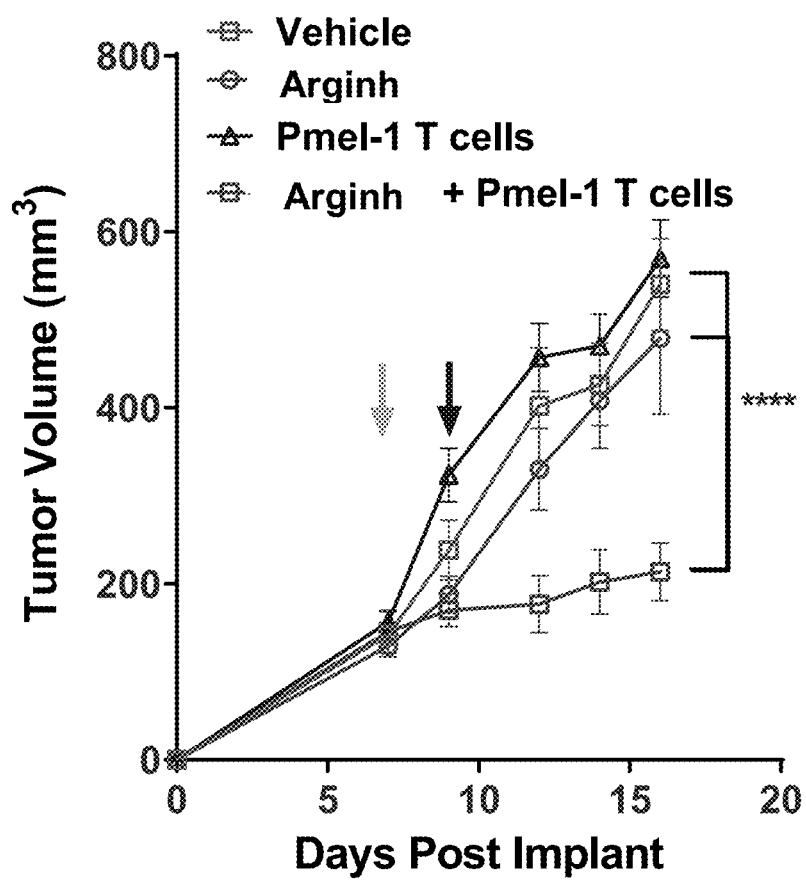

(51) Int. Cl.
A61K 45/06 (2006.01)
C12N 5/0783 (2010.01)

(56) References Cited

U.S. PATENT DOCUMENTS

| | | | |
|---|---|---|---|
| 9,266,908 | B2 | 2/2016 | Van Zandt et al. |
| 9,440,995 | B2 | 9/2016 | Van Zandt et al. |
| 2002/0081626 | A1 | 6/2002 | Kaddurah-Daouk et al. |
| 2004/0063666 | A1 | 1/2004 | Christianson et al. |
| 2010/0189644 | A1 | 7/2010 | Christianson et al. |
| 2012/0083469 | A1 | 4/2012 | Van Zandt et al. |
| 2012/0129806 | A1 | 5/2012 | Van Zandt et al. |
| 2014/0371175 | A1 | 12/2014 | Van Zandt et al. |
| 2015/0080341 | A1 | 3/2015 | Van Zandt et al. |
| 2015/0191492 | A1 | 7/2015 | Van Zandt et al. |
| 2016/0375044 | A1 | 12/2016 | Gross et al. |

FOREIGN PATENT DOCUMENTS

| | | | |
|---|---|---|---|
| CN | 103402549 A | | 11/2013 |
| CN | 105879030 A | | 8/2016 |
| WO | WO-1999019295 A1 | | 4/1999 |
| WO | WO-2007005620 A2 | | 1/2007 |
| WO | WO-2010085797 A2 | | 7/2010 |
| WO | WO-2011133653 A1 | | 10/2011 |
| WO | WO-2012058065 A1 | | 5/2012 |
| WO | WO-2012091757 A1 | | 7/2012 |
| WO | WO-2013059437 A1 | | 4/2013 |
| WO | WO-2013059587 A1 | | 4/2013 |
| WO | WO-2013158262 A1 | | 10/2013 |
| WO | WO-2015061752 A1 | | 4/2015 |
| WO | WO-2016153078 A1 | | 9/2016 |
| WO | WO-2016210106 A1 | | 12/2016 |
| WO | 2017075363 | * | 5/2017 |

OTHER PUBLICATIONS

Rossnagl et al., PLOS Biology, vol. 14, No. 9, Sep. 21, 2016 (Sep. 21, 2016) (Year: 2016).*
Geiger et al., Cell, Cell Press, vol. 167, No. 3, Oct. 13, 2016 (Year: 2016).*
Rosenberg et al., Science Apr. 3, 2015; 348(6230): 62-68 (Year: 2015).*
Monette et al., Biomaterials, vol. 75, p. 237-249 (Year: 2015).*
Pardoll, Nat Rev Cancer Mar. 22, 2012;12(4):252-64 (Year: 2012).*
Bender et al., Oncol Res Treat 2016;39:369-376 (Year: 2016).*
Eggermont et al., Trends in Biotechnology, Sep. 2014, vol. 32, No. 9, 456-465 (Year: 2014).*
Ajinomoto Amino Acids Link News Aug. 2005 vol. 11: 3-4.
Arina, A. et al. 2014 "Adoptively Transferred Immune T Cells Eradicate Established Tumors despite Cancer-Induced Immune Suppression," *J Immunol* 192: 1286-1293.
Baggio et al. 1997 "Inhibition of Mn2+ 2-Arginase by Borate Leads to the Design of a Transition State Analogue Inhibitor, 2(S)-Amino-6-boronohexanoic Acid," *J Am Chem Soc* 119(34): 8107-8108.
Barbul, A. 1990 "Arginine and Immune Function," Nutrition 6(1) 53-58.
Bartolucci et al. 2012 "Direct, Regioselective and Chemoselective Preparation of Novel Boronated Tryptophans by Friedel-Crafts Alkylation" *Organic Letters* 14(2): 600-603.
Busnel et al. 2005 "Synthesis and evaluation of new co-borono-a-amino acids as rat liver arginase inhibitors," *Bioorg Med Chem* 13(7): 2373-2379.
Calithera Biosciences, Inc. Poster, SITC Conference; Nov. 9-13, 2016; National Harbor, MD.
Calithera Biosciences, Inc. Poster, EORTC-NCI-AACR; Nov. 29-Dec. 2, 2016; Munich, Germany.
CAS Registry No. 1374395-07-9. CA Index Name: "3-Pyrrolidinecarboxylic acid, 3-amino-4-(3-boronopropyl)-14(5,7-dichloro-1, 2,3,4-tetrahydro-3-isoquinolinyl)carbonyll-, (3R,4S)-rel-". STN Entry Date: May 24, 2012 (Last update: May 28, 2012).

Colleluori et al. 2001 "Classical and Slow-Binding Inhibitors of Human Type II Arginase," *Biochem*, 40(31): 9356-9362.
Curtis, B. et al. 2013 "Secondary amines containing one aromatic nitro group: preparation, nitrosation, sustained nitric oxide release, and the synergistic effects of released nitric oxide and an arginase inhibitor on vascular smooth muscle cell proliferation," *Bioorganic & medicinal chemistry* 21(5) 1123-1135. Retrieved from: <https://www.ncbi.nlm.nih.gov/pmc/articles/PMC3574223/pdf/nihms434525.pdf>.
Ellyard et al. 2010 "Alternatively Activated Macrophage Possess Antitumor Cytotoxicity That Is Induced by IL-4 and Mediated by Arginase-1," *J Immunother* 33: 443-452.
Geiger, Roger et al. 2016 "L-Arginine Modulates T Cell Metabolism and Enhances Survival and Anti-tumor Activity," *Cell, Cell Press* 167(3): 829ff.
Gritli-Linde, A. et al. 1998 "Opposing effects of suramin and DL-alpha-difluoromethylornithine on polyamine metabolism contribute to a synergistic action on B16 melanoma cell growth in vitro," *Anticancer Research* 18(2A) 863-870.
Hörig et al. 2004 "From bench to clinic and back: Perspective on the 1st IQPC Translational Research conference," J *Translational Med*, 2:44 doi:10.1186/1479-5876-2-44.
Ilies et al. 2011 "Binding of alpha,alpha-Disubstituted Amino Acids to Arginase Suggests New Avenues for Inhibitor Design," *J Med Chem* 54(15): 5432-5443.
International Search Report and Written Opinion for International Application No. PCT/US2017/060636 dated Mar. 22, 2018.
Ivanenkov et al. 2014 "Small-molecule arginase inhibitors," *Pharm Pat Anal* 3(1): 65-85.
Kabalka et al. 2008 "Synthesis of a series of boronated unnatural cyclic amino acids as potential boron neutron capture therapy agents," *Appl Organomet Chem*, 22(9): 516-522.
Koziara et al. 2004 "Paclitaxel nanoopartides for the potential treatment of brain tumors," *J Controlled Release* 99: 259-269.
Lei et al. 2009 "Progress of Boronic Acids as Enzyme Inhibitors" *Chinese J Pharm* 40(3): 213-219 (English Abstract only).
Li, L. et al. "An Engineered Arginase FC Protein Inhibits Tumor Growth In Vitro and In Vivo," *Evidence-Based Complementary and Alternative Medicine* vol. 2013, Article ID 243129: 1-9.
Lorvik, Kristina Berg et al. 2016 "Adoptive Transfer of Tumor-Specific Th2Cells Eradicates Tumors by Triggering an in Situ Inflammatory Immune Response," *Cancer Research* 76(23): 6864-6876.
Raber, P. et al. 2012 Metabolism of L-Arginine by Myeloid-Derived Suppressor Cells in Cancer: Mechanisms of T cell suppression and Therapeutic Perspectives *Immunol Invest* 41(6-7): 614-634.
Raber, P. et al. 2016 "T cells conditioned with MDSC show an increased anti-tumor activity after adoptive T cell base immunotherapy," *Oncotarget* 7(14): 17565-17578.
Rodriguez, P. et al. 2003 "L-Arginine Consumption by Macrophages Modulates the Expression of CDχ Chain in T Lymphocytes," *J Immunol* 17: 1232-1239.
Rodriguez, P. et al. 2004 "Arginase I Production in the Tumor Microenvironment by Mature Myeloid Cells Inhibits T-Cell Receptor Expression and Antigen-Specific T-Cell Responses," *Cancer Research* 64: 5839-5849.
Rodriguez, P. et al. 2008 "Arginine regulation by myeloid derived suppressor cells and tolerance in cancer: mechanisms and therapeutic perspectives," *Immunol Rev* 222: 180-191.
Rossnagl, Stephanie et al. 2016, "EDA-Fibronectin Originating from Osteoblasts Inhibits the Immune Response against Cancer," *PLOS Biology* 14(9): e1002562.
Sandgren, S. and Belting, M. 2003 "Suramin Selectively inhibits carcinoma cell growth that is dependent on extracellular polyamines," *Anticancer Research* 23(2B): 1223-1228.
Schafer, et al. 2008 "Failure is an option: learning from unsuccessful proof-of-concept trials," *DrugDiscov Today*, 13(21): 913-916.
Scheit, K. and Bauer, G. 2014 "Synergistic effects between catalase inhibitors and modulators of nitric oxide metabolism on tumor cell apoptosis," *Anticancer Research* 34(10): 5337-5350. Retrieved from: <https://ar.iiarj ournals.org/content/34/10/5337.full.pdf+html>.

(56) References Cited

OTHER PUBLICATIONS

Segal et al. 2012 "Chronic Oral Administration of the Arginase Inhibitors 2(S)-amino-6-boronohexanoic Acid (ABH) Improves Erectile Function in Aged Rates," *J Androl*, 33(6): 11691175.

Selamnia, M. et al. 1998 "α-Difluoromethylornithine (DFMO) as a potent arginase activity inhibitor in human colon carcinoma cells," *Biochemical pharmacology* 55(8): 1241-1245.

Singh, S. et al. 2000 "Arginase Activity in Human Breast Cancer Cell Lines: $N^\omega$-Hydroxy-L-arginine Selectively Inhibits Cell Proliferation and Induces Apoptosis in MDA-MB-468 Cells" *Cancer Research* 60: 3305-3312.

Steggerda, SusanneM et al. 2016 "Abstract B045: Arginase inhibitor CB-1158 elicits immune-mediated antitumor responses as a single agent and in combination with other immunotherapies," Second CRI-CIMT-EATI-AACR International Cancer Immunotherapy Conference: Translating Science into Survival; Sep. 25-28, 2016; New York, NY.

Steggerda, SusanneM. et al. 2017, "Inhibition of arginase by CB-1158 blocks myeloid cell-mediated immune suppression in the tumor microenvironment," *Journal for ImmunoTherapy of Cancer* 5(1): 1-18.

Steppan et al. 2013 "Development of novel arginase inhibitors for therapy of endothelial dysfunction," *Front Immunol* 51(4): 5905-5908.

Tate et al. 2008 "Effect of arginase II on L-arginine depletion and cell growth in murine cell lines of renal cell carcinoma," *J Hematol Oncol* 1(14): 1-10.

Vissers, Y. et al. 2005 "Plasma arginine concentrations are reduced in cancer patients: evidence for arginine deficiency?" *Am J Clin Nutr* 81: 1142-1146.

Nishimura et al., "Cancer Immunotherapy," Journal of Japan Society of Immunology & Allergology in Otolaryngology, 2013;31(4):237-246.

Oberlies et al., "Regulation of NK Cell Function by Human Granulocyte Arginase," J Immunol. 2009;182:5259-5267.

\* cited by examiner

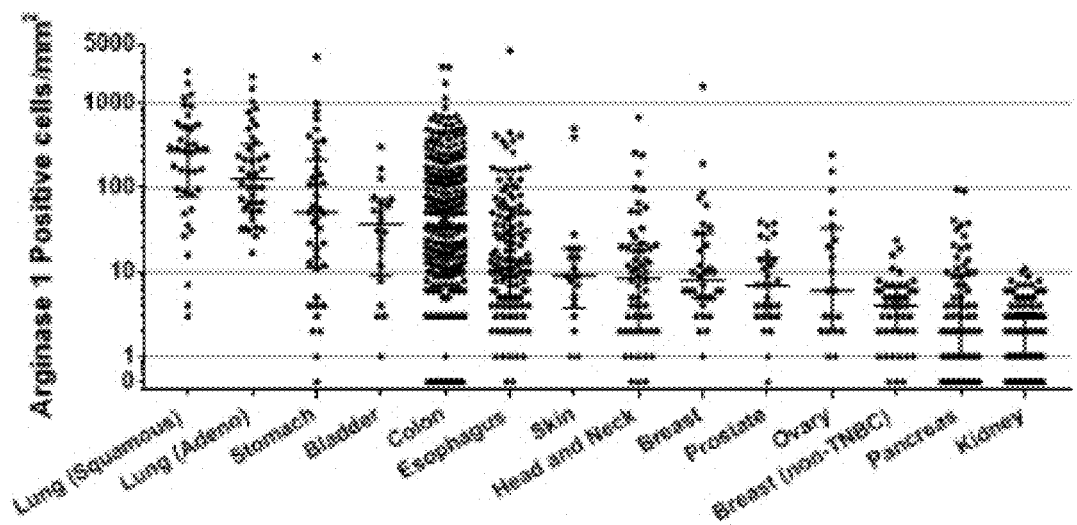
FIG. 8A
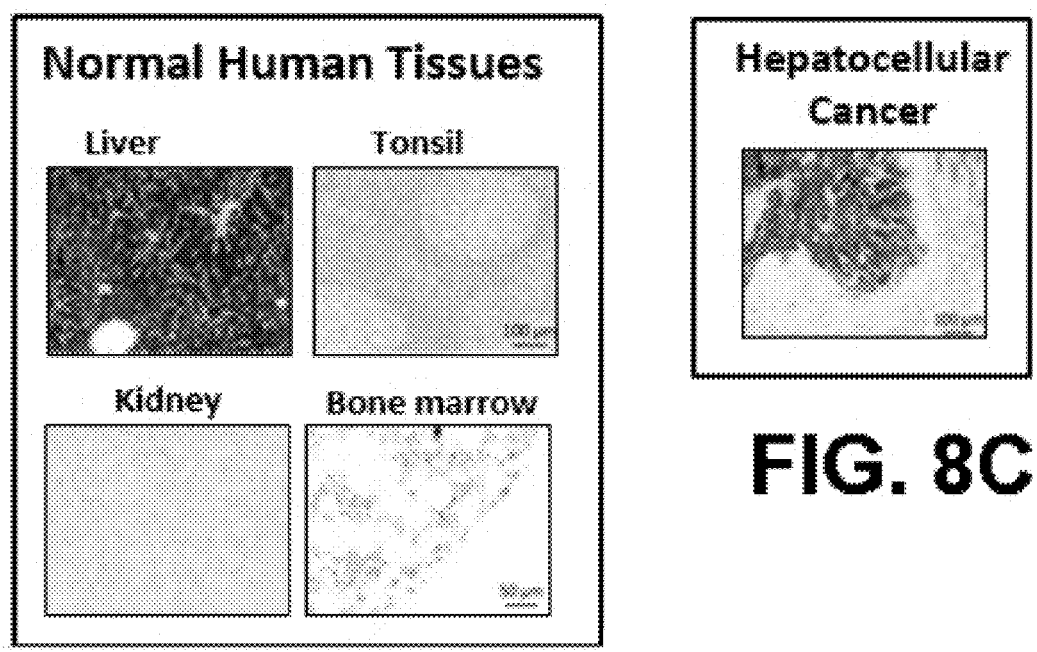
FIG. 8B
FIG. 8C

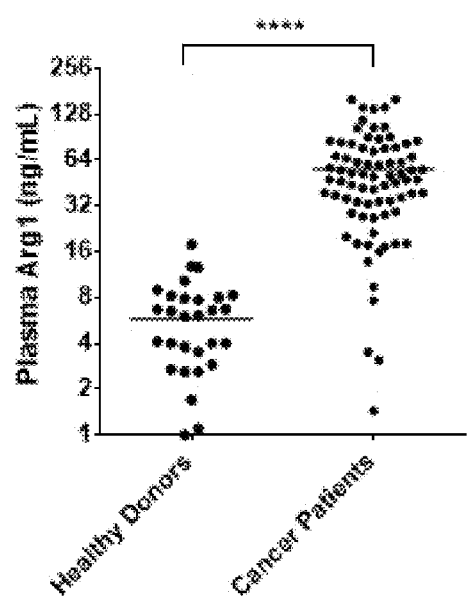
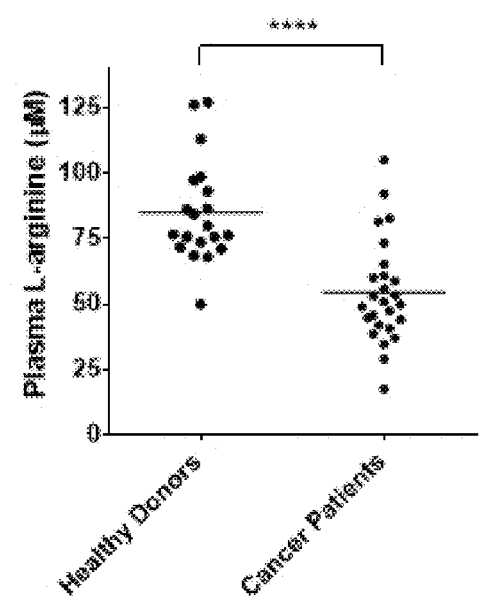
FIG. 8G  FIG. 8H

ARGINASE INHIBITOR COMBINATION THERAPIES

1. BACKGROUND

Adoptive cell transfer of immune cells, or adoptive immunotherapy, is a cell therapy that involves the removal of immune cells from a subject, the ex-vivo processing (i.e., activation, purification and/or expansion) of the immune cells, and the subsequent infusion of the resulting cells back into the same or different subject.

Adoptive immunotherapy treatments can have unpredictable and sporadic efficacy, and the reasons for the unpredictable and sporadic efficacy of these treatments are not clearly understood. Moreover, adoptive immunotherapy has had limited application in treating cancer owing to the accumulation of myeloid-derived suppressor cells (MDSCs) in the tumor microenvironment. The mechanistic rationale for MDSCs inhibiting the efficacy of adoptive immunotherapy has not been determined. While it is known that MDSCs produce arginase in tumor microenvironments, thereby reducing the amount of arginine in the tumor microenvironments, the role of arginine in the adoptive immunotherapy has not been established. Early studies suggested that arginine can potentially inhibit adoptive T-cell immunotherapy through several different mechanisms (see, e.g., Raber i., *Oncotarget*, 7, 17565-17578; Lorvik et al. 2016, *Cancer Res.*, 76, 6864-6876; Ellyard et al. 2010, *J Immunother.* 33, 443-452). For instance, Lorvik et al. and Ellyard et al. postulated that arginase is important in ensuring particular macrophages are cytotoxic towards cancer cells, thus inhibiting their proliferation.

Therefore, there is a need to improve the efficiency of adoptive immunotherapy treatments.

2. SUMMARY

The present application discloses that arginine can have a detrimental effect on adoptive immunotherapy. Furthermore, the present application discloses that arginase inhibition in the tumor or tumor microenvironment can enhance the efficacy of adoptive immunotherapy. In fact, as set forth in the examples below, the present application discloses that adoptive immunotherapy synergizes with arginase inhibition, thereby providing an effective method of treating cancer.

Accordingly, the present disclosure provides methods of enhancing the efficacy of an adoptive cell transfer by co-administering an arginase inhibitor with the adoptive immunotherapy to a subject (e.g., human). The arginase inhibitor can be administered conjointly (e.g., administered sequentially or simultaneously) with the adoptive immunotherapy. For instance, an arginase inhibitor is administered conjointly with an adoptive T-cell immunotherapy or an adoptive NK cell immunotherapy to enhance the efficacy of the adoptive T-cell or NK cell immunotherapy. In some embodiments, the adoptive T-cell immunotherapy involves transfer of cytotoxic T cells (CTLs) such as CD8+ T cells to the subject. In some embodiments, the adoptive T-cell immunotherapy involves transfer of both CD4+ T cells to the subject. In some embodiments, the adoptive T-cell immunotherapy involves transfer of both CD8+ T cells and CD4+ T cells to the subject. In some embodiments, the adoptive immunotherapy involves transfer of both T cells and NK cells to the subject.

In particular embodiments, the arginase inhibitor enhances the efficacy of the adoptive immunotherapy when administered to a subject (e.g., human) with cancer. In some such embodiments, the cancer is melanoma. In other embodiments, the cancer is multiple myeloma. In other embodiments, the cancer is lung cancer. In other embodiments, the cancer is breast cancer. The adoptive immunotherapy and the arginase inhibitor may be administered with one or more cytokines (e.g., IL-2 or IL-5).

Provided herein are compositions and methods related to treating or preventing a disease (e.g., cancer or a viral infection) in a subject by administering to the subject a combination therapy. In some embodiments, the combination therapy comprises conjointly administering an arginase inhibitor (e.g., an arginase inhibitor of any one of the formulae disclosed herein) and an adoptive cell transfer. In some embodiments, the adoptive cell transfer involves transferring immune cells (e.g., T cells, such as cytotoxic T cells (CTLs), or natural killer (NK) cells, such as NK-92 cells) to a subject with a disease (e.g., cancer or a viral infection). In some embodiments, the immune cells express chimeric antigen receptors. In some embodiments, the immune cells express a receptor specific for a disease-associated peptide. The immune cells may be autologous (i.e., from the subject) or allogenic (i.e., from a donor or from a cell bank).

Such immune cells (e.g., T cells, such as CTLs) may be expanded in the presence of antigen presenting cells (APCs) that present one or more disease-specific peptide(s) prior to administration to the subject. The APCs may be B cells, dendritic cells, or artificial antigen-presenting T-cells (aK562 T cells). In some embodiments, the immune cells are not enriched. In some embodiments, the composition comprising immune cells and arginase inhibitor are conjointly administered (e.g., administered sequentially or simultaneously). The composition comprising immune cells may further comprise one or more cytokines (e.g., IL-2 or IL-15). In some embodiments, about $1 \times 10^6$ cells/kg cells to about $1 \times 10^9$ cells/kg cells are administered to the subject.

In some embodiments, of the combination therapy comprises conjointly administering to the subject an arginase inhibitor (e.g., an arginase inhibitor with a formula disclosed herein), a composition comprising immune cells (e.g., a composition of immune cells described herein), and an antibody (e.g., an antibody that targets tumor cells). The antibody may be a monoclonal, polyclonal, or a chimeric antibody. The arginase inhibitor, composition comprising immune cells, and the antibody may be administered together or a different times (e.g., sequentially).

The adoptive immunotherapy and the arginase inhibitor may be administered with other chemotherapeutic agents. In one embodiment, a combination of an adoptive immunotherapy, an arginase inhibitor and a standard-of-care chemotherapeutic agent are administered to a subject (e.g., human patient) with cancer to enhance the therapeutic activity of the adoptive immunotherapy. In one such embodiment, the standard-of-care chemotherapeutic agent is gemcitabine. In another such embodiment, the chemotherapeutic agent is cyclophosphamide. In another such embodiment, the chemotherapeutic reagent is fludarabine. The chemotherapeutic reagent(s) can be administered prior to, after and/or concurrently with the adoptive immunotherapy/arginase inhibitor. In all of these embodiments, the adoptive immunotherapy and the arginase inhibitor may be administered with one or more cytokines (e.g., IL-2 or IL-5).

The adoptive immunotherapy and the arginase inhibitor may be administered with one or more immune-modulating agents. For instance, the adoptive immunotherapy and the arginase inhibitor may be administered with an immune checkpoint inhibitor such as a PD-1 inhibitor, PD-L1 inhibitor or a CTLA-4 inhibitor to enhance the efficacy of the adoptive immunotherapy. In such embodiments, the checkpoint inhibitor can be administered prior to, after and/or concurrently with the adoptive immunotherapy/arginase inhibitor. In all of these embodiments, the adoptive immunotherapy and the arginase inhibitor may be administered with one or more cytokines (e.g., IL-2 or IL-5).

The adoptive immunotherapy and the arginase inhibitor may be administered with one or more inhibitors of the enzyme IDO-1. In certain such embodiments, the IDO-1 inhibitor is epacadostat.

In some embodiments, the arginase inhibitor administered to the subject (e.g., human patient) conjointly with the adoptive immunotherapy does not substantially penetrate into cells but rather preferentially stays in the plasma or the microenvironment surrounding the tumor or the tumor itself. For instance, the arginase inhibitor may have a greater affinity for soluble arginases than for intracellular arginases. Such arginase inhibitors may improve the efficacy of the adoptive immunotherapy without toxicological concerns often associated with arginine supplementation in cells. In some embodiments, the arginase inhibitor has an $IC_{50}$ value of intracellular arginase in hepatic cell lines (e.g., HepG2) or K562 cell lines that is at least two, three, or four orders of magnitude higher than for soluble arginases in cell lysates.

In some embodiments, the arginase inhibitor administered in combination with the adoptive immunotherapy has the structure of Formula I, II, III, IVa, IVb, V, or VI as described below. In some embodiments, the arginase inhibitor administered in combination with the adoptive immunotherapy has the structure of Formula VIa, VIb, VIc, VId, VIe, VIf, VIg, or VIh, as described below.

In some embodiments, the arginase inhibitor administered in combination with the adoptive immunotherapy has the following structure, or a pharmaceutically acceptable salt thereof:

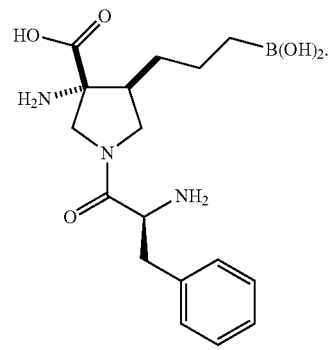

In some embodiments, the arginase inhibitor administered in combination with the adoptive immunotherapy has the following structure, or a pharmaceutically acceptable salt thereof:

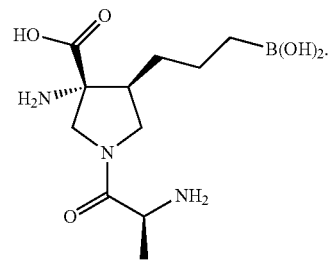

The compound and pharmaceutically acceptable salts thereof are disclosed in WO 2017/075363 (see compounds 10 and 13).

In some embodiments, the arginase inhibitor administered in combination with the adoptive immunotherapy has the following structure, or a pharmaceutically acceptable salt thereof:

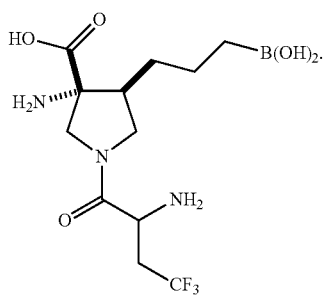 [SMILES: NC(CC(F)(F)F)C(=O)N1C[C@H](CCCB(O)O)[C@](N)(C(=O)O)C1]

In some embodiments, the arginase inhibitor administered in combination with the adoptive immunotherapy has the following structure, or a pharmaceutically acceptable salt thereof:

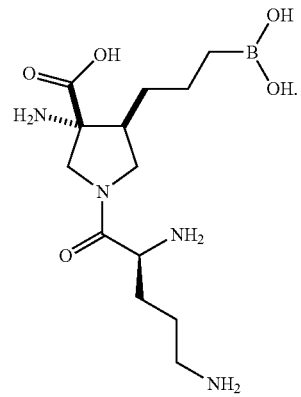 [SMILES: NCCC[C@H](N)C(=O)N1C[C@H](CCCB(O)O)[C@](N)(C(=O)O)C1]

In some embodiments, the arginase inhibitor administered in combination with the adoptive immunotherapy has the following structure, or a pharmaceutically acceptable salt thereof:

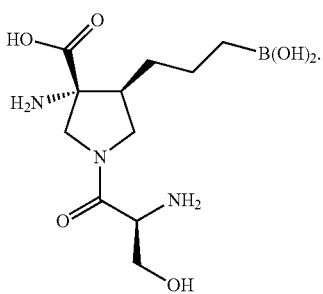 [SMILES: N[C@@H](CO)C(=O)N1C[C@H](CCCB(O)O)[C@](N)(C(=O)O)C1]

In some embodiments, the arginase inhibitor administered in combination with the adoptive immunotherapy has the following structure, or a pharmaceutically acceptable salt thereof:

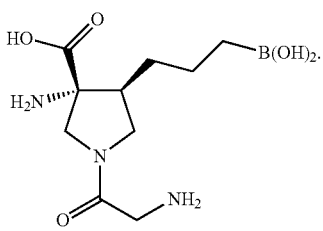 [SMILES: NCC(=O)N1C[C@H](CCCB(O)O)[C@](N)(C(=O)O)C1]

3. BRIEF DESCRIPTION OF THE FIGURES

Figure 1B:
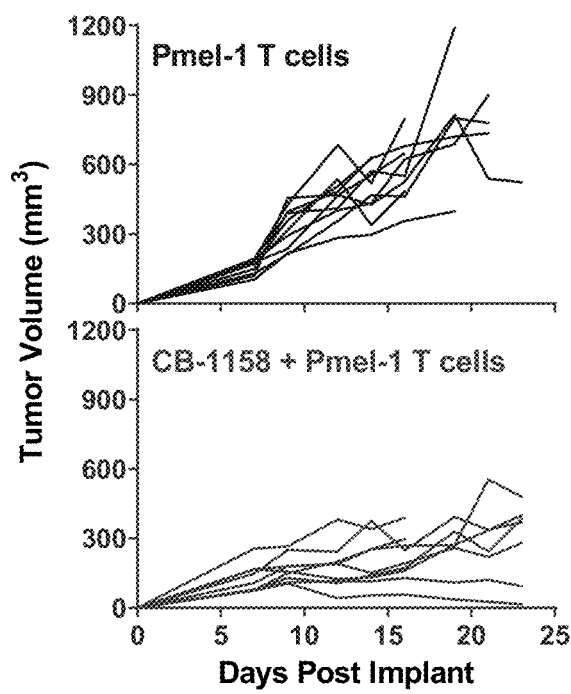
Figure 1C:
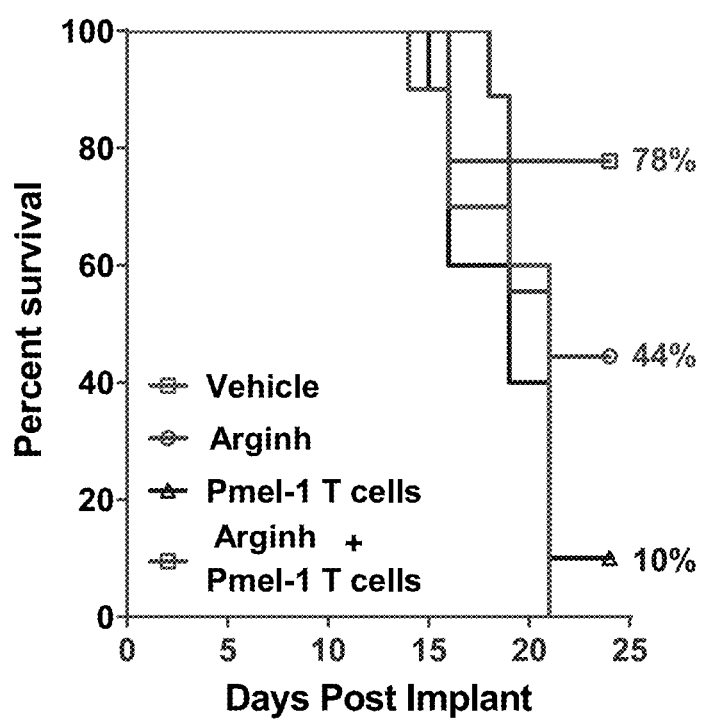

FIGS. 1A-1C show that an arginase inhibitor synergizes with adoptively transferred antigen-specific T cells to inhibit tumor growth;

FIGS. 2A-2G show inhibition of arginase reverses myeloid cell-mediated suppression of in vitro T cell proliferation. (FIG. 2A) T cells (left) and NK cells (right) require extracellular L-arginine for proliferation. CFSE-loaded T cells or NK cells were stimulated with anti-CD3/anti-CD28 or IL-2, respectively, in media either containing or lacking L-arginine. Proliferation was measured after 72 h by flow cytometry. (FIG. 2B) Isolated human granulocytes deplete L-arginine from the media, measured after 48 h by LC/MS. (FIG. 2C) Human peripheral blood T cells are suppressed from proliferating by co-culture with granulocytes isolated from the same healthy donor. (FIG. 2D) left, arginase inhibitor inhibits the consumption of arginine from the media by granulocytes in a dose-dependent manner; right, arginase inhibitor inhibits granulocyte-mediated suppression of T-cell proliferation in a dose-dependent manner. The ratio of granulocytes to T cells in the co-cultures was 0.25 to 1. (FIG. 2E) arginase inhibitor reverses T cell suppression conferred by granulocytic MDSCs. Media conditioned by granulocytic-MDSCs purified from a lung cancer patient's blood inhibited T-cell proliferation and is depleted of L-arginine, and both effects are reversed in a dose-dependent manner by arginase inhibitor. Left, arginine amounts in the media; right, T-cell proliferation. The ratio of MDSCs conditioning the media to T cells was 1 to 1. (FIG. 2F), Conditioned media from purified granulocytes isolated from a head and neck cancer patient's blood inhibited T-cell proliferation and are depleted of L-arginine, and both effects are reversed in a dose-dependent manner by arginase inhibitor. Left, T-cell proliferation; right, arginine amounts in the media. The ratio of granulocytes conditioning the media to T cells was 0.5 to 1. (FIG. 2G) arginase inhibitor reverses the inhibition of secretion of interferon-γ and granzyme-B conferred by cancer patient granulocytes. Media from panel (FIG. 2F) were analyzed by Cytometric Bead Array.

Figure 3A:
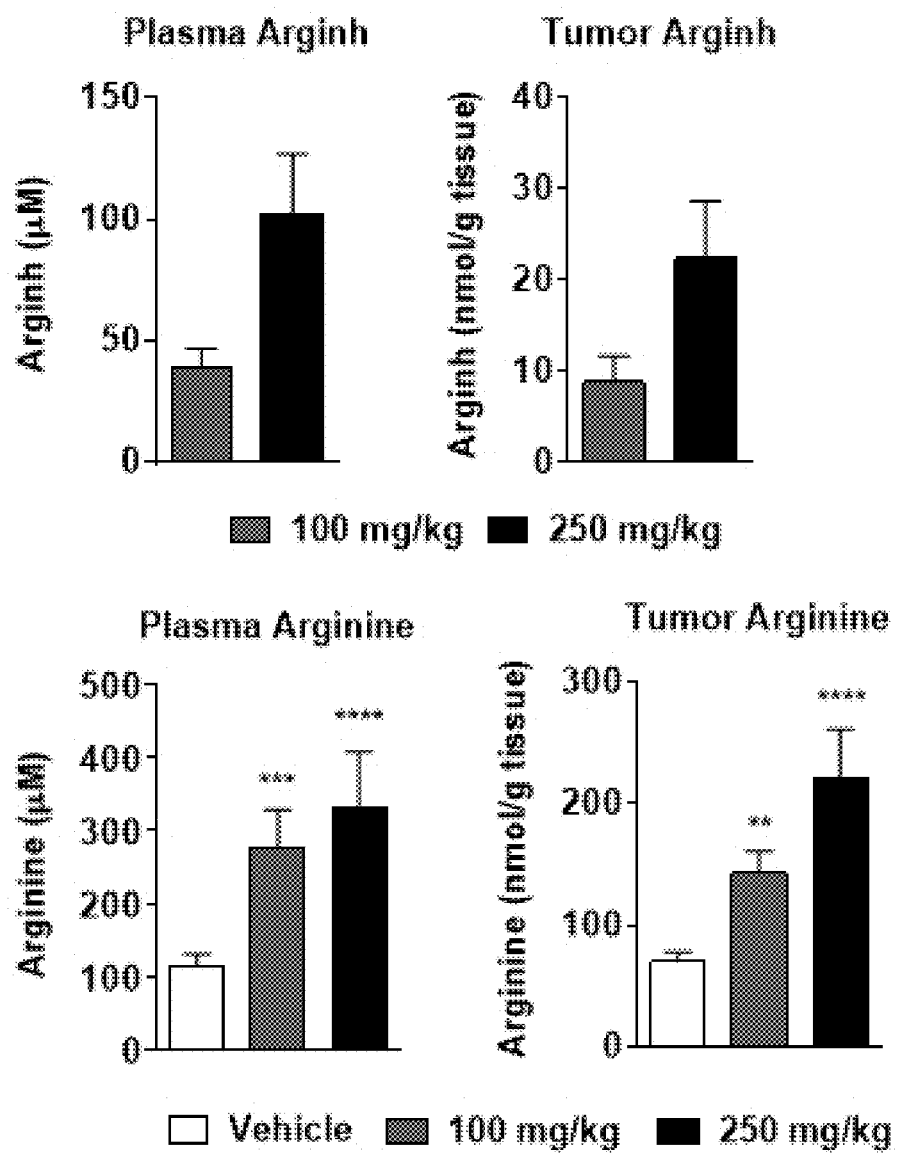
Figure 3B:
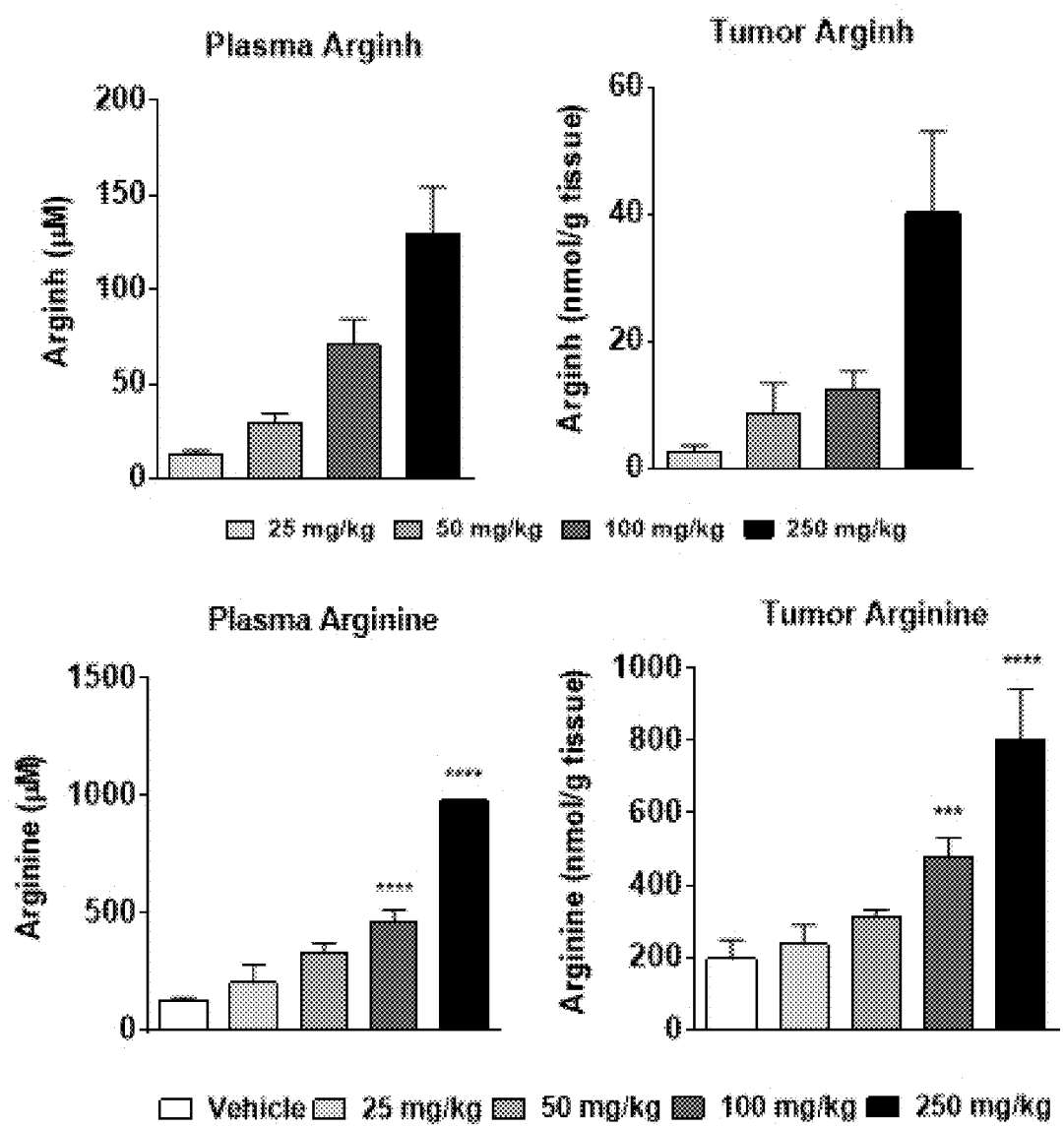
Figure 3C:
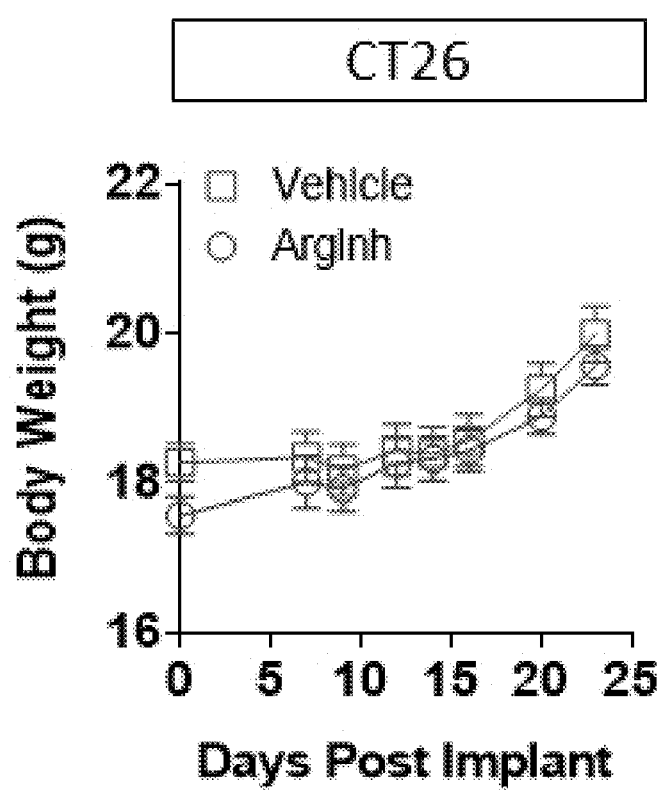

FIGS. 3A-3C show the arginase inhibitor has favorable pharmacokinetic and pharmacodynamic properties in vivo with no overt signs of toxicity. LLC tumor-bearing mice (N=5 per group) were administered a single dose of arginase inhibitor (FIG. 3A) or 5 twice-daily doses (FIG. 3B) and samples were collected 2 h after the last dose. Arginase inhibitor (FIGS. 3A and 3B, top rows) and L-arginine (FIGS. 3C and 3B, bottom rows) in plasma and tumor lysates were measured by LC/MS. (FIG. 3C) Body weights of mice inoculated with CT26 cells and dosed with vehicle or arginase inhibitor twice daily for 23 days. (**$P<0.0001$; *$P<0.001$; **$P<0.01$ vs. vehicle).

Figure 4A:
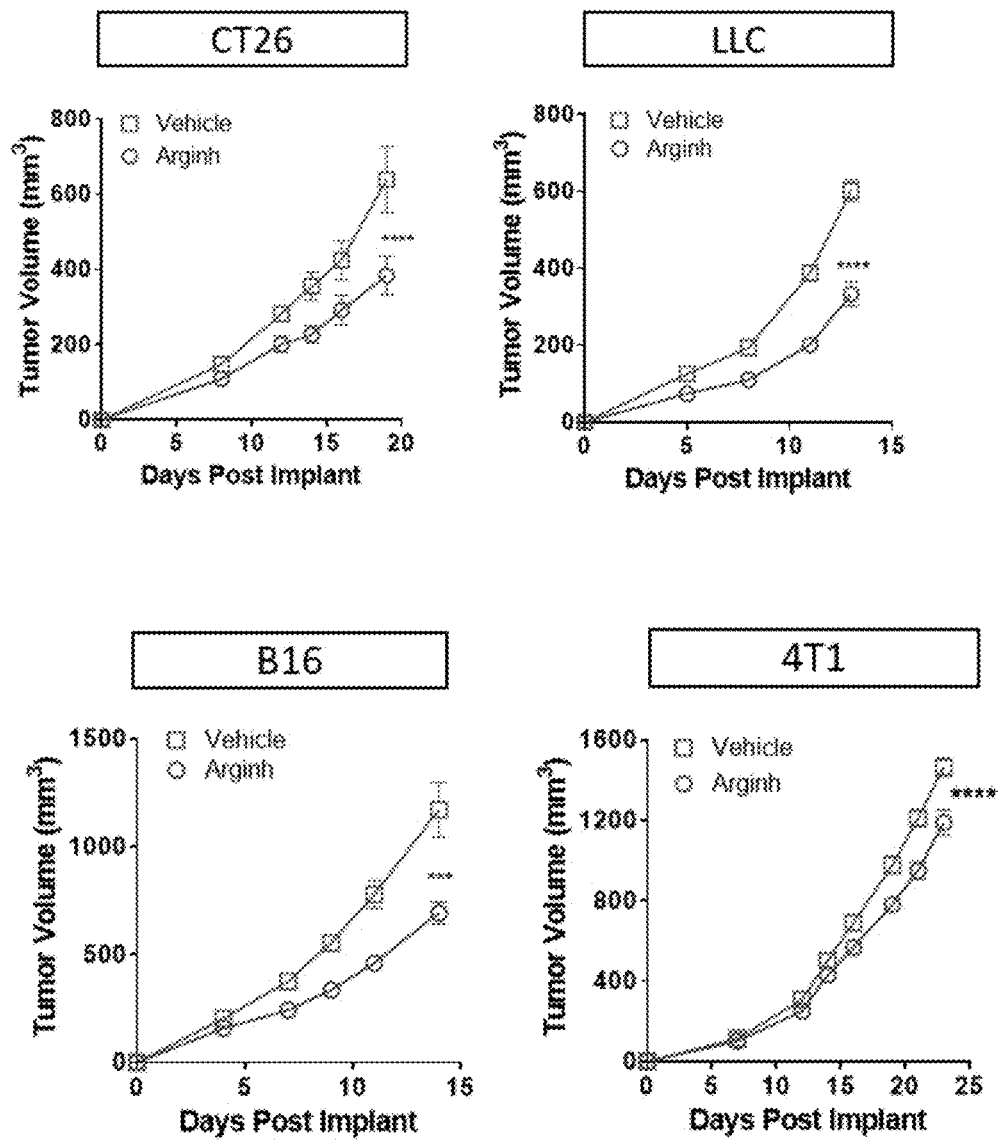
Figure 4B:
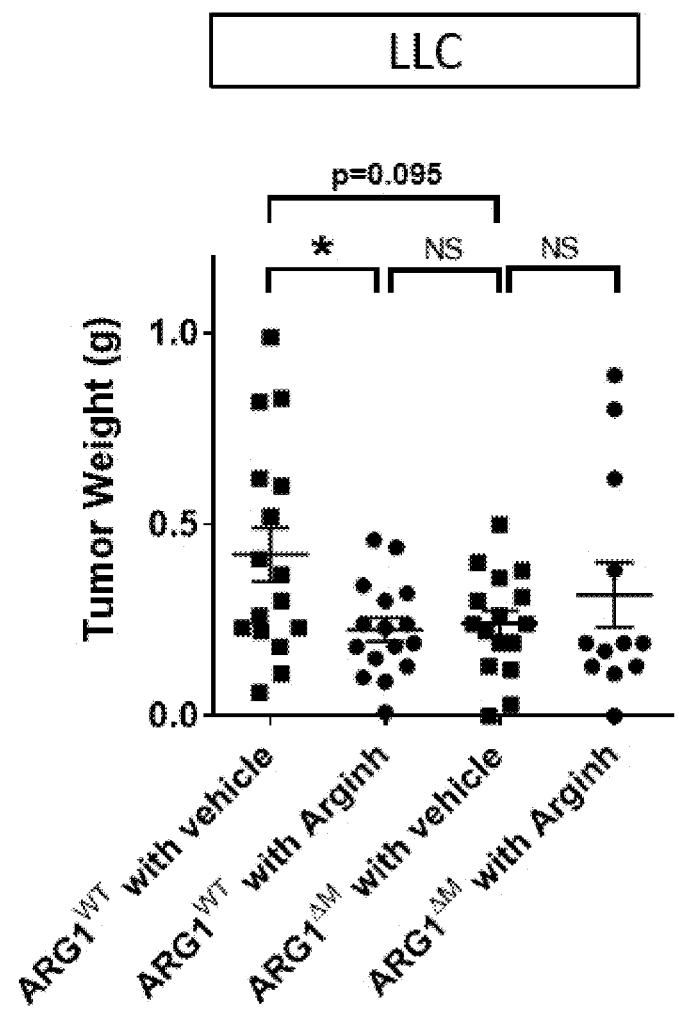

FIGS. 4A-4B show arginase inhibition reduces tumor growth in vivo. (FIG. 4A) Arginase inhibitor, dosed at 100 mg/kg BID, reduced tumor growth as a single agent in multiple syngeneic mouse models of cancer (N=10 per group). (FIG. 4B) Mice lacking Arg1 gene expression in the myeloid compartment (referred to as ARG1$^{\Delta M}$) grow smaller tumors than mice containing wild-type Arg1 (ARG1$^{WT}$), and treatment of ARG1$^{\Delta M}$ mice with arginase inhibitor does not further reduce tumor growth, indicating on-target activity of arginase inhibitor (N=16 per group). (T test: ****$P<0.0001$; *$P<0.05$).

FIGS. 5A-5E show the arginase inhibitor requires an intact immune system for efficacy. (FIG. 5A) CellTiterGlo assays (72 h) were performed on the indicated cell lines with a dose-titration of arginase inhibitor. (FIG. 5B) B6.CB17-Prkdc (SCID)/SzJ mice were implanted with LLC cells and arginase inhibitor was dosed 100 mg/kg PO twice daily. (FIGS. 5C-5E) Tumor growth inhibition by arginase inhibitor in the B16 (FIG. 5C), CT26 (FIG. 5D), and LLC (FIG. 5E) models is mediated by CD8$^+$ and NK cells. Tumor-bearing mice were treated with depleting antibodies and dosed twice-daily with vehicle or 100 mg/kg arginase inhibitor. Tumors from LLC studies were analyzed on study day 13 (CD8$^+$ cell depletion) or study day 14 (NK cell depletion). (**$P<0.0001$; *$P<0.001$; **$P<0.01$).

FIGS. 6A-6F show arginase inhibitor-treated animals have increased tumor-infiltrating cytotoxic cells and decreased myeloid cells. (FIG. 6A) CT26 tumors from animals treated with arginase inhibitor had increased CD8+ CD25+ T-cells compared to vehicle-treated animals on study day 14 (N=10 per group). (FIG. 6B) In the B16F10 model, arginase inhibitor treatment resulted in an increase in CD25+ CD8+ T-cells observed on study day 9 (N=10 per group). (FIG. 6C) In the LLC model, arginase inhibitor treatment resulted in increased tumor infiltrating CD8+ T-cells and decreased CD68+ myeloid cells observed on study day 14 (N=10 per group). (FIG. 6D) In the 4T1 model, arginase inhibitor treatment resulted in increases in both T-cells and NK-cells and a decrease in myeloid cells observed on study day 10 (N=10 per group). (FIG. 6E) Arginase inhibitor increases T-cell and NK-cell markers and interferon response genes. mRNA transcripts in LLC tumors from mice treated with vehicle or 100 mg/kg BID arginase inhibitor were determined by Nanostring (N=6 per group). (FIG. 6F) Cytokines and chemokines in LLC tumors from mice treated with vehicle or 200 mg/kg BID arginase inhibitor were determined by Luminex (N=5 per group) (T test: **$P<0.01$; *$P<0.05$).

FIGS. 7A-7D show the arginase inhibitor combines with immunotherapy, chemotherapy, or cell transfer to inhibit tumor growth. (FIG. 7A) Arginase inhibitor in combination with PD-L-1 blockade inhibited tumor growth in the CT26 model. Growth curves (left and center) and survival curves (right) are shown. N=10 per group. (FIG. 7B) Arginase inhibitor in combination with gemcitabine in the CT26 model (left) or the LLC model (right) inhibited tumor growth. N=10 per group. (FIG. 7C) Arginase inhibitor and adoptive T cell transfer inhibited tumor growth in the B16-F10 model. Non-myeloablative chemotherapy regimen of cyclophosphamide plus fludarabine (C/F) was administered to all groups, and IL-2 was dosed to groups receiving T cells. On study day 9, Pmel-1 T cells were transferred to mice in the T cell groups (ACT). N=10 per group. (FIG. 7D) Arginase inhibitor and adoptive NK cell transfer reduced lung metastases in the CT26 model. N=6 control; N=7 arginase inhibitor; N=5 NK cells; N=5 arginase inhibitor+ NK cells (T test: **$P<0.0001$; *$P<0.001$; **$P<0.01$; *$P<0.05$).

FIGS. 8A-8H show arginase 1 is abundant in multiple types of cancer. (FIG. 8A) Immunohistochemistry of human tumor tissue microarrays stained with an anti-arginase 1 antibody were quantified for arginase 1-positive infiltrating granulocytes by digital histopathology. (FIGS. 8B-8D) Immunohistochemistry staining for Arg1 in sections of normal human tissues (N=33 tissues analyzed) and human tumor tissues (N=12 tumor histologies analyzed). Representative images are shown. Arrows point to arginase-expressing myeloid cells. (FIG. 8E) Percentage of arginase 1-positive cells that co-express the granulocyte marker, CD15, or macrophage marker, CD68, in tumor tissue microarrays as determined by quantitation of MultiOmyx immunofluorescence. (FIG. 8F) Immunofluorescent staining (MultiOmyx) of a tumor section from a patient with head & neck cancer shows numerous arginase 1-positive granulocytes. (FIG. 8G) Plasma arginase 1 protein determined by ELISA from cancer patients (N=76 from 13 different histologies) and healthy volunteers (N=31). (FIG. 8H) Plasma L-arginine determined by LC/MS from cancer patients (N=26 from 7 different histologies) and healthy volunteers (N=20) (****$P<0.0001$ vs. healthy donor).

4. DETAILED DESCRIPTION

Provided herein are compositions and methods related to treating or preventing a disease (e.g., cancer or a viral infection) in a subject by conjointly administering to the subject an arginase inhibitor (e.g., an arginase inhibitor having a formula disclosed herein) and a composition comprising immune cells (e.g., cytotoxic T cells or natural killer cells). The immune cells may be allogenic or autologous. In some embodiments, the methods further comprise conjointly administering an antibody as disclosed herein.

4.1. Definitions

As used herein, the following terms are intended to have the following meanings:

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O) NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

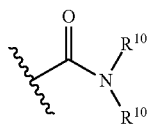

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

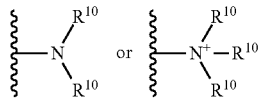

wherein each R10 independently represents a hydrogen or a hydrocarbyl group, or two R10 are taken together with the N atom to which they are attached complete a heterocycle having from 4 to 8 atoms in the ring structure.

The term "aminoalkyl", as used herein, refers to an alkyl group substituted with an amino group.

Unless otherwise specified herein, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a cancer antigen or tumor antigen). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Bivalent mAbs can also consist of 2 IgV domains of 1 specificity and one IgV of the second specificity such that the antibody is bivalent (e.g., binds to 2 things but can have 2 copies of one of the binding specificities). Such antibodies can be engineered by putting two IgVs in tandem on one side of the antibody. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see, e.g., Bird et al. (1988) Science 242:423-426; and Huston et al. (1988) Proc. Natl. Acad. Sci. USA 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) Proc. Natl. Acad. Sci. USA 90:6444-6448; Poljak, R. J., et al. (1994) Structure 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) Human Antibodies and Hybridomas 6:93-101) and use of a cysteine residue, a marker peptide and a C-terminal polyhistidine tag to make bivalent and biotinylated scFv polypeptides (Kipriyanov, S. M., et al. (1994) Mol. Immunol. 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein. As described further herein, the term "antibody" includes genetically engineered or otherwise modified forms of immunoglobulins, such as intrabodies, peptibodies, chimeric antibodies, fully human antibodies, humanized antibodies, and heteroconjugate antibodies (e.g., bispecific antibodies, diabodies, triabodies, tetrabodies, tandem di-scFv, tandem tri-scFv). The term functional antibody fragment also includes antigen binding fragments of antibodies including, but not limited to, fragment antigen binding (Fab) fragment, F(ab')2 fragments, Fab' fragments, Fv fragments, recombinant IgG (rIgG) fragments, single chain variable fragment (scFv) and single domain antibodies (e.g., sdAb, sdFv, nanobody, and the like) fragments.

Antibodies may be polyclonal or monoclonal; xenogeneic, allogeneic, or syngeneic; or modified forms thereof (e.g., humanized, chimeric, etc.). Antibodies may also be fully human. They may also be selective for such antigens such that they can distinguish such antigens from closely related antigens, such as other B7 family members. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

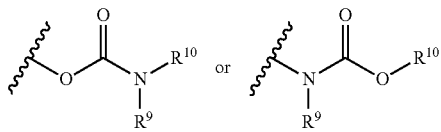

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

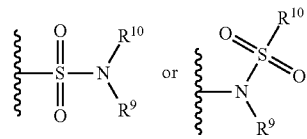

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group. The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

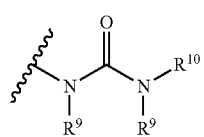

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, $3^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present disclosure (e.g., a compound having a formula provided herein). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present disclosure. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

4.2. Detailed Description

Adoptive Cell Transfer

Disclosed herein are methods related to the treatment of a disease by conjointly administering immune cells and an arginase inhibitor to a subject in need thereof. In some embodiments, the immune cells are T cells (e.g., cytotoxic T cells (CTLs)) or natural killer (NK) cells (e.g., NK-92 natural killer). In some embodiments, the immune cells may express a chimeric antigen receptor (CAR). In some embodiments, the immune cells comprise T cells that express a receptor specific for a disease-associated peptide.

In some embodiments, the immune cells are autologous (e.g., cells derived from the subject receiving the composition and arginase inhibitor). In other embodiments, the immune cells are allogenic (e.g., immune cells obtained from a source other than the subject, such as a cell bank or from a donor). In some embodiments, allogenic immune cells from a bank or donor are HLA matched to the recipient. In some embodiments, the immune cells are stored in a cell bank prior to administration to the subject. In some embodiments, immune cells are selected (e.g., selected from a cell bank) for compatibility with the subject prior to administration to the subject. In some embodiments, the immune cells are selected if they are restricted through an HLA allele shared with the subject. In some embodiments, the immune cells are selected if the immune cells and subject share at least 2 (e.g., at least 3, at least 4, at least 5, at least 6, at least 7, or at least 8) HLA alleles and the immune cells are restricted through a shared HLA allele.

Immune cells disclosed herein may be prepared for administration by any method known in art. In some embodiments, the preparation of immune cells includes obtaining a peripheral blood sample from the subject or a donor, and purifying the sample by removing the monocytes and/or B cells.

a. T Cell Transfer

In some embodiments, the composition comprises T cells (e.g., cytotoxic T cells (CTLs)). T cells (e.g., cytotoxic T cells) disclosed herein may be stimulated and expanded by any technique known in the art. For example, T cells may be stimulated by incubating the T cells with beads coated with anti-CD3 and anti-CD28. Expansion of T cells may involve priming the T cells to a target cell or antigen (e.g., a tumor antigen or a viral antigen) before infusion of T cells into the subject. Expansion of T cells may be done in the presence of antigen presenting cells (APCs). For example, expansion of T cells may be performed in the presence of APCs (e.g., APCs that present a disease-specific peptide), and then administered conjointly with an arginase inhibitor. The APCs may be B cells, dendritic cells, or artificial antigen presenting cells (e.g., artificial antigen-presenting cells such as aK562 cells). In some embodiments, suitable APCs present one or more T cell epitopes (i.e., two or more, three or more, four or more, five or more, six or more, seven or more, eight or more, nine or more, or ten or more). APCs may be transfected with a vector or recombinant adenovirus to express one or more (i.e., two or more, three or more, four or more, five or more, six or more, seven or more, eight or more, nine or more, or ten or more) T cell epitopes. The T cell stimulating and expansion steps can be performed concurrently or sequentially. In some embodiments, the T cells are not enriched (e.g., T cells are not expanded in the presence of APCs disclosed herein).

In some embodiments, the composition comprises CD8+ T cells. In some embodiments, the composition comprises CD4+ T cells. In some embodiments, the composition comprises both CD8+ T cells and CD4+ T cells In some embodiments, the composition comprising immune cells also comprises a cytokine (e.g., IL-2 or IL-15).

In some embodiments, the composition comprising immune cells are conjointly administered with a cytokine, e.g., sequentially or simultaneously.

In some embodiments, the disclosure relates to treating viral infections, for example, in immunodeficient subjects, or subjects that have undergone stem cell transplantation (SCT). Many DNA viruses enjoy lifelong latency in the tissues of the individuals they infect. After SCT in a subject, reactivation of cytomegalovirus (CMV) causing enteritis and pneumonia, Epstein-Barr virus (EBV) causing post-transplant lymphoproliferative disorder, and reactivation or new infection from adenovirus (Ad) causing enteritis, hepatitis, hemorrhagic cystitis, and pneumonia, account for a significant proportion of the serious complications that follow SCT. Therefore, in some embodiments, the methods disclosed herein relate to treating a subject with a viral infection (e.g., an EBV or CMV infection) by administering to the subject a composition comprising immune cells disclosed herein in combination with an arginase inhibitor. In some embodiments, the immune cells comprise T cells that are expanded in the presence of APCs presenting one or more viral peptides (e.g., an EBV or CMV peptide). APCs may present a one or more viral peptides from one or more different viruses. The APCs may be B cells, dendritic cells, or artificial antigen presenting cells (e.g., artificial antigen-presenting cells such as aK562 cells).

b. NK Adoptive Cell Transfer

In some embodiments, the composition comprises natural killer cells. Natural killer (NK) cells are defined as lymphocytes which lyse certain targets without prior sensitization or restriction for products of the major histocompatibility complex (MHC) (Herberman et al., Bolhuis et al., Trinchieri et al., Reynolds et al.). Provided herein are methods of conjointly administering to a subject a composition comprising immune cells (e.g., NK cells, such as NK-92 cells) and an arginase inhibitor disclosed herein. NK cells adoptively transferred to the subject may be autologous or allogenic.

NK cell transfer involves the isolation or purification of NK cells, expansion of NK cells, and infusion or implantation of NK cells into a subject. In some embodiments, NK cells may be purified from a peripheral blood sample. The NK cells may be highly activated (i.e., expanded in the presence of one or more cytokines). In some embodiments, NK cells are expanded or incubated in the presence of one or more cytokines, such as IL-2 or IL-8. NK cell expansion may include alternating time periods of exposure to cytokines, followed by "resting" time periods where NK cells are not incubated with cytokines. In certain embodiments, NK cells can be expanded in the presence of irradiated feeder cells. In some embodiments, the NK cells adhere to a selected target cell type, and have the ability to specifically lyse the target cells. In some embodiments, the NK cells have the ability to lyse target cell types (e.g., tumor cells types or virus infected cells). NK cells may be prepared for administration to the subject by any method known in the art, including, but not limited to, obtaining a preparation of natural killer cells, contacting the preparation with the selected target cell type, selecting natural killer cells based on their adhesion to the selected target cell type, and culturing the selected natural killer cells by promoting proliferation among the NK cells. In some embodiments, an antibody may be administered conjointly with NK adoptive cell therapy.

Antibody Therapies

Provided herein are methods of treating a disease in a subject by conjointly administering to the subject an antibody, a composition comprising immune cells (e.g., as described herein), and an arginase inhibitor as disclosed herein. Some aspects of the disclosure relate to an antibody with a biological activity that is elicited upon binding to its target. This biological activity can include, for example, ADCC, cell lysis, cell death, and/or reduction in tumor size. ADCC may be evaluated in vitro (Kroesen et al., *J. Immunol. Methods,* 156: 47-54, 1992, incorporated by reference in its entirety) or in vivo by using histological analysis to quantify the infiltration of immune cells into a tumor.

In some embodiments, the antibodies provided herein bind to a target cell (e.g., a tumor cell). In some embodiments, the antibodies facilitate the recognition of the target cell by the immune cells administered to the patient. In some embodiments, administration of the antibody results in tumor-inhibitory effects, mediated via antibody-dependent cell-mediated cytotoxicity (ADCC). "Antibody-dependent cell-mediated cytotoxicity (ADCC)" is a mechanism of cell-mediated immunity whereby an effector cell (e.g., an NK cell) of the immune system lyses a target cell to which antibodies are bound. For example, a treatment of a disease (i.e., cancer) may involve administering to the subject a composition comprising NK cells, an antibody which targets and binds a cancer cell or tumor cell (therefore directing NK cells to recognize and neutralize the cancer or tumor cells), and an arginase inhibitor disclosed herein. In other embodiments, the subject is treated with an arginase inhibitor disclosed herein and an antibody to induce in vivo NK cells to attack cancer or tumor cells.

In some embodiments, especially of methods for treating cancer, the antibody is an antibody specific for a cancer antigen and/or a tumor antigen.

Arginase Inhibitors

The present disclosure provides methods for treating or preventing a disease, such as cancer, comprising conjointly administering to a subject in need thereof a composition comprising immune cells and an arginase inhibitor disclosed herein. In some embodiments, the methods further comprise conjointly administering an antibody to the subject.

In certain embodiments, the arginase inhibitor used in the methods of the disclosure is a compound having the structure of Formula I,

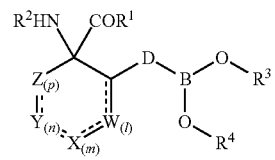

wherein
  $R^1$ is selected from —OH, $OR^a$, and $NR^bR^c$;
  $R^a$ is selected from hydrogen, substituted or unsubstituted alkyl, cycloalkyl, aryl, (heterocycloalkyl)alkyl, (heteroaryl)alkyl, and aralkyl;
  $R^b$ and $R^c$ are each independently selected from H, —OH, substituted or unsubstituted alkyl, —SO$_2$(alkyl), —SO$_2$(aryl), (heterocycloalkyl)alkyl, and (heteroaryl)alkyl;
  $R^2$ is selected from H, substituted or unsubstituted alkyl, and (alkyl)C(O)—;
  W, X, Y, and Z are each independently selected from a bond, —C(R')(R''')—, —C(R''')$_2$—, —CR'''=, —NR'''—, —N=, —O—, —C(O)—, and —S—, such that no more than three of W, X, Y, and Z simultaneously represent a bond; and no two adjacent members of W, X, Y, and Z are simultaneously —O—, —S—, —N—, or —NR'''—;

l, m, n and p are each independently 0, 1, or 2, e.g., 1 or 2;

optionally represents one or more double bonds;

$R^3$ and $R^4$ are each independently selected from hydrogen, substituted or unsubstituted alkyl, and C(O)—R', or $R^3$ and $R^4$ together with the boron atom to which they are bound form a 5- or 6-membered ring that is fully saturated or partially saturated;

D is selected from substituted or unsubstituted alkylene, alkenylene, alkynylene, arylene, and cycloalkylene, wherein one or more —$CH_2$— groups in D are optionally and independently replaced with a moiety Q that is selected from O, NR', S, SO, $SO_2$, and CR'R''; or wherein any two adjacent —$CH_2$— groups optionally are replaced by two members of a cycloalkylenyl group (thereby forming a fused bicyclic system);

provided that D does not contain two adjacent Q moieties selected from O, NR', S, SO, and $SO_2$; and R', R'', and R''' are each independently selected from $S(O)R^d$, $S(O)_2R^d$, alkyl, aryl, —NH(alkyl), alkyl)$_2$, —C(O)$NR^dR^e$, —C(O)(alkyl), —C(O)(aryl), —C(O)O(alkyl), —C(O)O(aryl), cycloalkyl, heterocycloalkyl, heterocycloalkyl), heteroaryl, aralkyl, O(cycloalkyl)alkyl, (heteroaryl)alkyl-, and (heterocycloalkyl)alkyl;

wherein $R^d$ and $R^e$ are each independently selected from H, substituted or unsubstituted alkyl, aralkyl, aryl, hydroxyalkyl, aminoalkyl, cycloalkyl, heterocycloalkyl, heteroaryl, NR'R''C(O)—, and (aryl)cycloalkylene-, wherein any alkyl, alkenyl, alkynyl, aryl, heteroaryl, cycloalkyl, or heterocycloalkyl is optionally substituted, e.g., with one or more members selected from halogen, oxo, —COOH, —CN, —$NO_2$, —OH, —$NR^dR^e$, —$NR^gS(O)_2R^h$, ($C_1$-$C_6$)alkyl, ($C_1$-$C_6$)haloalkyl, ($C_1$-$C_6$)haloalkoxy, ($C_1$-$C_6$)alkoxy, ($C_3$-$C_{14}$)aryl, ($C_3$-$C_{14}$)heteroaryl, ($C_3$-$C_{14}$)heterocycloalkyl, ($C_3$-$C_{14}$)heteroaryl-($C_1$-$C_6$)alkylene and ($C_3$-$C_{14}$)aryloxy;

or a pharmaceutically acceptable salt, stereoisomer, tautomer, or prodrug thereof.

In certain embodiments of the compound of formula I, $R^1$ is selected from —OH, $OR^a$, and $NR^bR^c$;

$R^a$ is selected from hydrogen, straight or branched chain ($C_1$-$C_6$)alkyl, ($C_3$-$C_8$)cycloalkyl, ($C_3$-$C_{14}$)aryl, ($C_3$-$C_{14}$)heterocycloalkyl-($C_1$-$C_6$)alkylene-, ($C_3$-$C_{14}$)heteroaryl-($C_1$-$C_6$)alkylene-, and ($C_3$-$C_{14}$)aryl($C_1$-$C_6$)alkylene-;

$R^b$ and $R^c$ are each independently selected from H, —OH, straight or branched ($C_1$-$C_6$)alkyl, —$SO_2$—($C_1$-$C_6$)alkyl, ($C_3$-$C_{14}$)aryl-$SO_2$, ($C_3$-$C_{14}$)heterocycloalkyl-($C_1$-$C_6$)alkylene-, and ($C_3$-$C_{14}$)heteroaryl-($C_1$-$C_6$)alkylene-;

$R^2$ is selected from H, straight or branched ($C_1$-$C_6$) alkyl, and ($C_1$-$C_6$)alkyl-C(O)—;

W, X, Y, and Z are each independently selected from a bond, —C(R')(R''')—, —C(R''')$_2$—, —CR'''—, —NR'''—, —N—, —O—, —C(O)—, and —S—, such that no more than three of W, X, Y, and Z simultaneously represent a bond; and no two adjacent members of W, X, Y, and Z are simultaneously —O—, —S—, —N—, or —NR'''—;

l, m, n and p are each independently 0, 1, or 2, e.g., 1 or 2;

optionally represents one or more double bonds;

$R^3$ and $R^4$ are each independently selected from hydrogen, straight or branched ($C_1$-$C_6$)alkyl, and C(O)—R', or $R^3$ and $R^4$ together with the boron atom to which they are bound form a 5- or 6-membered ring that is fully saturated or partially saturated;

D is selected from straight or branched ($C_3$-$C_5$)alkylene, straight or branched ($C_2$-$C_8$)alkenylene, straight or branched ($C_2$-$C_8$)alkynylene, ($C_3$-$C_{14}$)arylene, and ($C_3$-$C_{14}$)cycloalkylene, wherein one or more —$CH_2$— groups in D are optionally and independently replaced with a moiety Q that is selected from O, NR', S, SO, $SO_2$, and CR'R''; or wherein any two adjacent —$CH_2$— groups optionally are replaced by two members of a ($C_3$-$C_{14}$)-cycloalkylenyl group;

provided that D does not contain two adjacent Q moieties selected from O, NR', S, SO, and $SO_2$; and R', R'', and R''' are each independently selected from $S(O)R^d$, $S(O)_2R^d$, ($C_1$-$C_8$)alkyl, ($C_3$-$C_6$)aryl, —NH($C_1$-$C_6$)alkyl, $C_6$)alkyl]$_2$, —C(O)$NR^dR^e$, —C(O)($C_1$-$C_6$)alkyl, —C(O)($C_3$-$C_{14}$)aryl, —C(O)O($C_1$-$C_6$)alkyl, —C(O)O($C_3$-$C_{14}$)aryl, ($C_3$-$C_6$)cycloalkyl, ($C_3$-$C_{14}$)heterocycloalkyl, $_3C_{14}$)heterocycloalkyl, ($C_3$-$C_{14}$)heteroaryl, ($C_3$-$C_{14}$)aryl-($C_1$-$C_6$)alkylene-, $C_{14}$)aryl-($C_1$-$C_6$)alkylene-, $O_{34}$($C_3$-$C_6$)cycloalkyl-($C_1$-$C_6$)alkylene-, ($C_3$-$C_{14}$)heteroaryl-($C_1$-$C_6$)alkylene-, and ($C_3$-$C_{14}$)heterocycle-($C_1$-$C_6$)alkylene-;

wherein any alkyl, alkylene, aryl, heteroaryl, cycloalkyl, or heterocycloalkyl is optionally substituted with one or more members selected from halogen, oxo, —$NO_2$, —$NR^gS(O)_2R^h$, ($C_1$-$C_6$)alkoxy, ($C_3$-$C_{14}$)aryl, ($C_1$-$C_6$) haloalkyl and ($C_3$-$C_{14}$)aryloxy;

wherein $R^d$, $R^e$, $R^g$, and $R^h$ are each independently selected from H, straight or branched ($C_1$-$C_6$)alkyl, optionally substituted ($C_3$-$C_{14}$)aryl($C_1$-$C_6$)alkylene-, optionally substituted ($C_3$-$C_{14}$)aryl, ($C_1$-$C_6$)hydroxyalkyl, ($C_1$-$C_6$)aminoalkyl, $H_2N$($C_1$-$C_6$)alkylene-, optionally substituted ($C_3$-$C_6$)cycloalkyl, optionally substituted ($C_3$-$C_{14}$)heterocycloalkyl, optionally substituted ($C_3$-$C_{14}$)heteroaryl, optionally substituted ($C_3$-$C_{14}$)aryl-($C_1$-$C_6$)alkylene-, NR'R''C(O)—, and ($C_3$-$C_6$)aryl-($C_3$-$C_{14}$)-cycloalkylene-.

In further embodiments of the compound of Formula I, $R^1$ is selected from —OH, $OR^a$, and $NR^bR^c$;

$R^a$ is selected from hydrogen, straight or branched chain ($C_1$-$C_6$)alkyl, ($C_3$-$C_8$)cycloalkyl, ($C_3$-$C_{14}$)aryl, ($C_3$-$C_{14}$)heterocycloalkyl-($C_1$-$C_6$)alkylene-, ($C_3$-$C_{14}$)heteroaryl-($C_1$-$C_6$)alkylene-, and ($C_3$-$C_{14}$)aryl($C_1$-$C_6$)alkylene-;

$R^b$ and $R^c$ are each independently selected from H, —OH, straight or branched ($C_1$-$C_6$)alkyl, —$SO_2$—($C_1$-$C_6$) alkyl, ($C_3$-$C_{14}$)aryl-$SO_2$, ($C_3$-$C_{14}$)heterocycloalkyl-($C_1$-$C_6$)alkylene-, and ($C_3$-$C_{14}$)heteroaryl-($C_1$-$C_6$)alkylene-;

$R^2$ is selected from H, straight or branched ($C_1$-$C_6$) alkyl, and ($C_1$-$C_6$)alkyl-C(O)—;

W, X, Y, and Z are each independently selected from a bond, —C(R''')$_2$—, —CR'''—, —NR'''—, —N—, —O—, —C(O)—, and —S—, such that
no more than three of W, X, Y, and Z simultaneously represent a bond; and no two adjacent members of W, X, Y, and Z are simultaneously —O—, —S—, —N—, or —NR'''—;

l, m, n and p are each independently 0, 1, or 2, e.g., 1 or 2;

optionally represents one or more double bonds;

$R^3$ and $R^4$ are each independently selected from hydrogen, straight or branched ($C_1$-$C_6$)alkyl, and C(O)—R', or $R^3$ and $R^4$ together with the boron atom to which they are bound form a 5- or 6-membered ring that is fully saturated or partially saturated;

D is selected from straight or branched ($C_3$-$C_5$)alkylene, straight or branched ($C_2$-$C_8$)alkenylene, straight or branched ($C_2$-$C_8$)alkynylene, ($C_3$-$C_{14}$)arylene, and ($C_3$-$C_{14}$)cycloalkylene,
wherein one or more —CH$_2$— groups in D are optionally and independently replaced with a moiety Q that is selected from O, NR', S, SO, SO$_2$, and CR'R''; or
wherein any two adjacent —CH$_2$— groups optionally are replaced by two members of a ($C_3$-$C_{14}$)-cycloalkylenyl group;
provided that D does not contain two adjacent Q moieties selected from O, NR', S, SO, and SO$_2$; and R', R'' and R''' are each independently selected from H, OH, ($C_1$-$C_8$)alkyl, ($C_3$-$C_6$)aryl, —NH$_2$, —NH($C_1$-$C_6$)alkyl, —N[($C_1$-$C_6$)alkyl]$_2$, —C(O)($C_1$-$C_6$)alkyl, —C(O)($C_3$-$C_{14}$)aryl, —C(O)O($C_1$-$C_6$)alkyl, —C(O)O($C_3$-$C_{14}$)aryl, ($C_3$-$C_6$)cycloalkyl, ($C_3$-$C_{14}$)heterocycloalkyl, ($C_3$-$C_{14}$)heteroaryl, ($C_3$-$C_{14}$)aryl-($C_1$-$C_6$)alkylene-, ($C_3$-$C_6$)cycloalkyl-($C_1$-$C_6$)alkylene-, ($C_3$-$C_{14}$)heteroaryl-($C_1$-$C_6$)alkylene-, and ($C_3$-$C_{14}$)heterocycle-($C_1$-$C_6$)alkylene-;
wherein any alkyl, alkylene, aryl, heteroaryl, cycloalkyl, or heterocycloalkyl is optionally substituted with one or more members selected from halogen, oxo, —COOH, —CN, —NO$_2$, —OH, —NR$^d$R$^e$, —NR$^g$S(O)$_2$R$^h$, ($C_1$-$C_6$) alkoxy, and ($C_3$-$C_{14}$)aryloxy;
wherein R$^d$, R$^e$, R$^g$, and R$^h$ are each independently selected from H, straight or branched ($C_1$-$C_6$)alkyl, optionally substituted ($C_3$-$C_{14}$)aryl($C_1$-$C_6$)alkylene-, optionally substituted ($C_3$-$C_{14}$)aryl, ($C_1$-$C_6$)hydroxyalkyl, ($C_1$-$C_6$)aminoalkyl, H$_2$N($C_1$-$C_6$)alkylene-, optionally substituted ($C_3$-$C_6$)cycloalkyl, optionally substituted ($C_3$-$C_{14}$)heterocycloalkyl, optionally substituted ($C_3$-$C_{14}$)heteroaryl, optionally substituted ($C_3$-$C_{14}$)aryl-($C_1$-$C_6$)alkylene-, NR'R''C(O)—, and ($C_3$-$C_6$)aryl-($C_3$-$C_{14}$)-cycloalkylene-.

In certain embodiments of the compound of Formula I, D is selected from:
-L$^1$-L$^2$-CH$_2$—CH$_2$—,
—CH$_2$-L$^1$-L$^2$-CH$_2$—
—CH$_2$—CH$_2$-L$^1$L$^2$,
-L$^1$-CH$_2$—CH$_2$-L$^2$-,
-L$^1$-CH$_2$-L$^2$-CH$_2$—,
—CH$_2$-L$^1$-CH$_2$-L$^2$-,
-L$^1$CH$_2$—CH$_2$—,
—CH$_2$—CH$_2$-L$^1$-,
-L$^2$-CH$_2$—CH$_2$—,
—CH$_2$-L$^2$-CH$_2$—, and
—CH$_2$—CH$_2$-L$^2$-,
wherein L$^1$ and L$^2$ are independently selected from O, S, SO, SO$_2$, and CR'R''; and
when L$^1$ and L$^2$ are adjacent to each other, then L$^1$ and L$^2$ are not simultaneously O, S, SO, or SO$_2$.

In certain embodiments, D is straight or branched ($C_3$-$C_5$)alkylene. In certain preferred embodiments, D is propylene.

In certain embodiments, $R^1$ is —OH.

In certain embodiments, each of $R^2$, $R^3$ and $R^4$ is hydrogen.

In certain embodiments, the arginase inhibitor is a carbocyclic-based structure. Accordingly, in certain such embodiments, each of W, X, Y and Z is —C(R''')$_2$—. Alternatively, in certain such embodiments, at least two of W, X, Y and Z is —CR''',
and

represents one or more double bonds. In other alternative embodiments, each of W, X, Y and Z is —CR''', and

represents one or more double bonds.

In certain embodiments, wherein R''' is H. In alterative embodiments, at least one occurrence of R''' is not H.

In certain embodiments, the arginase inhibitor is a carbocyclic-based structure having from 3 to 10, 3 to 8, 4 to 8, 4 to 7, 5 to 7, or 5 to 6 ring atoms. In certain such embodiments, l—m+n+p=3. In other embodiments, l+m+n+p=4.

In certain embodiments, the arginase inhibitor is a heterocyclic-based structure. Accordingly, in certain such embodiments, at least one of W, X, Y, or Z is selected from —NR'''—, —N—, —O—, and —S—.

In certain embodiments, any one of W, X, Y and Z is —NH— and each instance of the remaining three is —C(R''')$_2$—. In certain such embodiments, X is NH.

In certain embodiments, wherein R''' is H. In alterative embodiments, at least one occurrence of R∝'' is not H.

The heterocyclic-based structure may optionally contain unsaturation. In certain embodiments, any one of W, X, Y and Z is —N— and at least one of the remaining three is —CR'''—, and

represents one or more double bonds. In certain embodiments, any one of W, X, Y and Z is —N— and each of the remaining three is —CR'''—, and

represents one or more double bonds.

In certain embodiments, X is —N—.

In certain embodiments, wherein R'" is H. In alterative embodiments, at least one occurrence of R'" is not H.

In certain embodiments, the arginase inhibitor is a heterocyclic-based structure having from 3 to 10, 3 to 8, 4 to 8, 4 to 7, 5 to 7, or 5 to 6 ring atoms. In certain embodiments, the sum of l, m, n, and p is 3, 4, 5, or 6. In certain embodiments, l+m+n+p=4.

In certain embodiments, the arginase inhibitor is not 1-amino-2-(3-boronopropyl)cyclohexane carboxylic acid.

In certain embodiments, the arginase inhibitor for use with the methods of the disclosure is selected from the following:

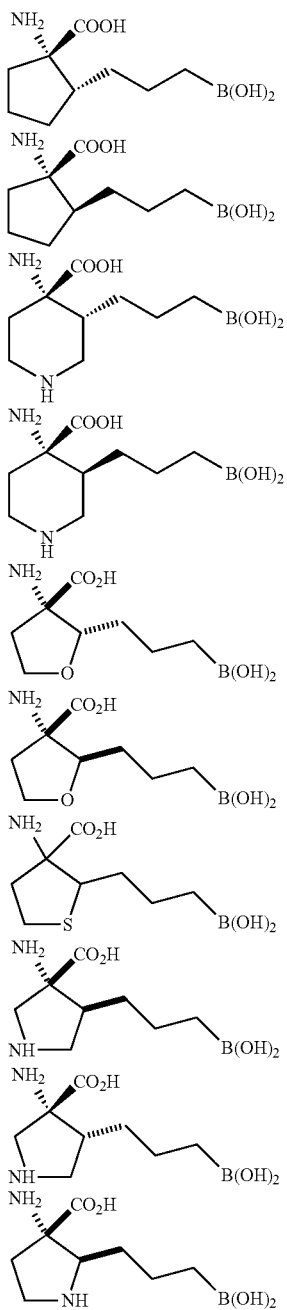

or a pharmaceutically acceptable salt, stereoisomer, or prodrug thereof.

In certain embodiments, the arginase inhibitor for use with the methods of the disclosure is selected from the following:

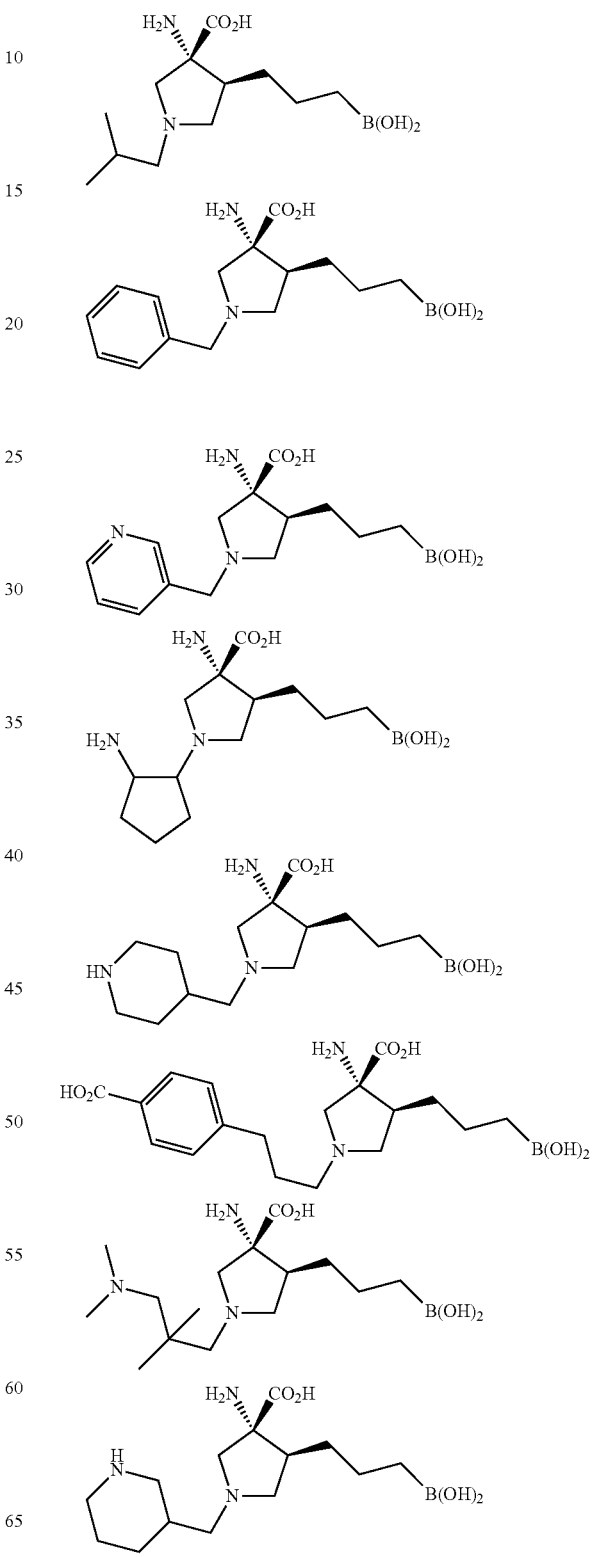

25
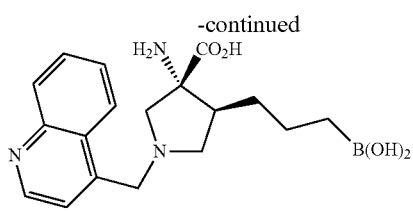
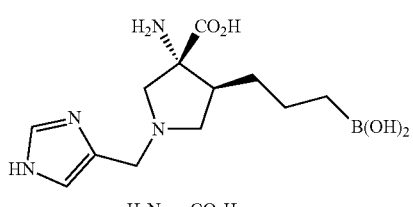
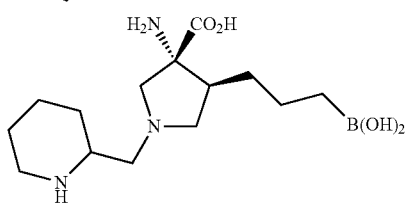
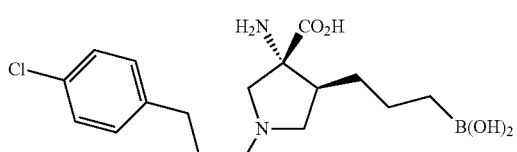
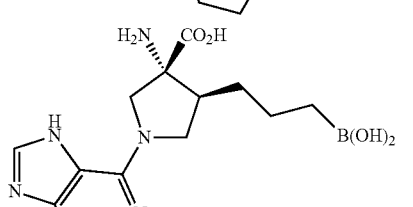
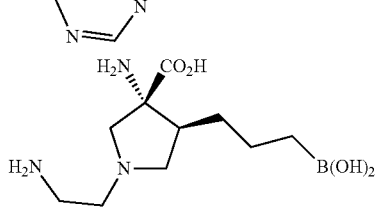
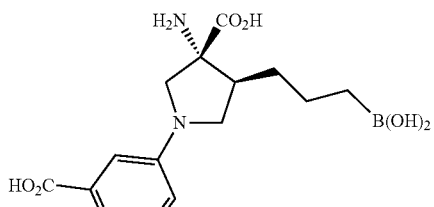
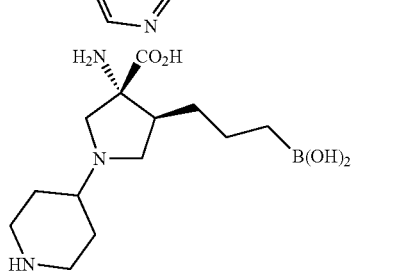
26
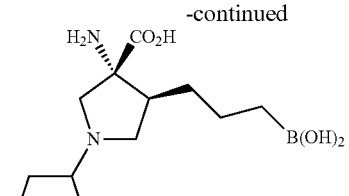
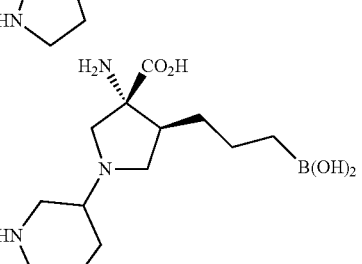
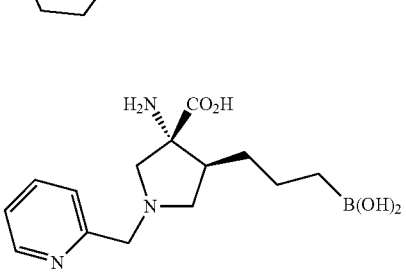
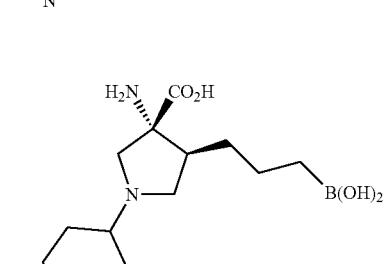
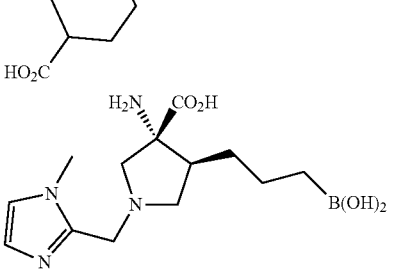
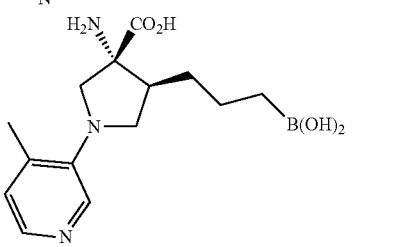
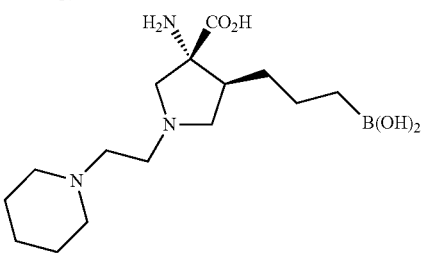

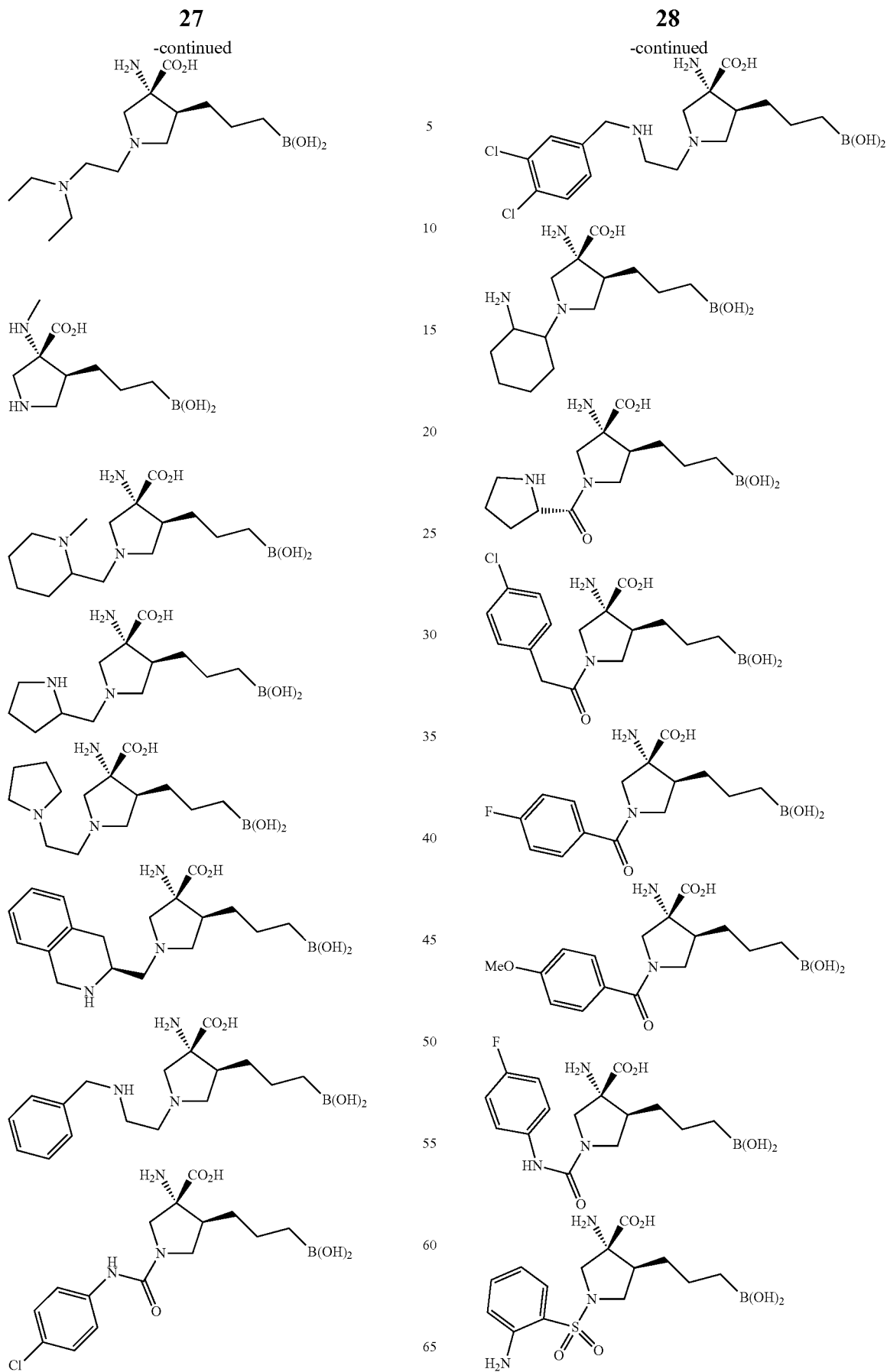

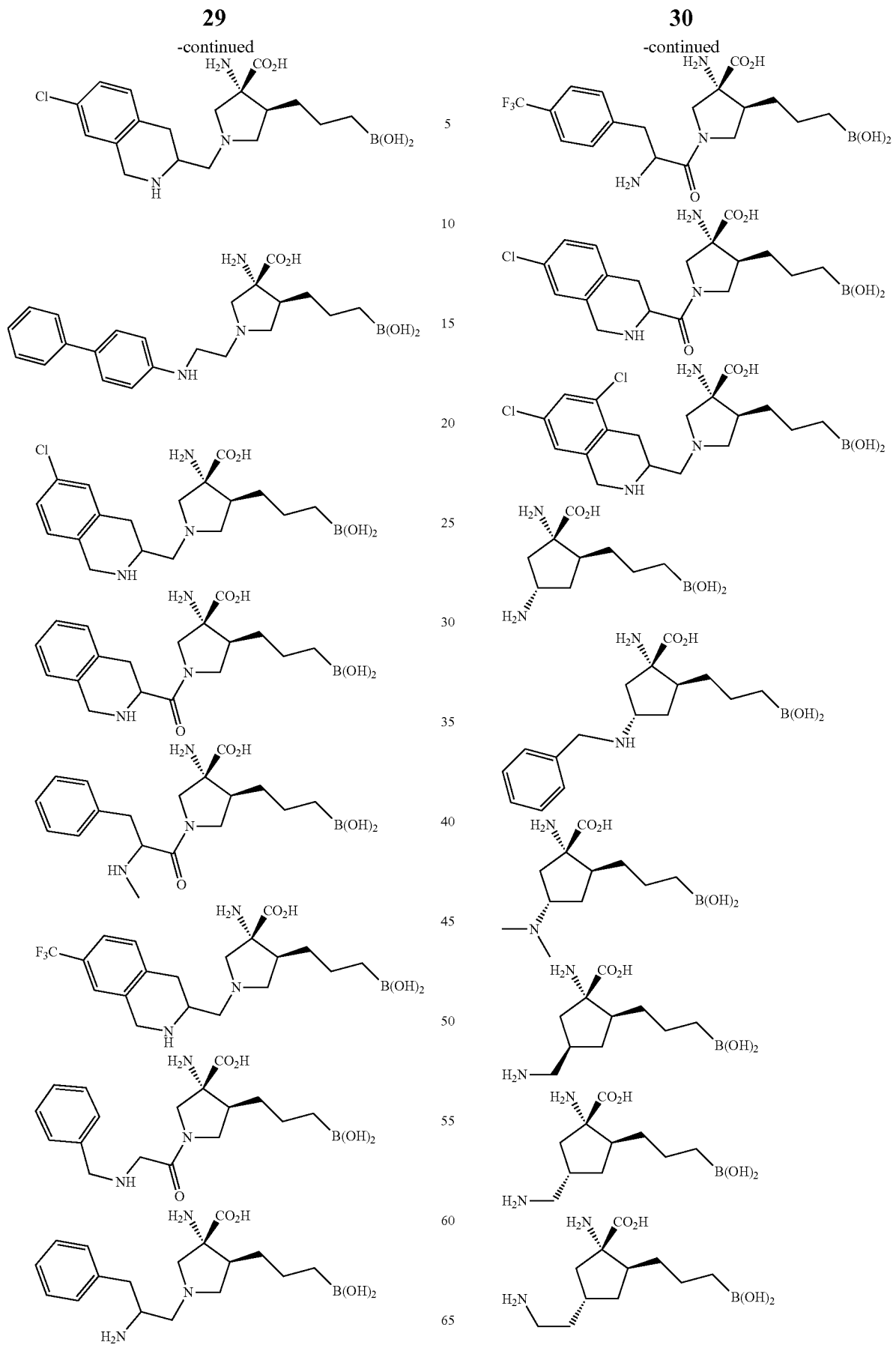

or a pharmaceutically acceptable salt, stereoisomer, or prodrug thereof.

In certain embodiments, the arginase inhibitor used in the methods of the disclosure is a compound having the structure of Formula II,

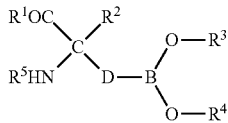

wherein:
- $R^1$ is selected from —OH, $OR^a$, and $NR^bR^c$;
  - $R^a$ is selected from hydrogen, substituted or unsubstituted alkyl, aryl, (heterocycloalkyl)-alkyl, heteroaralkyl, and aralkyl;
  - $R^b$ and $R^c$ are each independently selected from H, —OH, substituted or unsubstituted alkyl, —S(O)$_2$(alkyl), —S(O)$_2$(aryl), (heterocycloalkyl)alkyl, and heteroaralkyl;
- (A) $R^2$ is selected from substituted or unsubstituted alkyl, alkenyl, alkynyl, aryl, cycloalkyl, aralkyl, heteroaralkyl, heteroaryl, heterocycloalkyl, (heterocycloalkyl)alkyl, (heteroaryl)heterocycloalkylene, (aryl)heterocycloalkylene, (aralkyl)heterocycloalkylene, (heteroaralkyl)heterocycloalkylene, ((heterocycloalkyl)alkyl)heterocycloalkylene, and —(CH$_2$)$_m$—(X)$_u$—(CH$_2$)$_n$—(Y)$_v$—$R^f$;
  wherein
  - u and v are each independently 0 or 1, and u+v=1;
  - m and n are each independently 0, 1, 2, 3, 4, 5, or 6, wherein m+n≥1;
  - X and Y are independently selected from —NH, —O— and —S—;
  - $R^f$ is selected from H, hydroxyl, substituted or unsubstituted alkyl and aryl; and
  - $R^5$ is selected from substituted or unsubstituted alkyl or alkyl-C(O)—; or
- (B) $R^2$ is (heterocycloalkyl)alkyl; and
  - $R^5$ is selected from H, substituted or unsubstituted alkyl, and alkyl-C(O)—;
- $R^3$ and $R^4$ are each independently selected from hydrogen, substituted or unsubstituted alkyl, and C(O)—R', or $R^3$ and $R^4$ together with the boron atom to which they are bound form a 5- or 6-membered ring that is fully or partially saturated, and that optionally contains 1-3 additional heteroatom ring members selected from O, S, and N;
- D is selected from substituted or unsubstituted alkylene, alkenylene, alkynylene, arylene, and cycloalkylene,
  - wherein one or more —CH$_2$— groups in D are optionally and independently replaced with a moiety Q that is selected from O, NR', S, SO, SO$_2$, and CR'R''; or
  - wherein any two adjacent —CH$_2$— groups optionally are replaced by two members of a cycloalkylenyl group;
  - provided that D does not contain two adjacent Q moieties selected from O, NR', S, SO, and SO$_2$; and
- R' and R'' are each independently selected from H, substituted or unsubstituted alkyl, and aryl;
- wherein any alkyl, alkenyl, alkynyl, aryl, heteroaryl, cycloalkyl, or heterocycloalkyl is optionally substituted, e.g., with one or more members selected from halogen, oxo, —COOH, —CN, —NO$_2$, —OH, —NR$^d$R$^e$, —NR$^g$S(O)$_2$R$^h$, (C$_1$-C$_6$)alkyl, (C$_1$-C$_6$)haloalkyl, (C$_1$-C$_6$)haloalkoxy, (C$_1$-C$_6$)alkoxy, (C$_3$-C$_{14}$)aryl, (C$_3$-C$_{14}$)heteroaryl, (C$_3$-C$_{14}$)heterocycloalkyl, (C$_3$-C$_{14}$)heteroaryl-(C$_1$-C$_6$)alkylene and (C$_3$-C$_{14}$)aryloxy;

or a pharmaceutically acceptable salt, stereoisomer, tautomer, or prodrug thereof.

In certain embodiments, the arginase inhibitor has the structure of the compound of Formula II, wherein:
- $R^1$ is selected from —OH, $OR^a$, and $NR^bR^c$;
  - $R^a$ is selected from hydrogen, straight or branched chain (C$_1$-C$_6$)alkyl, (C$_3$-C$_{14}$)aryl, (C$_3$-C$_{14}$)heterocycloalkyl-(C$_1$-C$_6$)alkylene-, (C$_3$-C$_{14}$)heteroaryl-(C$_1$-C$_6$)alkylene-, and (C$_3$-C$_{14}$)aryl(C$_1$-C$_6$)alkylene-;
  - $R^b$ and $R^c$ are each independently selected from H, —OH, straight or branched (C$_1$-C$_6$)alkyl, —S(O)$_2$—(C$_1$-C$_6$)alkyl, (C$_3$-C$_{14}$)aryl-S(O)$_2$—, (C$_3$-C$_{14}$)heterocycloalkyl-(C$_1$-C$_6$)alkylene-, and (C$_3$-C$_{14}$)heteroaryl-(C$_1$-C$_6$)alkylene-;
- (A) $R^2$ is selected from straight or branched (C$_1$-C$_6$)alkyl, straight or branched (C$_2$-C$_6$)alkenyl, straight or branched (C$_2$-C$_6$)alkynyl, (C$_3$-C$_{14}$)aryl, (C$_3$-C$_{14}$)-cycloalkyl, (C$_3$-C$_{14}$)aryl(C$_1$-C$_6$)alkylene-, (C$_3$-C$_{14}$)heteroaryl-(C$_1$-C$_6$)alkylene-, (C$_3$-C$_{14}$)heteroaryl, (C$_3$-C$_{14}$)heterocycloalkyl, (C$_3$-C$_{14}$)heterocycloalkyl-(C$_1$-C$_6$)alkylene-, (C$_3$-C$_{14}$)heteroaryl-(C$_3$-C$_6$)heterocycloalkylene-, (C$_3$-C$_{14}$)aryl-(C$_3$-C$_{14}$)heterocycloalkylene-, (C$_3$-C$_{14}$)-aryl-(C$_1$-C$_6$)alkyl-(C$_3$-C$_{14}$)heterocycloalkylene-, (C$_3$-C$_{14}$)heteroaryl-(C$_1$-C$_6$)alkyl-(C$_3$-C$_{14}$)heterocycloalkylene-, (C$_3$-C$_{14}$)heterocycloalkyl-(C$_1$-C$_6$)alkyl-(C$_3$-C$_{14}$)heterocycloalkylene-, and —(CH$_2$)$_m$—(X)$_u$—(CH$_2$)$_n$—(Y)$_v$—$R^f$;
  wherein
  - u and v are each independently 0 or 1, and u+v=1;
  - m and n are each independently 0, 1, 2, 3, 4, 5, or 6, wherein m+n≥1;
  - X and Y are independently selected from —NH, —O— and —S—;
  - $R^f$ is selected from H, hydroxyl, straight or branched (C$_1$-C$_6$)alkyl and (C$_3$-C$_{14}$)aryl; and
  - $R^5$ is selected from straight or branched (C$_1$-C$_6$) alkyl or (C$_1$-C$_6$)alkyl-C(O)—; or
- (B) $R^2$ is (C$_3$-C$_{14}$)heterocycloalkyl-(C$_1$-C$_2$)alkylene-; and
  - $R^5$ is selected from H, straight or branched (C$_1$-C$_6$) alkyl, and (C$_1$-C$_6$)alkyl-C(O)—;
- $R^3$ and $R^4$ are each independently selected from hydrogen, straight or branched (C$_1$-C$_6$)alkyl, and C(O)—R', or $R^3$ and $R^4$ together with the boron atom to which they are bound form a 5- or 6-membered ring that is fully or partially saturated, and that optionally contains 1-3 additional heteroatom ring members selected from O, S, and N; and
- D is selected from straight or branched (C$_1$-C$_6$)alkylene, straight or branched (C$_2$-C$_8$)alkenylene, straight or branched (C$_2$-C$_8$)alkynylene, (C$_3$-C$_{14}$)arylene, and (C$_3$-C$_{14}$)cycloalkylene,
  - wherein one or more —CH$_2$— groups in D are optionally and independently replaced with a moiety Q that is selected from O, NR', S, SO, SO$_2$, and CR'R''; or
  - wherein any two adjacent —CH$_2$— groups optionally are replaced by two members of a (C$_3$-C$_{14}$)-cycloalkylenyl group;
  - provided that D does not contain two adjacent Q moieties selected from O, NR', S, SO, and SO$_2$;
- wherein any alkyl, alkylene, alkenyl, alkenylene, alkynyl, or alkynylene is optionally substituted with one or more members selected from halogen, oxo, —COOH, —CN, —NO$_2$, —OH, —NR$^d$R$^e$, —NR$^g$S(O)$_2$R$^h$, (C$_1$-C$_6$)alkoxy, and (C$_3$-C$_{14}$)aryloxy;

wherein R$^d$, R$^e$, R$^g$, and R$^h$ are each independently selected from H, straight or branched (C$_1$-C$_6$)alkyl, optionally substituted (C$_3$-C$_{14}$)aryl(C$_1$-C$_6$)alkylene-, (C$_1$-C$_6$)alkoxy, optionally substituted (C$_3$-C$_{14}$)aryl, (C$_1$-C$_6$)hydroxyalkyl, (C$_1$-C$_6$)aminoalkyl, H$_2$N(C$_1$-C$_6$)alkylene-, optionally substituted (C$_3$-C$_6$)cycloalkyl, optionally substituted (C$_3$-C$_{14}$)heterocycloalkyl, optionally substituted (C$_3$-C$_{14}$)heteroaryl, optionally substituted (C$_3$-C$_{14}$)aryl-(C$_1$-C$_6$)alkylene-, NR'R''C(O)—, and (C$_3$-C$_6$)aryl-(C$_3$-C$_{14}$)-cycloalkylene-, and R' and R'' are each independently selected from H, (C$_1$-C$_8$)alkyl, and (C$_3$-C$_6$)aryl; and wherein any aryl, heteroaryl, cycloalkyl, or heterocycloalkyl is optionally substituted with one or more members selected from halogen, —OH, oxo, —COOH, (C$_3$-C$_{14}$)aryl(C$_1$-C$_6$)alkylene-, —CN, —NO$_2$, —NH$_2$, (C$_1$-C$_6$)alkyl-S—, (C$_3$-C$_{14}$)cycloalkyl, (C$_3$-C$_{14}$)heterocycloalkyl, (C$_3$-C$_{14}$)aryl, (C$_3$-C$_{14}$)heteroaryl, —C(O)NH—(C$_1$-C$_6$)alkyl, —NHC(O)—(C$_1$-C$_6$)alkyl, (C$_1$-C$_6$)alkyl, (C$_2$-C$_8$)alkenyl, (C$_2$-C$_8$)alkynyl, (C$_1$-C$_6$)alkoxy, (C$_1$-C$_6$)haloalkyl, and (C$_1$-C$_6$)hydroxyalkyl.

D is selected from:
-L$^1$-L$^2$-CH$_2$—CH$_2$—,
—CH$_2$-L$^1$-L$^2$-CH$_2$—
—CH$_2$—CH$_2$-L$^1$-L$^2$,
-L$^1$-CH$_2$—CH$_2$-L$^2$-, and
-L$^1$-CH$_2$-L$^2$-CH$_2$—,
wherein L$^1$ and L$^2$ are independently selected from O, NR', S, SO, SO$_2$, and CR'R''.

In certain embodiments, D is straight or branched (C$_3$-C$_5$)alkylene. In certain preferred embodiments, D is butylene.

In certain embodiments, R$^1$ is —OH.

In certain embodiments, (A) R$^2$ is selected from straight or branched (C$_1$-C$_6$)alkyl, straight or branched (C$_2$-C$_6$)alkenyl, straight or branched (C$_2$-C$_6$)alkynyl, (C$_3$-C$_{14}$)aryl, (C$_3$-C$_{14}$)-cycloalkyl, (C$_3$-C$_{14}$)aryl(C$_1$-C$_6$)alkylene-, (C$_3$-C$_{14}$)heteroaryl-(C$_1$-C$_6$)alkylene-, (C$_3$-C$_{14}$)heteroaryl, (C$_3$-C$_{14}$)heterocycloalkyl, (C$_3$-C$_{14}$)heterocycloalkyl-(C$_1$-C$_6$)alkylene-, (C$_3$-C$_{14}$)heteroaryl-(C$_3$-C$_6$)heterocycloalkylene-, (C$_3$-C$_{14}$)aryl-(C$_3$-C$_{14}$)heterocycloalkylene-, (C$_3$-C$_{14}$)-aryl-(C$_1$-C$_6$)alkyl-(C$_3$-C$_{14}$)heterocycloalkylene-, (C$_3$-C$_{14}$)heteroaryl-(C$_1$-C$_6$)alkyl-(C$_3$-C$_{14}$)heterocycloalkylene-, (C$_3$-C$_{14}$)heterocycloalkyl-(C$_1$-C$_6$)alkyl-(C$_3$-C$_{14}$)heterocycloalkylene-, and —(CH$_2$)$_m$—(X)$_u$—(CH$_2$)$_n$—(Y)$_v$—R$^f$; and
each of R$^3$ and R$^4$ is hydrogen
OR
(B) R$^2$ is (C$_3$-C$_{14}$)heterocycloalkyl-(C$_1$-C$_2$)alkylene-; and each of R$^3$, and R$^4$ and R$^5$ is hydrogen.

In certain embodiments, R$^2$ is selected from (C$_1$-C$_6$)alkyl, (C$_3$-C$_{14}$)aryl, (C$_3$-C$_{14}$)heteroaryl, (C$_3$-C$_{14}$)heterocycloalkyl, (C$_3$-C$_{14}$)heterocycloalkyl-(C$_1$-C$_6$)alkylene-, (C$_3$-C$_{14}$)heteroaryl-(C$_1$-C$_6$)alkylene-, (C$_3$-C$_{14}$)aryl-(C$_1$-C$_6$)alkylene- and —(CH$_2$)$_n$—(X)$_u$—(CH$_2$)$_m$—(Y)$_v$—R$^f$, and R$^5$ is selected from straight or branched (C$_1$-C$_6$) alkyl or (C$_1$-C$_6$)alkyl-C(O)—.

In certain embodiments, R$^2$ is alkyl optionally substituted by hydroxy or —NR$^d$R$^e$. In certain such embodiments, R$^d$ and R$^e$ is independently selected from H, straight or branched (C$_1$-C$_6$)alkyl, (C$_1$-C$_6$)aminoalkyl, optionally substituted (C$_3$-C$_{14}$)aryl-(C$_1$-C$_6$)alkylene-, optionally substituted (C$_3$-C$_{14}$)aryl, and optionally substituted (C$_3$-C$_6$)cycloalkyl. In certain preferred embodiments, R$^d$ and R$^e$ is (C$_1$-C$_6$)aminoalkyl.

In certain embodiments, R$^2$ is —(CH$_2$)$_n$—(X)$_u$—(CH$_2$)$_m$—(Y)$_v$—R$^f$. In certain such embodiments, X and Y are each independently —NH—. In further certain such embodiments, m is 1 and n is 2. In further certain such embodiments, each of u and v is 1.

In certain embodiments, R$^2$ is (C$_3$-C$_6$)heterocycloalkyl-(C$_1$-C$_2$)alkylene optionally substituted with one or more members selected from —(C$_1$-C$_6$)alkoxy, —(C$_1$-C$_6$)alkyl, and —OH.

In certain embodiments, R$^2$ is (C$_3$-C$_{14}$)heteroaryl-(C$_1$-C$_6$)alkylene-.

In certain embodiments, the arginase inhibitor of formula II is not 2-amino-4-borono-2-methylbutanoic acid.

In certain exemplary embodiments, the arginase inhibitor is selected from the following compounds:

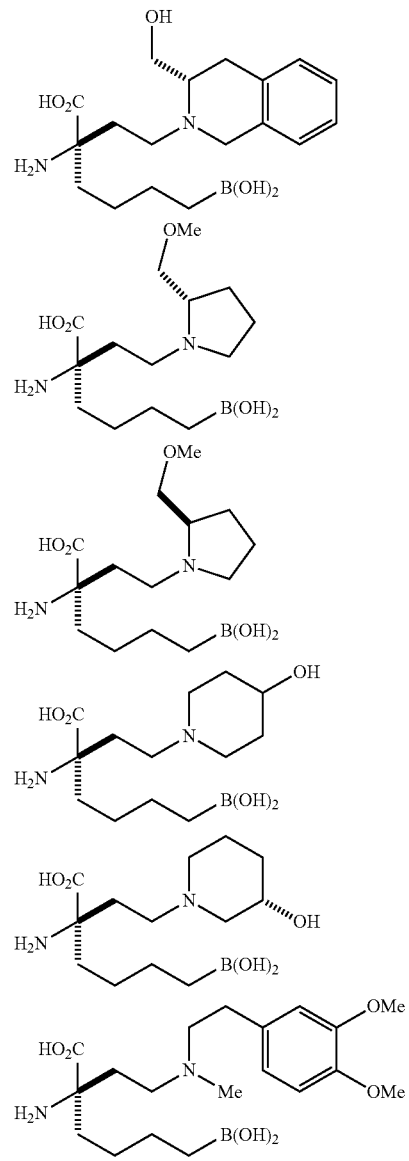

-continued
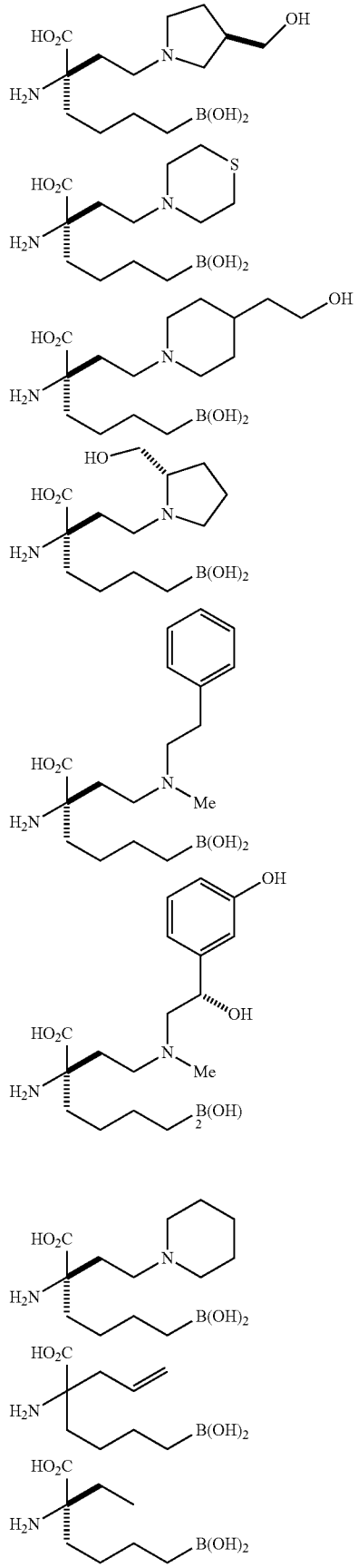
-continued
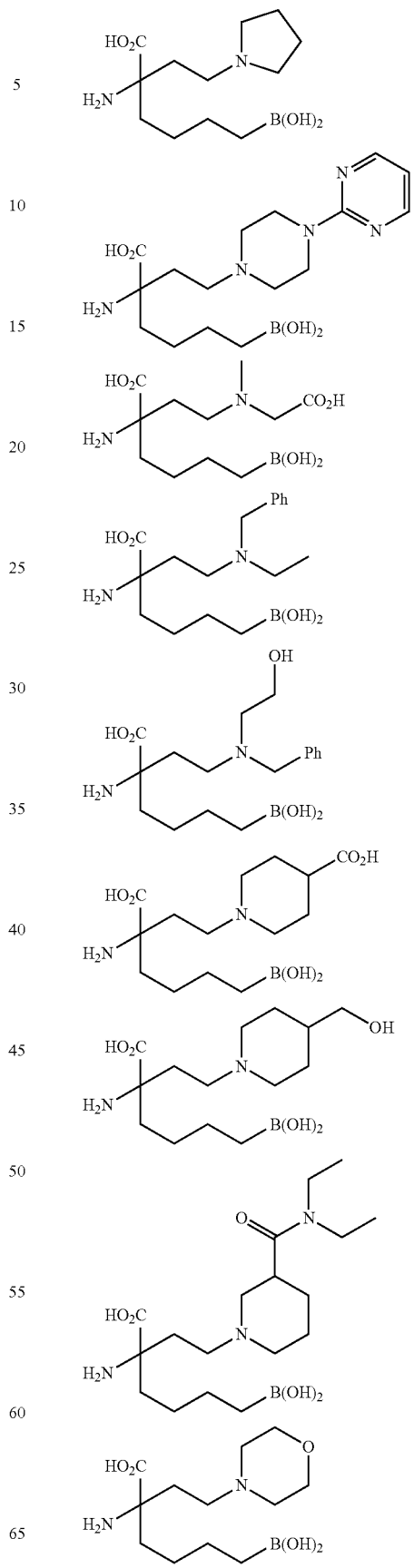

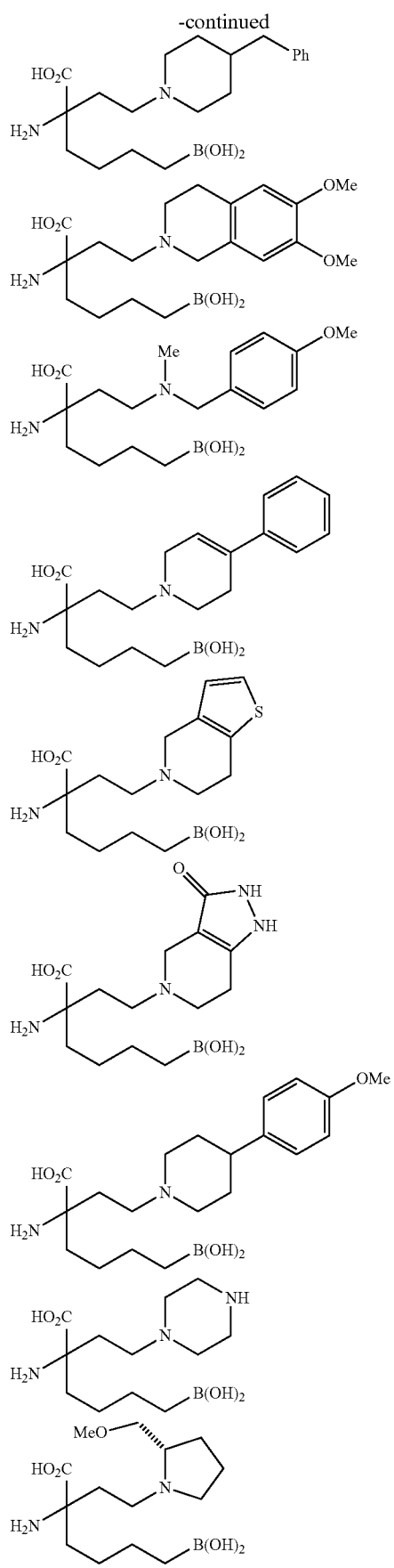
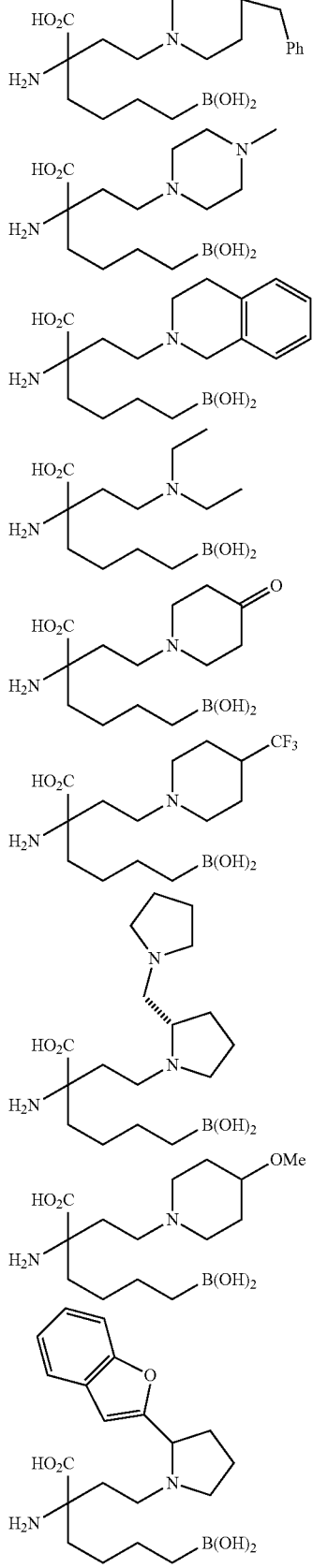

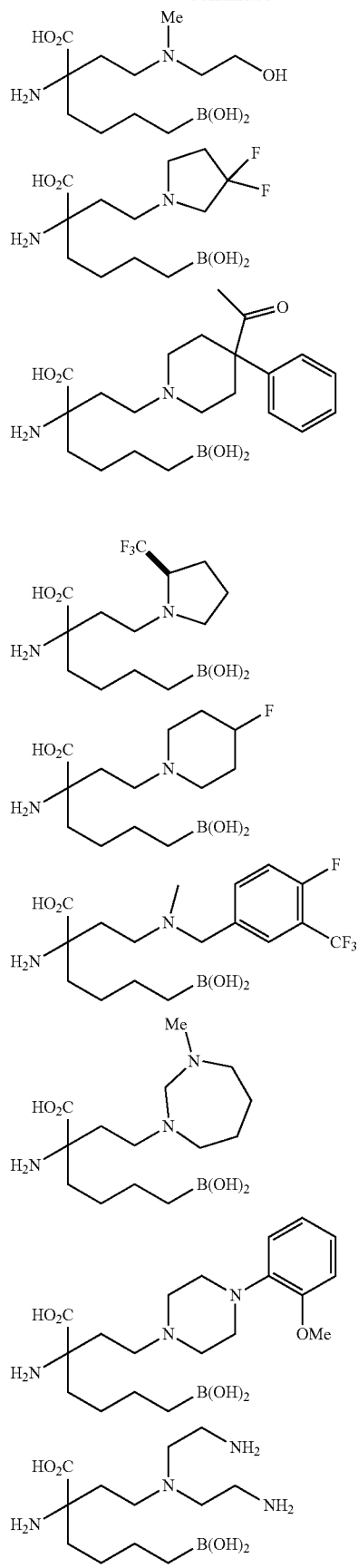
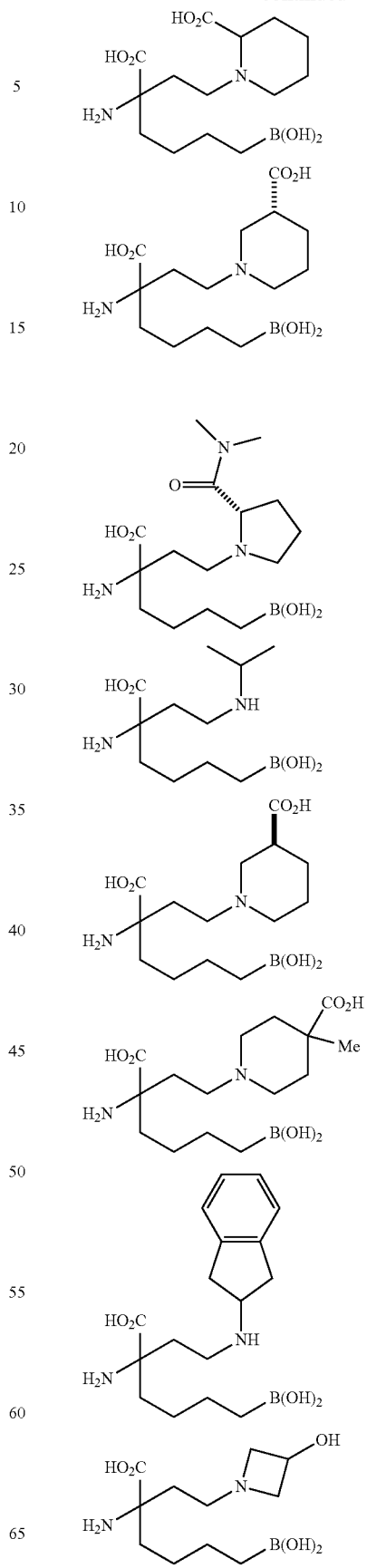

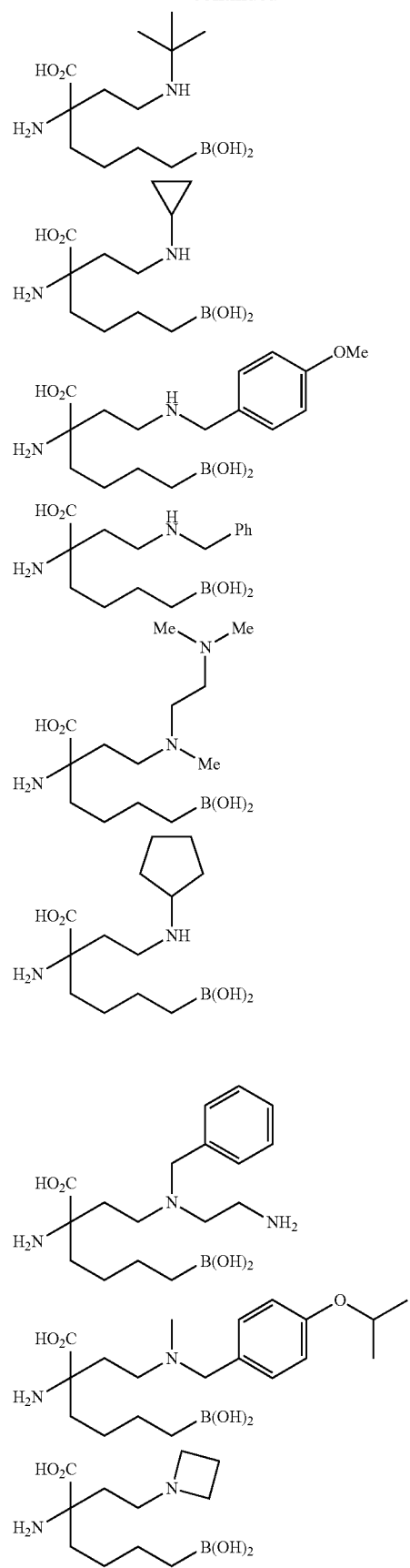

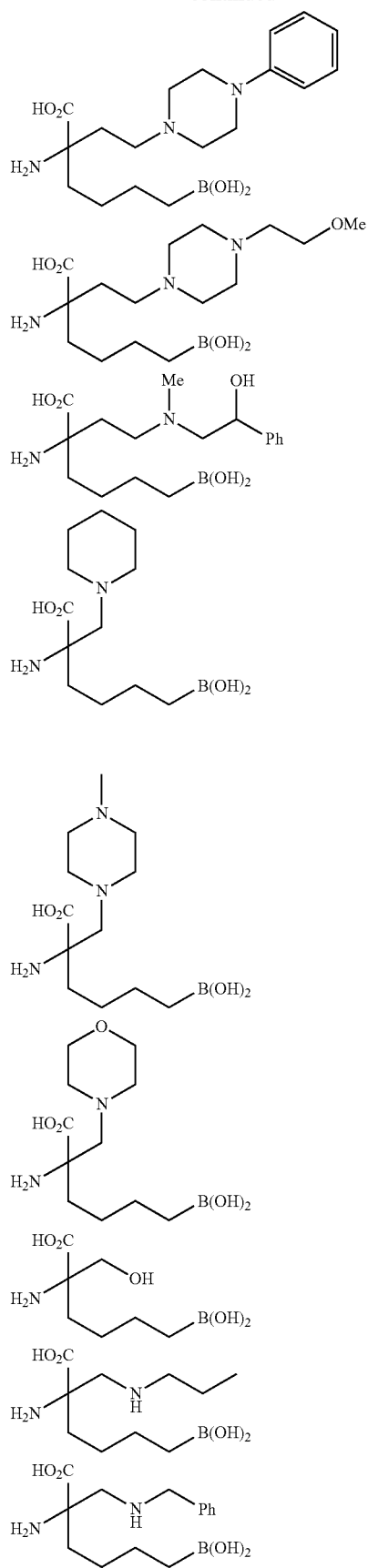
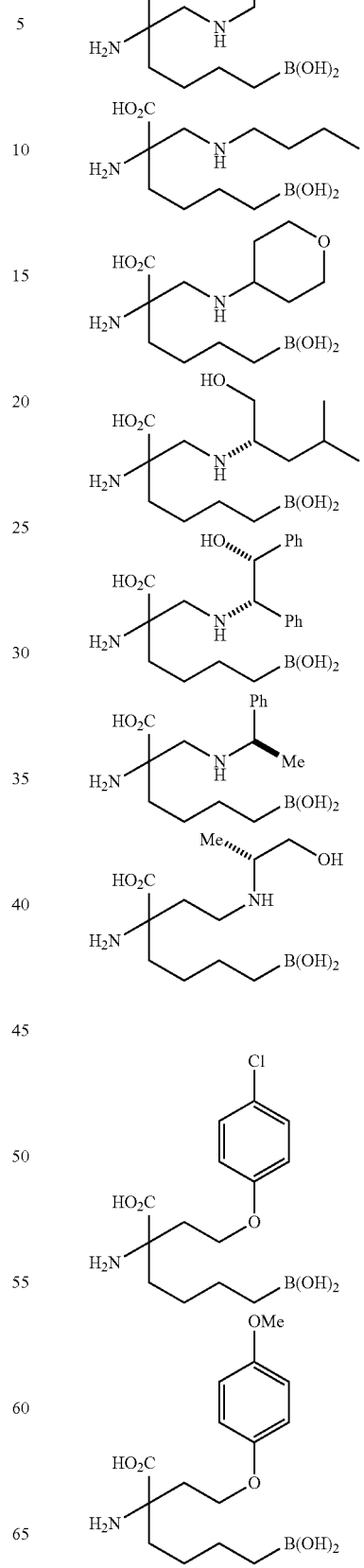

-continued
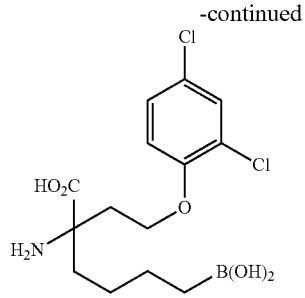
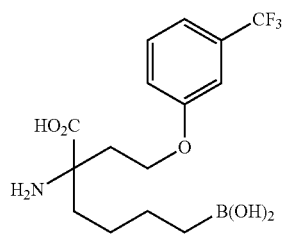
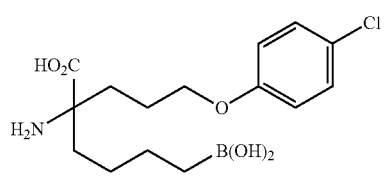
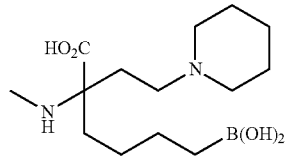
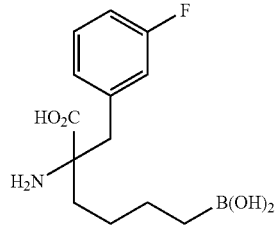
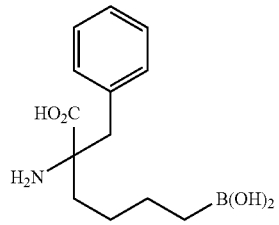
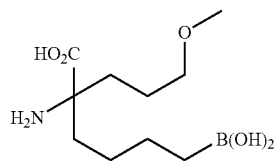
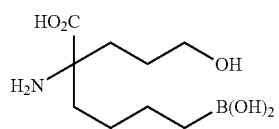
-continued
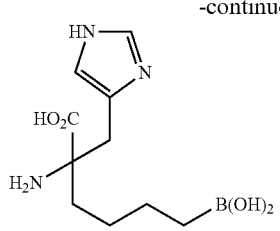
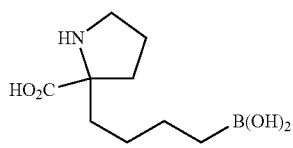
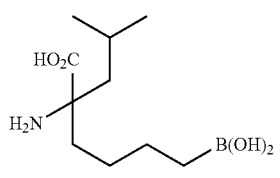
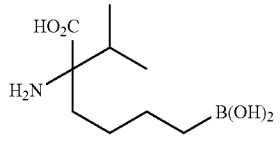
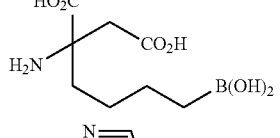
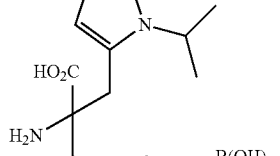
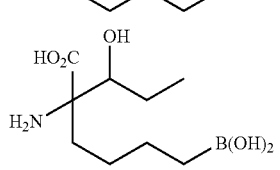
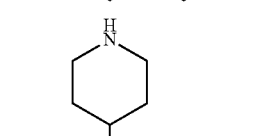
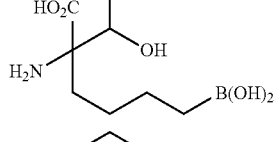
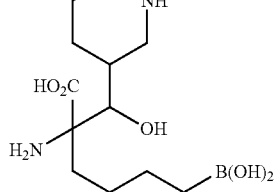
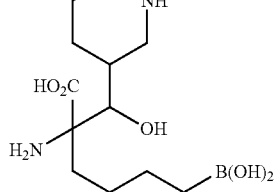
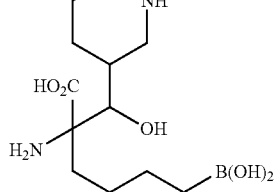

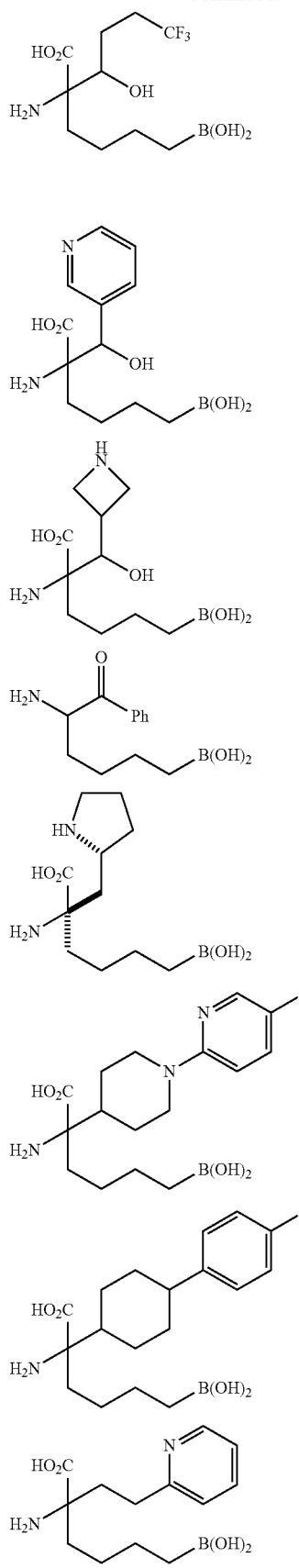
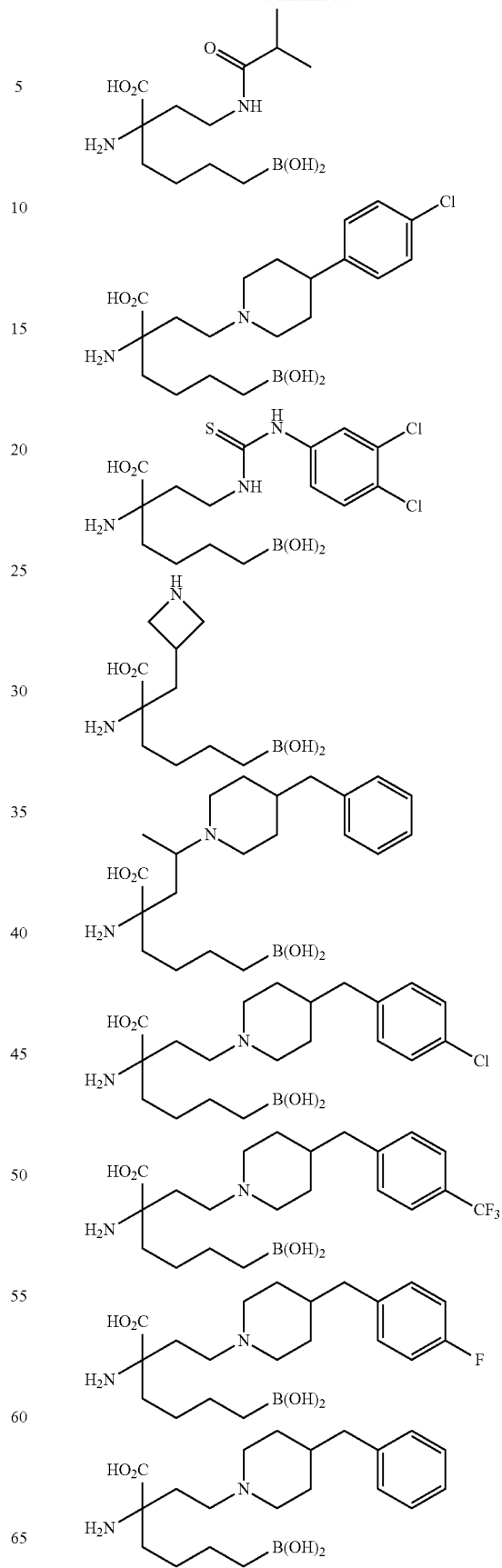

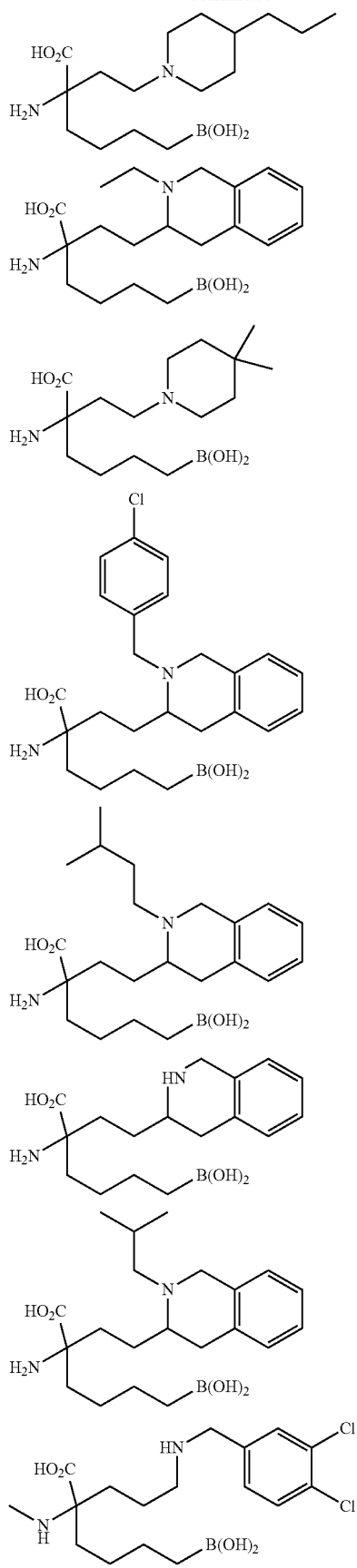
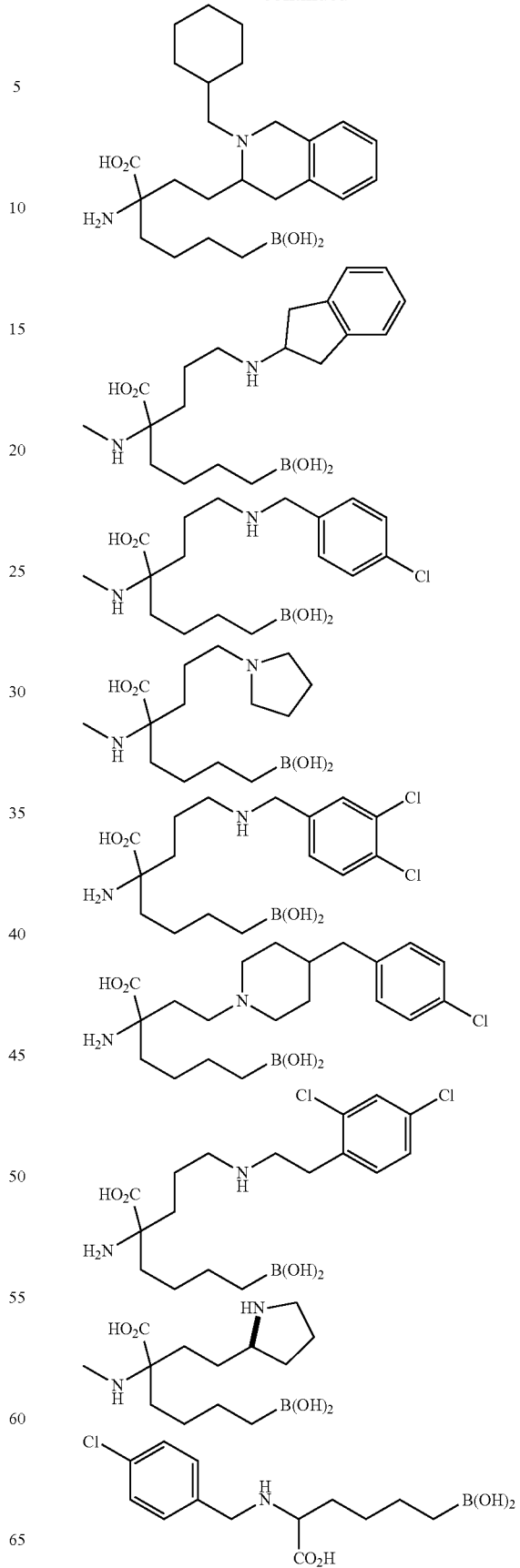

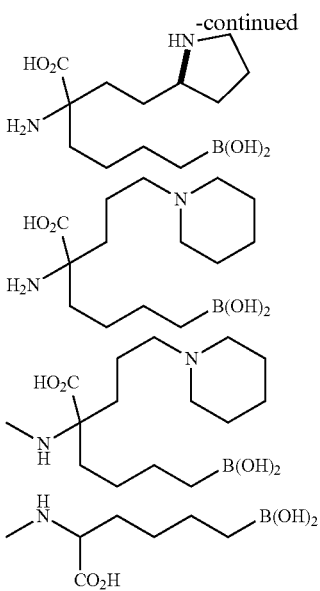

In certain embodiments, the arginase inhibitor used in the methods of the disclosure is a compound having the structure of Formula III,

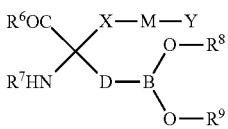

III wherein
$R^6$ is selected from $OR^a$, and $NR^bR^c$;
  $R^a$ is selected from hydrogen, substituted or unsubstituted alkyl, cycloalkyl, aryl, (heterocycloalkyl)alkyl, heteroaralkyl, and aralkyl;
  $R^b$ and $R^c$ are each independently selected from H, —OH, substituted or unsubstituted alkyl, —S(O)$_2$(alkyl), —S(O)$_2$(aryl), (heterocycloalkyl)alkyl, and heteroaralkyl;
$R^7$ is selected from H, substituted or unsubstituted alkyl, aralkyl, heteroaralkyl, (heterocycloalkyl)alkyl and (alkyl)C(O)—;
X is selected from cycloalkylene and heterocycloalkylene,
Y is selected from H, alkyl, —NR'R", hydroxyalkyl, cycloalkyl, (cycloalkyl)alkyl, aryl, aralkyl, heterocycloalkyl, (heterocycloalkyl)alkyl, heteroaryl, heteroaralkyl, (heteroaryl)heterocycloalkyl, (aryl)heterocycloalkyl, (aralkyl)heterocycloalkyl, (heteroaralkyl)heterocycloalkyl, and ((heterocycloalkyl)alkyl)heterocycloalkyl;
M is selected from a bond, alkylene, —O—, —C(O)—, —C(S)—, —C(O)NH—, —C(S)NH—, —S—, —S(O)—, —S(O)$_2$—, —NR'—, and —C═NR'—;
$R^8$ and $R^9$ are independently selected from hydrogen, substituted or unsubstituted alkyl, cycloalkyl, aryl, and C(O)—R',
or $R^8$ and $R^9$ together with the boron atom to which they are bound form a 5- or 6-membered ring that is fully saturated or partially saturated and that optionally contains 1-3 additional heteroatom ring members selected from O, S, and N,
  wherein the ring is optionally fused with a cycloalkyl, heterocyclic or aromatic ring;
D is selected from substituted or unsubstituted alkylene, alkenylene, alkynylene, arylene, and cycloalkylene,
  wherein one or more —CH$_2$— groups in D are optionally and independently replaced with a moiety Q that is selected from O, NR', S, SO, SO$_2$, and CR'R"; or
  wherein any two adjacent —CH$_2$— groups optionally are replaced by two members of a cycloalkylenyl group; and
  provided that D does not contain two adjacent Q moieties selected from O, NR', S, SO, and SO$_2$; and
R' and R" are independently selected from H, substituted or unsubstituted alkyl, —C(O)(alkyl), aryl, aralkyl, aminoalkyl, cycloalkyl, heterocycloalkyl, heteroaryl;
wherein any alkyl, alkenyl, alkynyl, aryl, heteroaryl, cycloalkyl, or heterocycloalkyl is optionally substituted, e.g., with one or more members selected from halogen, oxo, —COOH, —CN, —NO$_2$, —OH, —NR$^d$R$^e$, —NR$^g$S(O)$_2$R$^h$, (C$_1$-C$_6$)alkyl, (C$_1$-C$_6$)haloalkyl, (C$_1$-C$_6$)haloalkoxy, (C$_1$-C$_6$)alkoxy, (C$_3$-C$_{14}$)aryl, (C$_3$-C$_{14}$)heteroaryl, (C$_3$-C$_{14}$)heterocycloalkyl, (C$_3$-C$_{14}$)heteroaryl-(C$_1$-C$_6$)alkylene and (C$_3$-C$_{14}$)aryloxy;
or a pharmaceutically acceptable salt, stereoisomer, tautomer, or prodrug thereof.

In certain embodiments, the arginase inhibitor is a compound of Formula III, wherein:
$R^6$ is selected from $OR^a$, and $NR^bR^c$;
  $R^a$ is selected from hydrogen, straight or branched chain (C$_1$-C$_6$)alkyl, (C$_3$-C$_8$)cycloalkyl, (C$_3$-C$_{14}$)aryl, (C$_3$-C$_{14}$)heterocycloalkyl-(C$_1$-C$_6$)alkylene-, (C$_3$-C$_{14}$)heteroaryl-(C$_1$-C$_6$)alkylene-, and (C$_3$-C$_{14}$)aryl(C$_1$-C$_6$)alkylene-;
  $R^b$ and $R^c$ are each independently selected from H, —OH, straight or branched (C$_1$-C$_6$)alkyl, —S(O)$_2$—(C$_1$-C$_6$)alkyl, (C$_3$-C$_{14}$)aryl-S(O)$_2$—, (C$_3$-C$_{14}$)heterocycloalkyl-(C$_1$-C$_6$)alkylene-, and (C$_3$-C$_{14}$)heteroaryl-(C$_1$-C$_6$)alkylene-;
$R^7$ is selected from H, straight or branched (C$_1$-C$_6$) alkyl, (C$_3$-C$_{14}$)aryl(C$_1$-C$_6$)alkylene-, (C$_3$-C$_{14}$)heteroaryl-(C$_1$-C$_6$)alkylene-, (C$_3$-C$_{14}$)heterocycloalkyl-(C$_1$-C$_6$)alkylene- and (C$_1$-C$_6$)alkyl-C(O)—;
X is selected from (C$_3$-C$_{14}$)-cycloalkylene and (C$_3$-C$_{14}$) heterocycloalkylene,
Y is selected from H, (C$_1$-C$_{14}$)alkyl, —NR'R", hydroxy (C$_1$-C$_6$)alkylene, (C$_3$-C$_{14}$)-cycloalkyl, (C$_3$-C$_{14}$)-cycloalkyl-(C$_1$-C$_6$)alkylene, (C$_3$-C$_{14}$)aryl, (C$_3$-C$_{14}$)aryl-(C$_1$-C$_6$)alkylene, (C$_3$-C$_{14}$)heterocycloalkyl, (C$_3$-C$_{14}$)heterocycloalkyl-(C$_1$-C$_6$)alkylene, (C$_3$-C$_{14}$)heteroaryl, (C$_3$-C$_{14}$)heteroaryl-(C$_1$-C$_6$)alkylene, (C$_3$-C$_{14}$)heteroaryl-(C$_3$-C$_6$)heterocycloalkylene-, (C$_3$-C$_{14}$)aryl-(C$_3$-C$_{14}$)heterocycloalkylene-, (C$_3$-C$_{14}$)-aryl-(C$_1$-C$_6$)alkyl-(C$_3$-C$_{14}$)heterocycloalkylene-, (C$_3$-C$_{14}$)heteroaryl-(C$_1$-C$_6$)alkyl-(C$_3$-C$_{14}$)heterocycloalkylene-, and (C$_3$-C$_{14}$)heterocycloalkyl-(C$_1$-C$_6$)alkyl-(C$_3$-C$_{14}$)heterocycloalkylene-;
M is selected from a bond, —(C$_1$-C$_6$)alkylene-, —O—, —C(O)—, —C(S)—, —C(O)NH—, —C(S)NH—, —S—, —S(O)—, —S(O)$_2$—, —NR'—, and —C═NR"—;
$R^8$ and $R^9$ are independently selected from hydrogen, straight or branched (C$_1$-C$_6$)alkyl, (C$_3$-C$_8$)cycloalkyl, (C$_3$-C$_{14}$)aryl, and C(O)—R',
or $R^8$ and $R^9$ together with the boron atom to which they are bound form a 5- or 6-membered ring that is fully saturated, or partially saturated and that optionally contains 1-3 additional heteroatom ring members selected from O, S, and N, wherein the ring is optionally fused with a cycloalkyl, heterocyclic or aromatic ring;

D is selected from straight or branched $(C_3-C_5)$alkylene, straight or branched $(C_2-C_8)$alkenylene, straight or branched $(C_2-C_8)$alkynylene, $(C_3-C_{14})$arylene, and $(C_3-C_{14})$cycloalkylene, wherein one or more —$CH_2$— groups in D are optionally and independently replaced with a moiety Q that is selected from O, NR', S, SO, $SO_2$, and CR'R"; or wherein any two adjacent —$CH_2$— groups optionally are replaced by two members of a $(C_3-C_{14})$-cycloalkylenyl group;

provided that D does not contain two adjacent Q moieties selected from O, NR', S, SO, and $SO_2$; and R' and R" are independently selected from H, $(C_1-C_8)$ alkyl, —C(O)—$(C_1-C_8)$alkylene, optionally substituted $(C_3-C_6)$aryl, optionally substituted $(C_3-C_{14})$aryl $(C_1-C_6)$alkylene-, optionally substituted $(C_1-C_6)$ aminoalkyl, optionally substituted $(C_3-C_6)$cycloalkyl, optionally substituted $(C_3-C_{14})$heterocycloalkyl, optionally substituted $(C_3-C_{14})$heteroaryl;

wherein any alkyl, alkylene, aryl, heteroaryl, cycloalkyl, or heterocycloalkyl is optionally substituted with one or more members selected from halogen, oxo, —COOH, —CN, —$NO_2$, —OH, —$NR^dR^e$, —$NR^gS(O)_2R^h$, $(C_1-C_6)$alkyl, $(C_1-C_6)$haloalkyl, $(C_1-C_6)$haloalkoxy, $(C_1-C_6)$alkoxy, $(C_3-C_{14})$aryl, $(C_3-C_{14})$heteroaryl, $(C_3-C_{14})$heterocycloalkyl, $(C_3-C_{14})$heteroaryl-$(C_1-C_6)$alkylene and $(C_3-C_{14})$aryloxy;

wherein $R^d$, $R^e$, $R^g$, and $R^h$ are each independently selected from H, straight or branched $(C_1-C_6)$alkyl, optionally substituted $(C_3-C_{14})$aryl$(C_1-C_6)$alkylene-, optionally substituted $(C_3-C_{14})$aryl, $(C_1-C_6)$hydroxyalkyl, $(C_1-C_6)$aminoalkyl, $H_2N(C_1-C_6)$alkylene-, optionally substituted $(C_3-C_6)$cycloalkyl, optionally substituted $(C_3-C_{14})$heterocycloalkyl, optionally substituted $(C_3-C_{14})$heteroaryl, optionally substituted $(C_3-C_{14})$ aryl-$(C_1-C_6)$alkylene-, and NR'R"C(O)—.

In certain embodiments of the compound of Formula III, D is selected from:

-$L^1$-$L^2$-$CH_2$—$CH_2$—,
—$CH_2$-$L^1$-$L^2$-$CH_2$—
—$CH_2$—$CH_2$-$L^1$-$L^2$,
-$L^1$-$CH_2$—$CH_2$-$L^2$-, and
-$L^1$-$CH_2$-$L^2$-$CH_2$—, wherein $L^1$ and $L^2$ are independently selected from O, NR', S, SO, $SO_2$, and CR'R".

In certain embodiments, D is straight or branched $(C_3-C_5)$alkylene, such as butylene.

In certain embodiments, $R^1$ is —OH

In certain embodiments, $R^7$, $R^8$ and $R^9$ are hydrogen.

In certain embodiments, X is $(C_3-C_{14})$-cycloalkylene, M is selected from a bond, —$(C_1-C_6)$alkylene-, —O—, —C(O)—, —C(S)—, —C(O)NH—, —C(S)NH—, —S—, —S(O)—, —$S(O)_2$—, —NR'—, and —C=NR"—; and Y is —NR'R".

In certain embodiments, M is a bond and Y is —$NH_2$.

In certain embodiments, X is $(C_3-C_{14})$heterocycloalkylene; M is selected from a bond, —$(C_1-C_6)$alkylene-, —O—, —C(O)—, —C(S)—, —C(O)NH—, —C(S)NH—, —S—, —S(O)—, —$S(O)_2$—, —NR'—, and —C=NR"—; and Y is selected from $(C_3-C_{14})$-cycloalkyl, $(C_3-C_{14})$aryl, $(C_3-C_{14})$aryl-$(C_1-C_6)$alkylene, $(C_3-C_{14})$heteroaryl and $(C_3-C_{14})$heteroaryl-$(C_1-C_6)$alkylene.

In certain embodiments, the arginase inhibitor used in the methods of the disclosure is selected from:

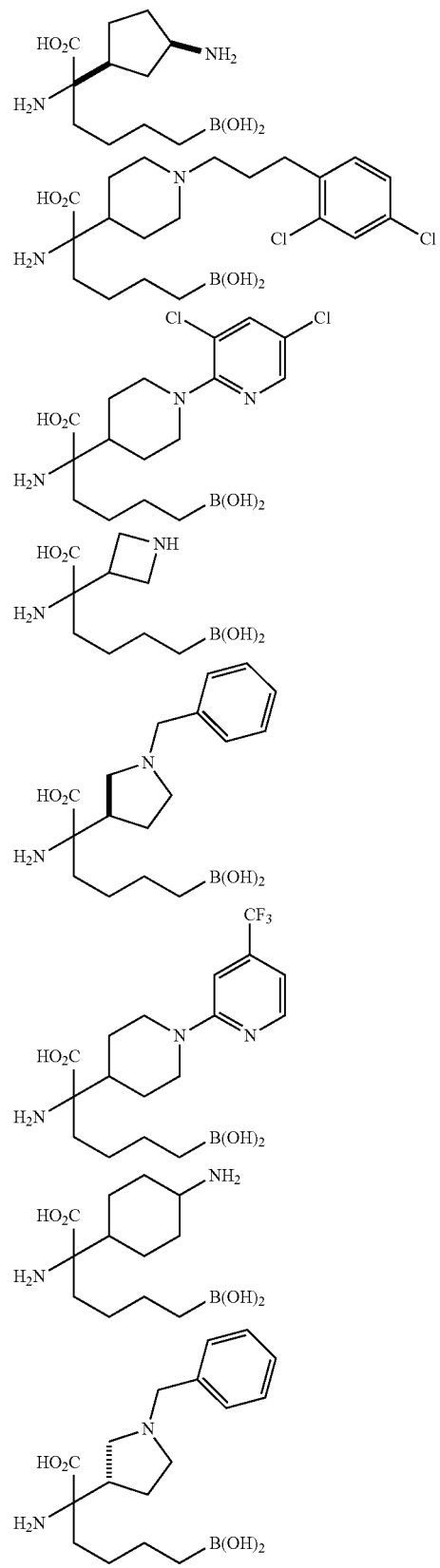

-continued
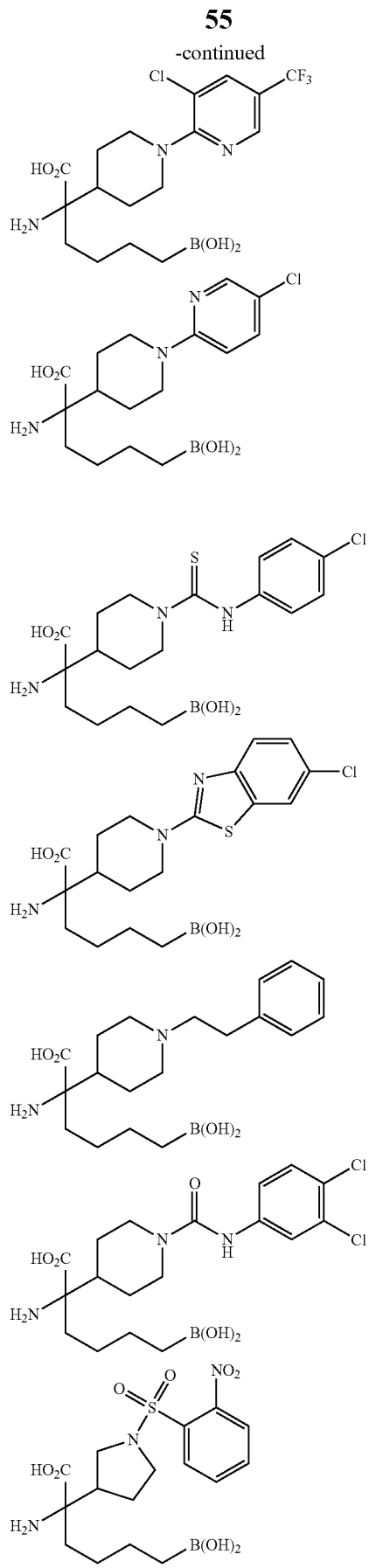
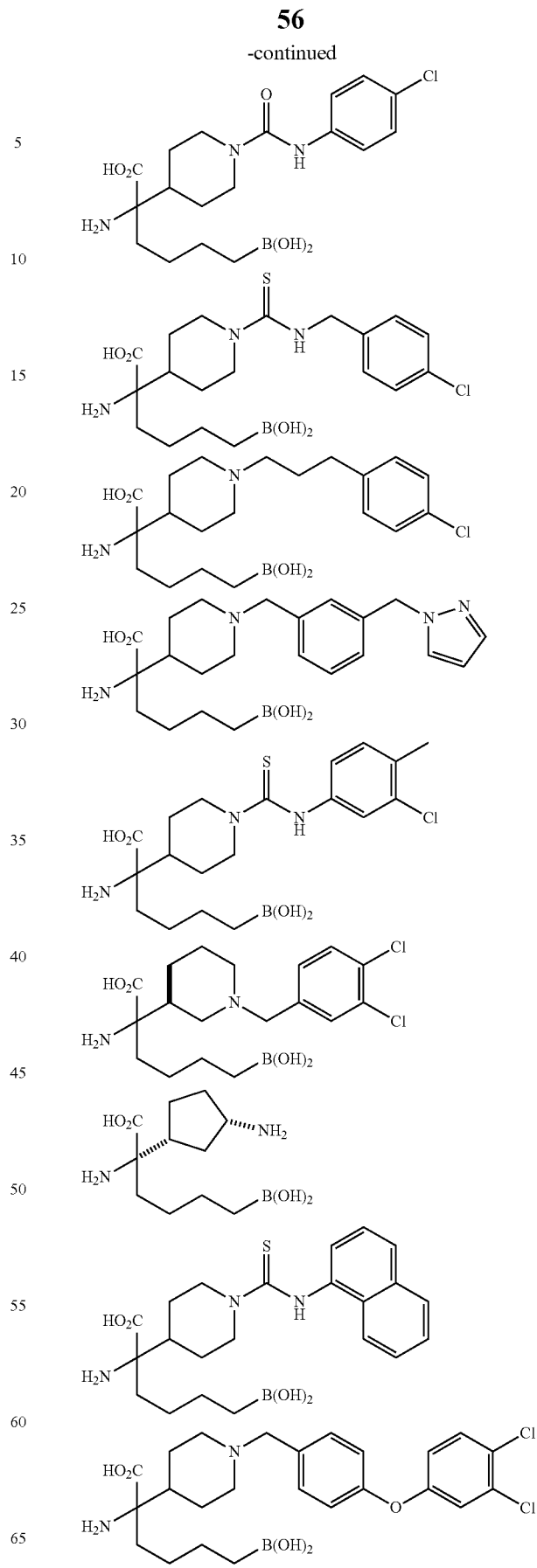

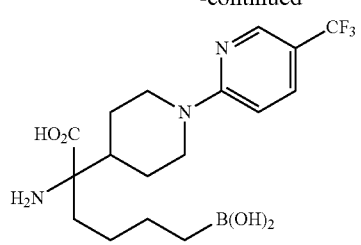
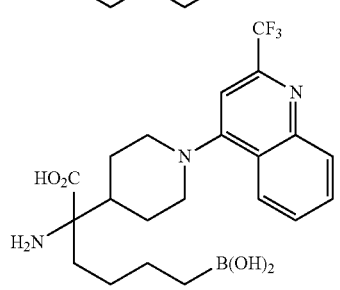
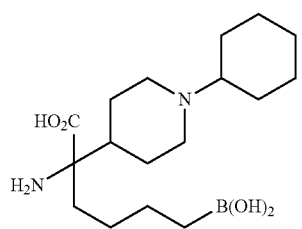
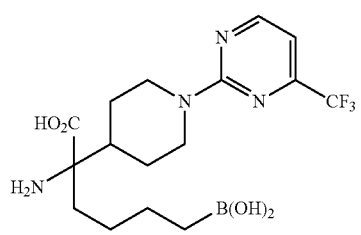
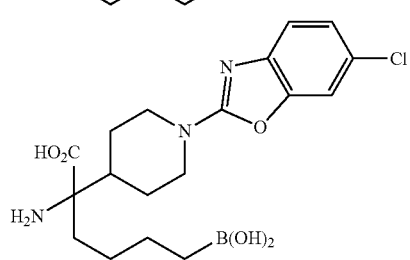
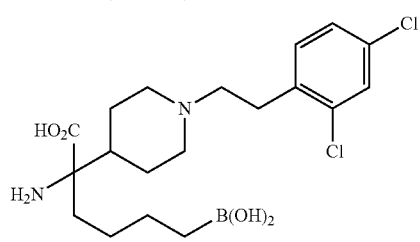
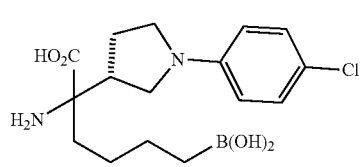
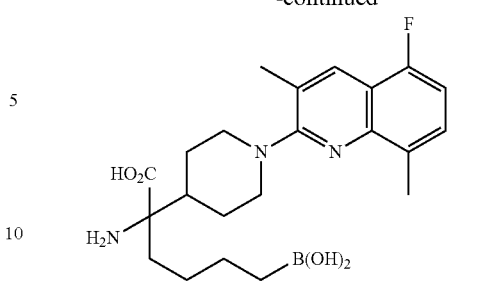
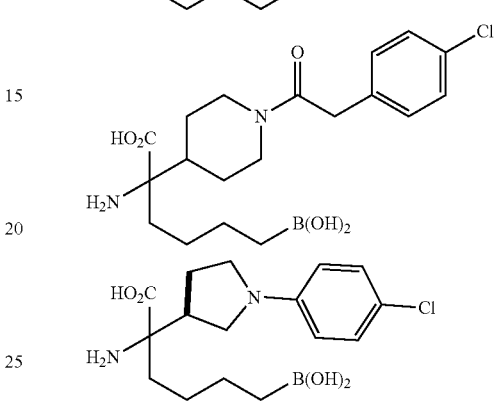
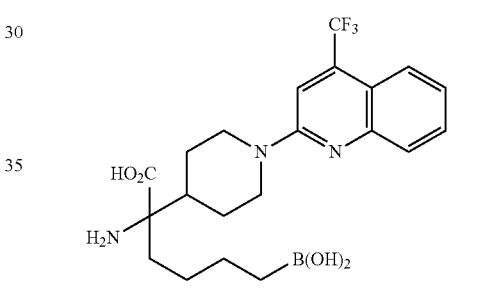
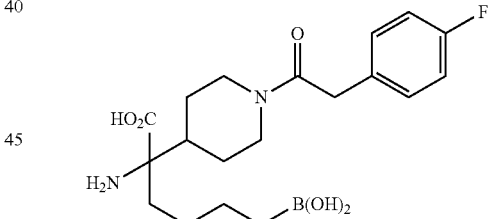
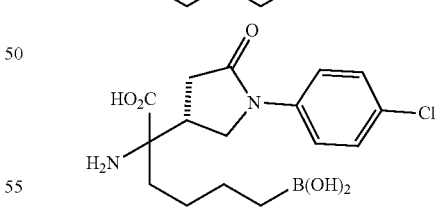
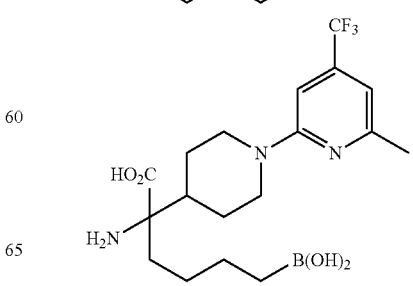

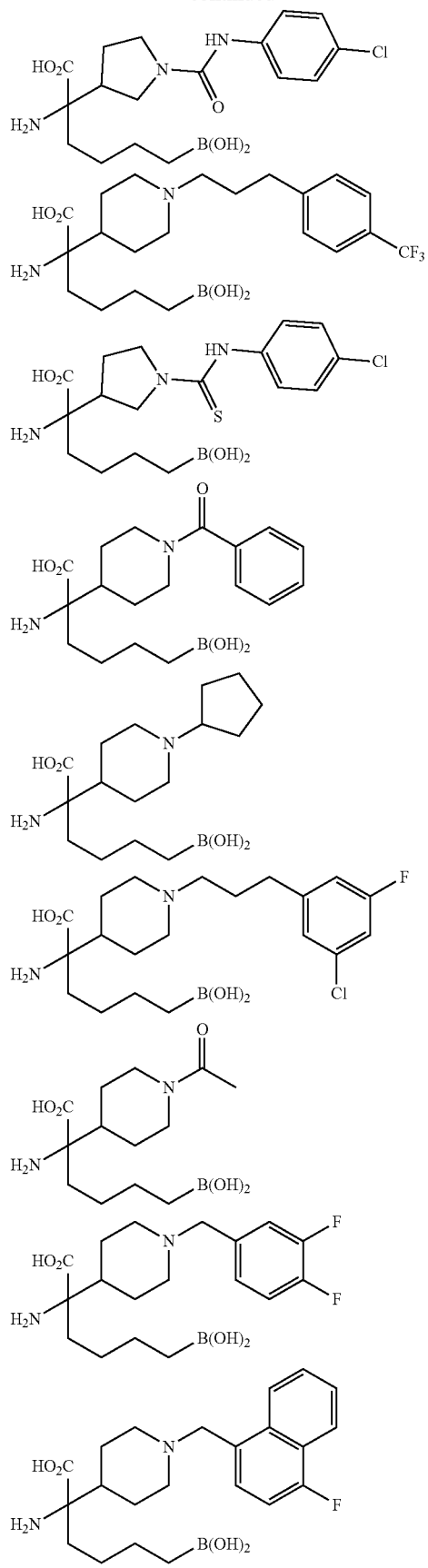
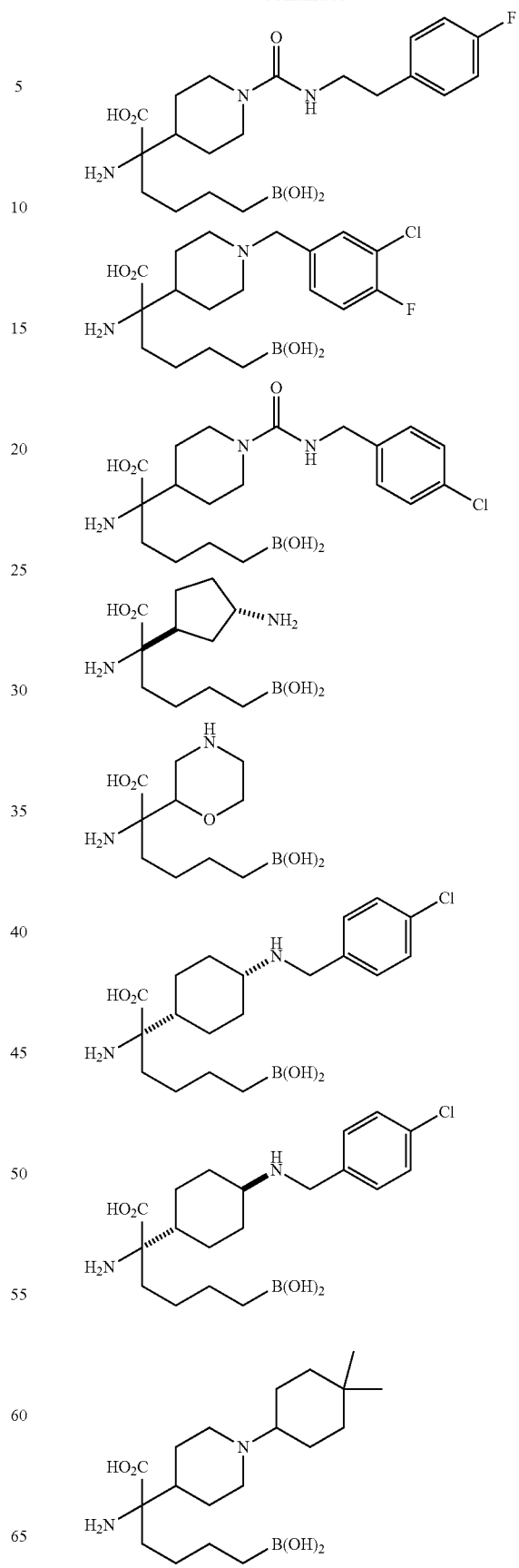

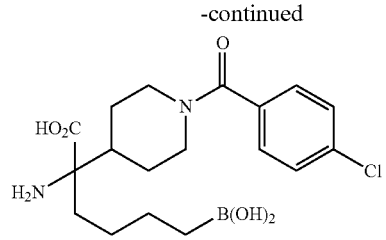
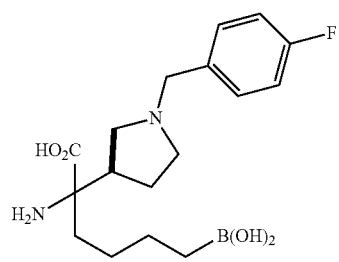
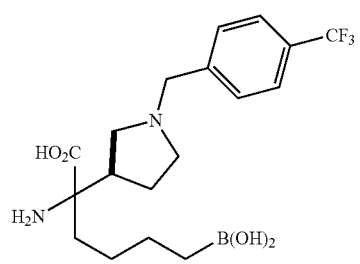
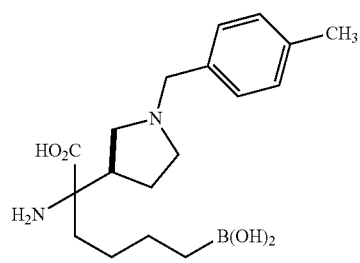
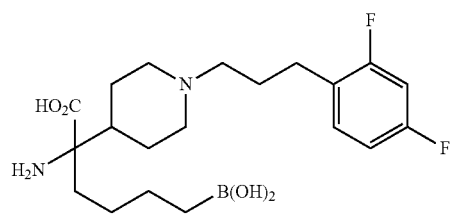
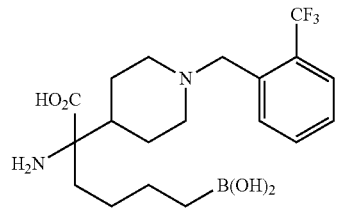
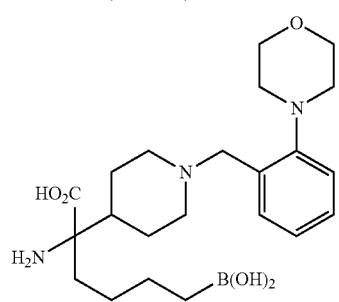
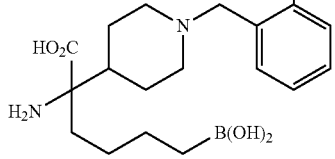
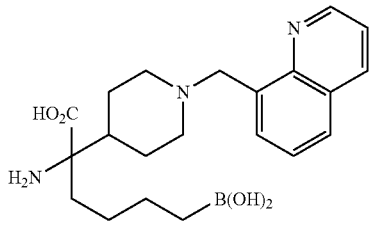
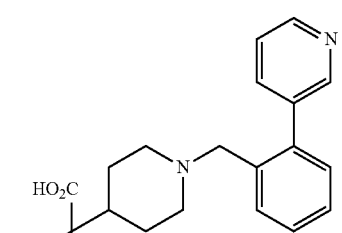
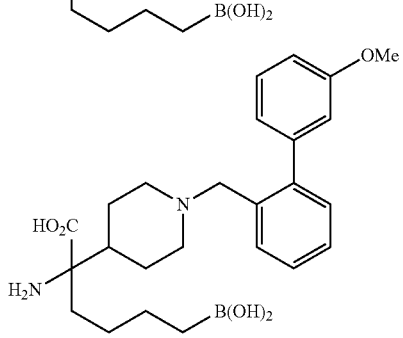
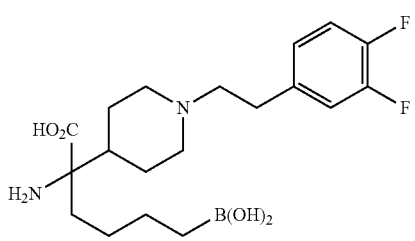
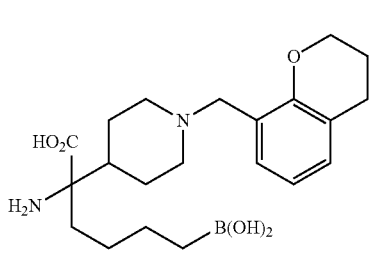

-continued
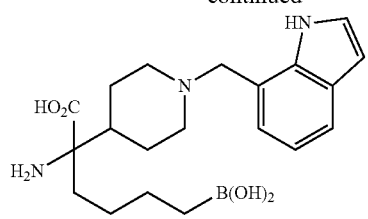
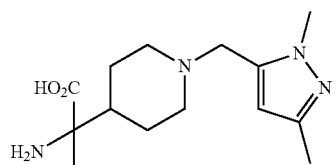
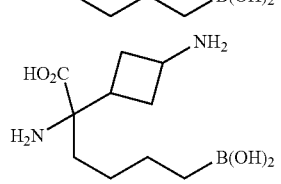
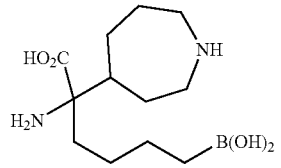
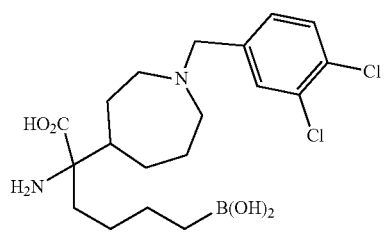
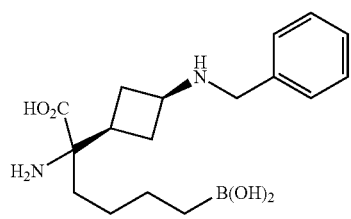
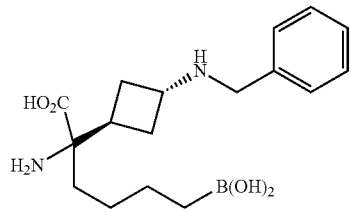
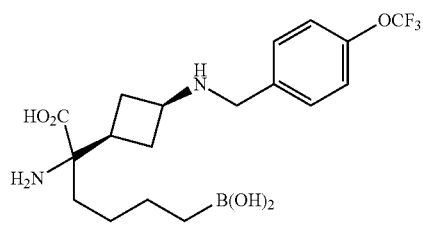
-continued
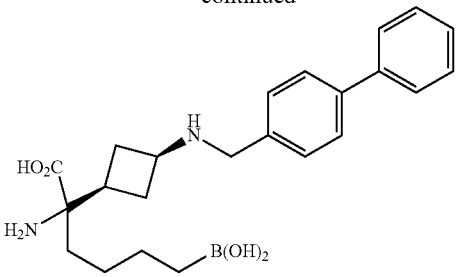
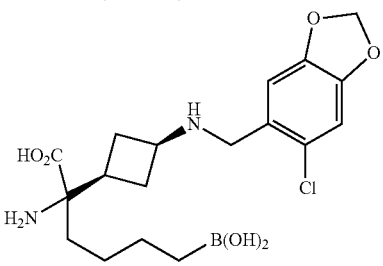
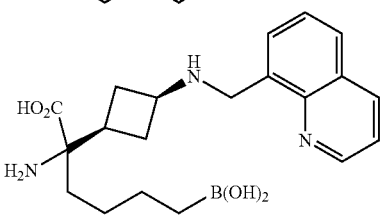
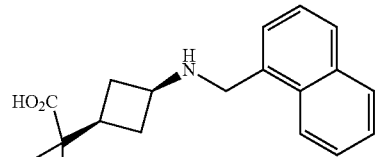
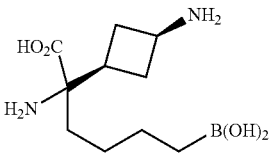
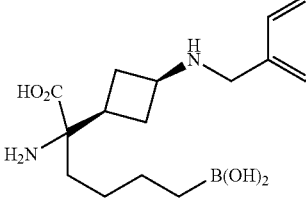
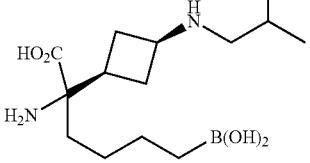
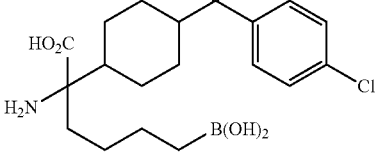

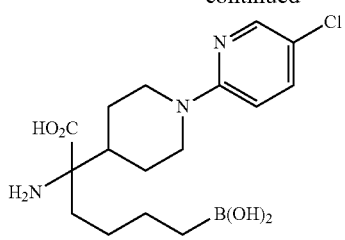
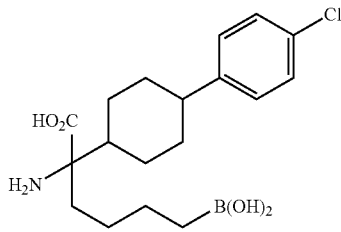
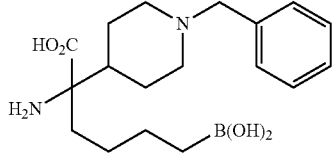
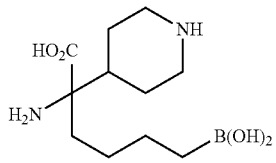
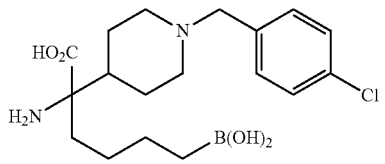
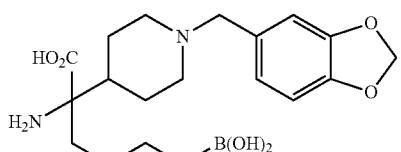
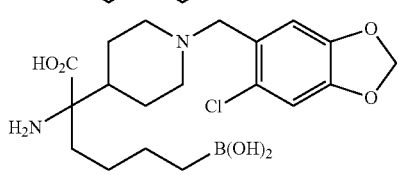
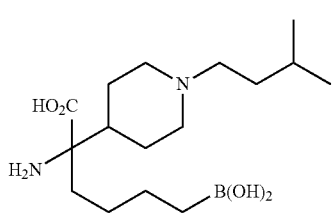
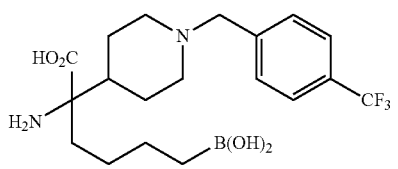
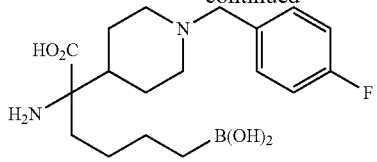
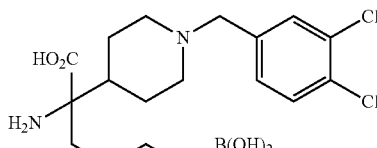
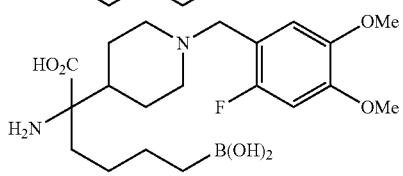
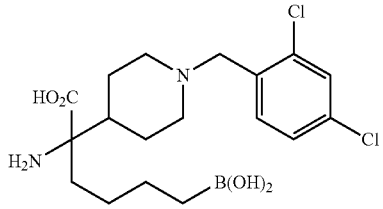
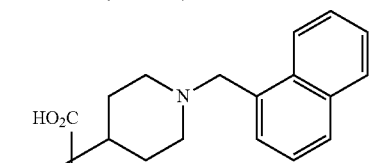
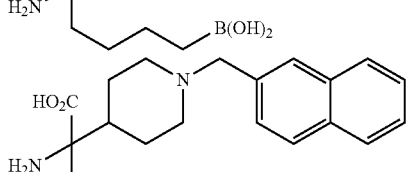
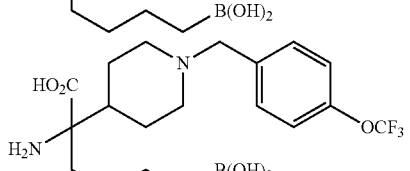
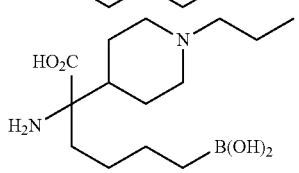
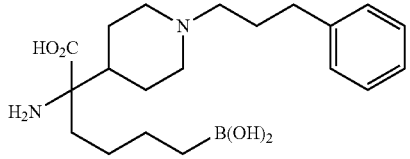
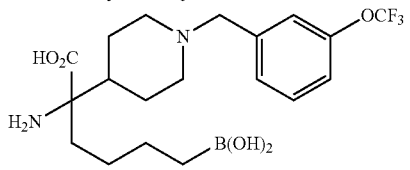

-continued

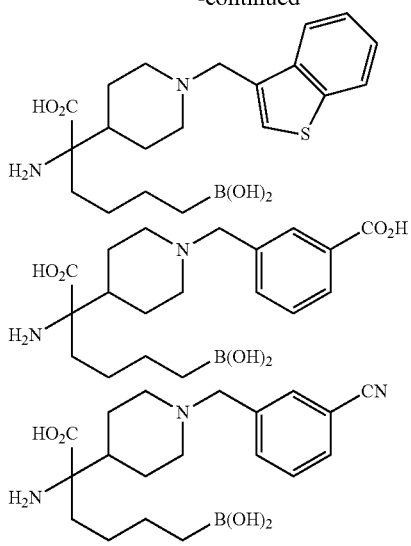

or a pharmaceutically acceptable salt, stereoisomer, or prodrug thereof.

In certain embodiments, the arginase inhibitor used in the methods of the disclosure is:

HOOC—CH(NH$_2$)—Y$_1$—Y$_2$—Y$_3$—Y$_4$—B(OH)$_2$;

wherein each of Y$_1$, Y$_2$, Y$_3$, and Y$_4$ is selected from CH$_2$, S, O, NH, and N-alkyl.

In certain embodiments, the arginase inhibitor used in the methods of the disclosure is a compound of formula IVa or IVb:

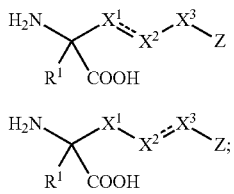

or a stereoisomer, lactone prodrug, or pharmaceutically acceptable salt thereof, wherein: the dashed line represents an optional double bond;

Z is

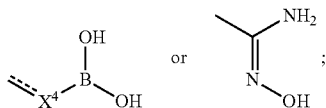

X$^1$ is —(CH$_2$)— or, when said double bond is present between X$^1$ and X$^2$, X$^1$ is —(CH)—;

X$^2$ is —(CH$_2$)— or —(NR$^2$)—, or, when said double bond is present between X$^1$ and X$^2$ or between X$^2$ and X$^3$, X$^2$ is —(CH)— or N;

X$^3$ is —(CH$_2$)—, a heteroatom moiety selected from of —S—, —O— and —(NR$^2$)— or, when said double bond is present between X$^2$ and X$^3$ or between X$^3$ and V, X$^3$ is —(CH)— or N;

X$^4$ is —(CH$_2$)— or, when said double bond is present between X$^3$ and X$^4$, X$^4$ is —(CH)— and is in the trans configuration;

provided that not more than one of X$^2$ and X$^3$ is said —(NR$^2$)— or said heteroatom moiety;

provided that X$^3$ is —(NR$^2$)— when Z is

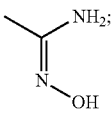

provided that there are no more than two double bonds between X$^1$, X$^2$, X$^3$, X$^4$ and no two double bonds share a common carbon atom;

R$^1$ is a monovalent moiety other than H; or R$^1$ and said α-carboxylate, when taken together, form a lactone; and R$^2$ is, independently, H, methyl, or ethyl.

In certain embodiments, the arginase inhibitor used in the methods of the disclosure is a compound of formula V:

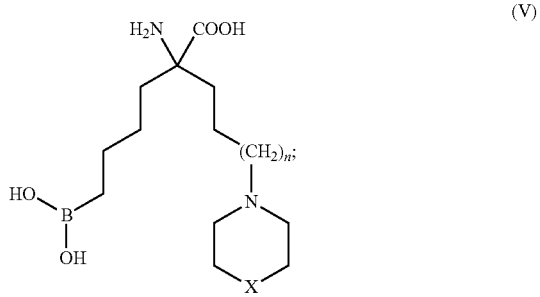

wherein:

n is 0, 1, or 2;

X is NR$^5$, CR$^6$R$^7$, O, S, S(=O) or S(O)$_2$;

R$^7$ is H, OH, OR$^8$, CN or NR$^8$R$^9$; and

R$^5$, R$^6$, R$^8$ and R$^9$ are independently H, (C$_1$-C$_6$)alkyl, aryl, heteroaryl, aryl(C$_1$-C$_6$)alkyl, heteroaryl(C$_1$-C$_6$)alkyl, —C(=O)(C$_1$-C$_6$)alkyl, —C(=O)(aryl), —C(=O)(heteroaryl), —SO$_2$(C$_1$-C$_6$)alkyl, —SO$_2$(aryl), —SO$_2$(heteroaryl), —CONH(C$_1$-C$_6$)alkyl, —CONH(aryl), or —CONH(heteroaryl);

or a derivative thereof, or a salt thereof, e.g., a pharmaceutically acceptable salt thereof;

In certain embodiments, the arginase inhibitor has the structure of formula (VI):

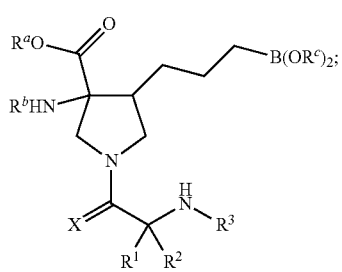

or a pharmaceutically acceptable salt or prodrug thereof; wherein:

R$^a$ is H or is selected from optionally substituted alkyl, alkenyl, alkynyl, cycloalkyl, heterocycloalkyl, (cycloalkyl)alkyl, (heterocycloalkyl)alkyl, aryl, heteroaryl, aralkyl, and heteroaralkyl;

$R^b$ is H or is selected from optionally substituted alkyl, alkenyl, alkynyl, acyl, —C(O)O(alkyl), and —C(O)O(aryl);

each $R^c$ is independently selected from H or alkyl, or two occurrences of $R^c$ are taken together with the intervening —O—B—O— atoms to form an optionally substituted boron-containing ring;

X is O or S;

$R^1$ and $R^2$ are each independently selected from H and optionally substituted alkyl, alkenyl, alkynyl, cycloalkyl, (cycloalkyl)alkyl, heterocycloalkyl, (heterocycloalkyl)alkyl, aryl, heteroaryl, aralkyl, and heteroaralkyl; or $R^1$ and $R^2$ are taken together with the intervening atoms to form an optionally substituted 5- to 7-membered ring; and $R^3$ is H or optionally substituted alkyl;

or $R^1$ and $R^3$ are taken together with the intervening atoms to form an optionally substituted 5- to 7-membered ring;

wherein the compound is not:

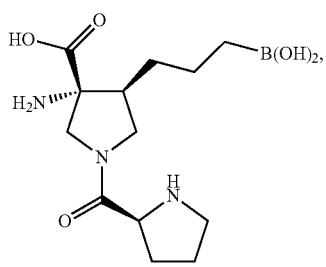

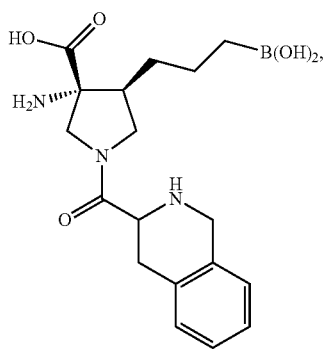

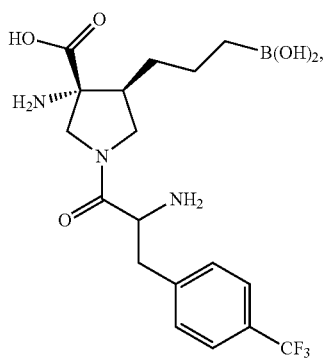

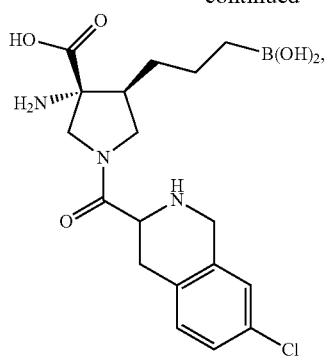

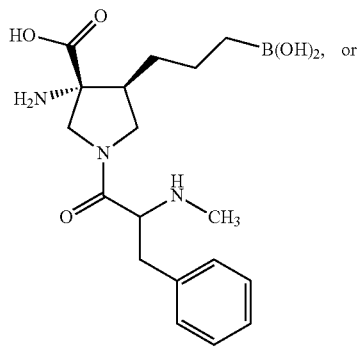

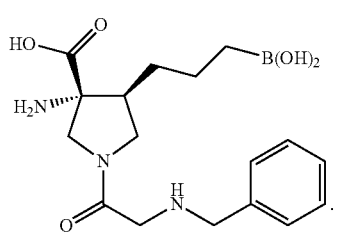 [SMILES: N[C@@]1(C(=O)O)CN(C(=O)CNCc2ccccc2)C[C@@H]1CCCB(O)O]

In certain embodiments, the compound of formula (VI) has a structure of formula (VIa):

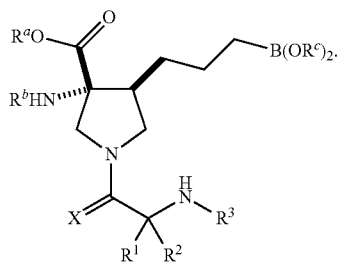

(VIa)

In certain embodiments, the compound of formula (I) has a structure of formula (VIb):

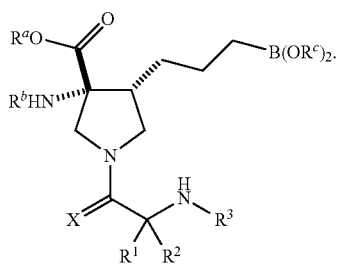
(VIb)

In certain embodiments, the compound of formula (VI) has a structure of formula (VIc):

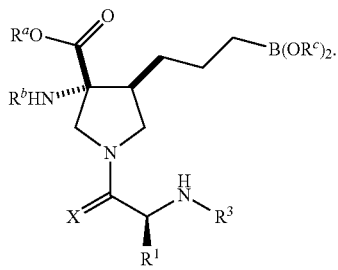
(VIc)

In certain embodiments, the compound of formula (VI) has a structure of formula (VId):

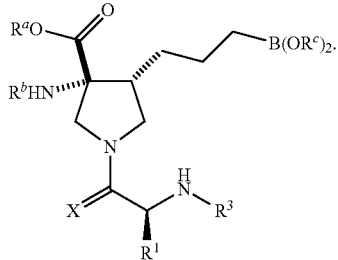
(VId)

In certain embodiments, the compound of formula (VI) has a structure of formula (VIe):

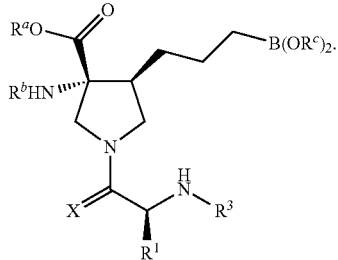
(Ie)

In certain embodiments, the compound of formula (VI) has a structure of formula (VIf):

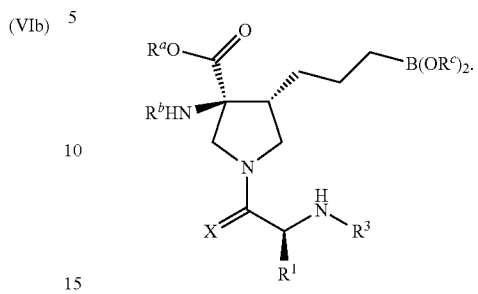
(If)

In certain embodiments, the compound of formula (I) has a structure of formula (Ig):

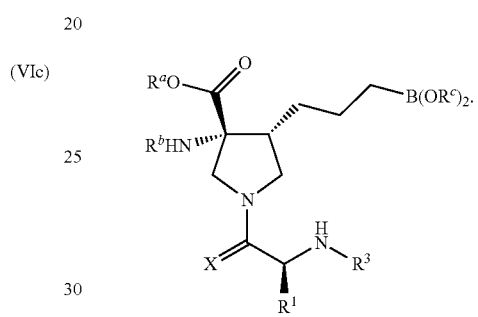
(VIg)

In certain embodiments, the compound of formula (I) has a structure of formula (VIh):

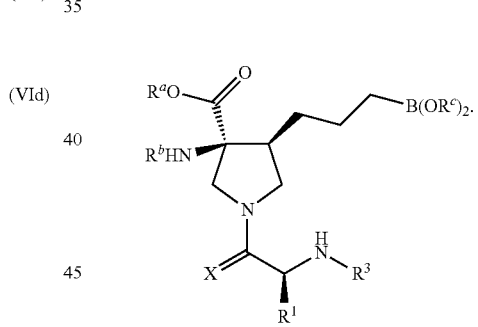
(VIh)

In certain embodiments of any of formulae (VI), (VIa), and (VIb), $R^2$ is H.

In certain embodiments of any of the foregoing formulae, $R^a$ is H or optionally substituted alkyl. In certain preferred embodiments, $R^a$ is H.

In certain embodiments of any of the foregoing formulae, $R^b$ is H or optionally substituted alkyl or acyl. In certain preferred embodiments, $R^b$ is H.

In certain embodiments of any of the foregoing formulae, $R^c$ is H for each occurrence.

In certain embodiments of any of the foregoing formulae, two occurrences of $R^c$ are taken together to form an optionally substituted dioxaborolane, dioxaborolanone, dioxaborolandione, dioxaborinane, dioxaborinanone, or dioxaborinandione.

In certain embodiments of any of the foregoing formulae, X is O.

In certain embodiments of any of the foregoing formulae, if $R^1$ is H, then $R^3$ is not benzyl.

In certain embodiments of any of the foregoing formulae, $R^1$ is H.

In certain embodiments of any of the foregoing formulae, if $R^1$ is benzyl, then $R^3$ is not methyl.

In certain embodiments, $R^1$ is optionally substituted aralkyl, heteroaralkyl, (cycloalkyl)alkyl, or (heterocycloalkyl)alkyl.

In certain embodiments, $R^1$ is optionally substituted aralkyl or heteroaralkyl.

In certain embodiments of the compound of formula VIh, $R^1$ is —$CF_3$. In some such embodiments, X is O. In other such embodiments, X is O and $R^3$ is H. In some such embodiments, X is O, $R^3$ is H and $R^c$ is H. In some such embodiments, X is O, $R^3$ is H and $R^c$, $R^a$ and $R^b$ are H.

In certain embodiments of the compound of formula VIh, $R^3$ is —$(CH_2)_3NH_2$. In some such embodiments, X is O. In other such embodiments, X is O and $R^3$ is H. In some such embodiments, X is O, $R^3$ is H and $R^c$ is H. In some such embodiments, X is O, $R^3$ is H and $R^c$, $R^a$ and $R^b$ are H.

In certain embodiments of the compound of formula VIh, $R^1$ is benzyl. In some such embodiments, X is O. In other such embodiments, X is O and $R^3$ is H. In some such embodiments, X is O, $R^3$ is H and $R^c$ is H. In some such embodiments, X is O, $R^3$ is H and $R^c$, $R^a$ and $R^b$ are H.

In certain embodiments of the compound of formula VIh, $R^1$ is —$CH_3$. In some such embodiments, X is O. In other such embodiments, X is O and $R^3$ is H. In some such embodiments, X is O, $R^3$ is H and $R^c$ is H. In some such embodiments, X is O, $R^3$ is H and $R^c$, $R^a$ and $R^b$ are H.

In certain embodiments of the compound of formula VIh, $R^1$ is —$CH_2OH$. In some such embodiments, X is O. In other such embodiments, X is O and $R^3$ is H. In some such embodiments, X is O, $R^3$ is H and $R^c$ is H. In some such embodiments, X is O, $R^3$ is H and $R^c$, $R^a$ and $R^b$ are H.

In certain embodiments of the compound of formula VIh, $R^1$ is H. In some such embodiments, X is O. In other such embodiments, X is O and $R^3$ is H. In some such embodiments, X is O, $R^3$ is H and $R^c$ is H. In some such embodiments, X is O, $R^3$ is H and $R^c$, $R^a$ and $R^b$ are H.

In certain embodiments, $R^1$ is benzyl.

In other certain such embodiments, $R^1$ is not benzyl substituted by —CF3.

In yet other certain such embodiments, $R^1$ is heteroaralkyl, such as —CH2-(1H-imidazol-4-yl).

In certain embodiments of any of the foregoing formulae $R^1$ is optionally substituted alkyl, alkenyl, or alkynyl.

In certain such embodiments, $R^1$ is alkyl, optionally substituted by one or more substituents independently selected from hydroxy, halo, haloalkyl, alkoxy, —SH, —S-(alkyl), —SeH, —Se-(alkyl), aryl, heteroaryl, cycloalkyl, heterocycloalkyl, amino, carboxylic acid, ester, guanidino, and amido.

In certain such embodiments, $R^1$ is alkyl, optionally substituted by one or more substituents independently selected from hydroxy, halo, haloalkyl, alkoxy, —SH, —S-(alkyl), —SeH, —Se-(alkyl), heteroaryl, cycloalkyl, heterocycloalkyl, amino, carboxylic acid, ester, guanidino, and amido.

In certain such embodiments, $R^1$ is alkyl, optionally substituted by one or more substituents independently selected from hydroxy, alkoxy, haloalkyl, and —S-(alkyl).

In certain embodiments, $R^1$ is selected from optionally substituted cycloalkyl, heterocycloalkyl, aryl, and heteroaryl.

In certain embodiments, $R^1$ is an amino acid side chain of Arg, His, Lys, Asp, Glu, Ser, Thr, Asn, Gln, Cys, Sec, Gly, Ala, Val, Ile, Leu, Met, Phe, Tyr, or Trp.

In certain embodiments, $R^1$ and $R^2$ are taken together with the intervening atoms to form an optionally substituted 5- to 7-membered ring.

In certain embodiments, $R^1$ and $R^2$ are taken together with the intervening atoms to form an optionally substituted 3- to 7-membered ring, such as a 3-membered ring.

In certain embodiments, $R^3$ is H.

In certain embodiments, $R^1$ and $R^3$ are taken together with the intervening atoms to form a substituted 5-membered ring.

In certain embodiments, $R^1$ and $R^3$ are taken together with the intervening atoms to form an optionally substituted 6- or 7-membered ring.

In certain embodiments, $R^1$ and $R^3$, taken together with the intervening atoms, do not form a tetrahydroisoquinolinyl ring, e.g.,

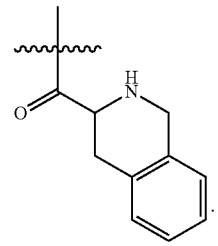 [SMILES: *C(=O)C1Cc2ccccc2CN1]

In certain embodiments, the compound of formula (VI) is not:

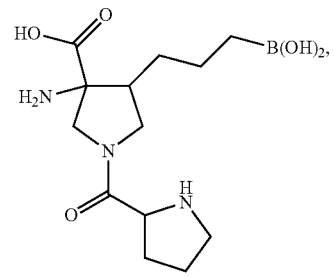

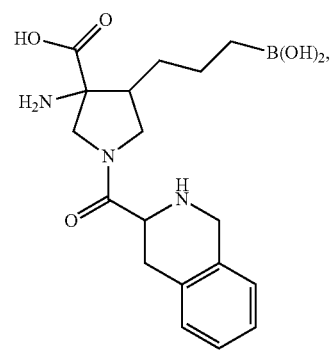

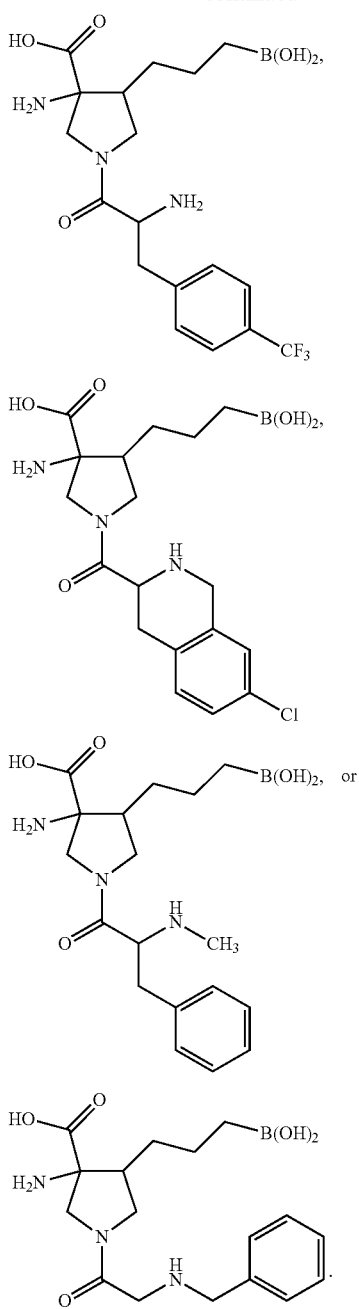
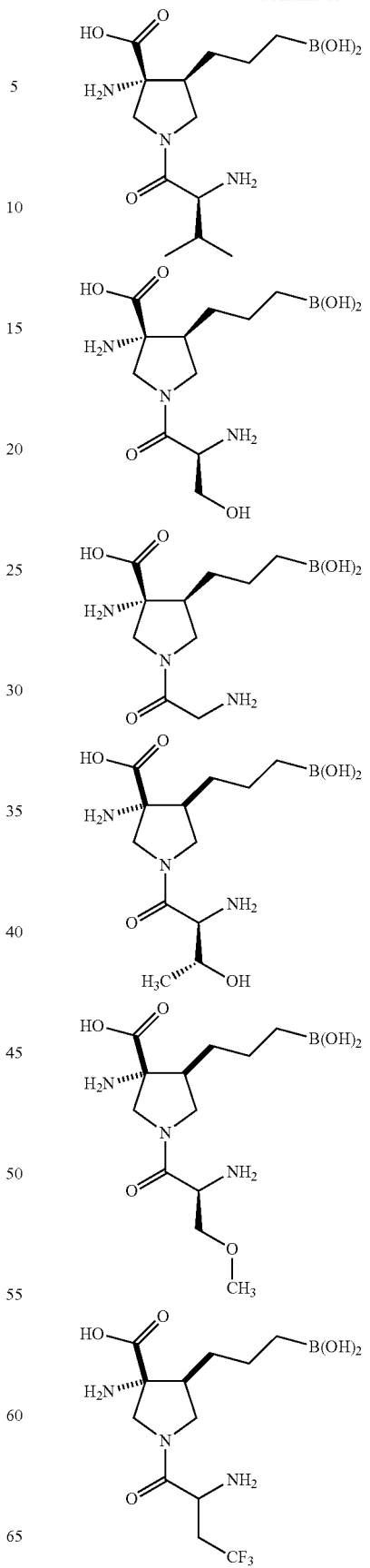
In certain embodiments, the compound of the disclosure has a structure selected from:
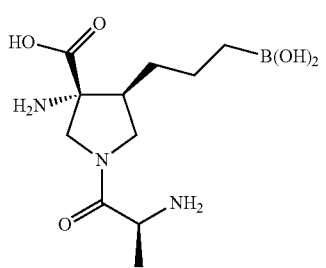

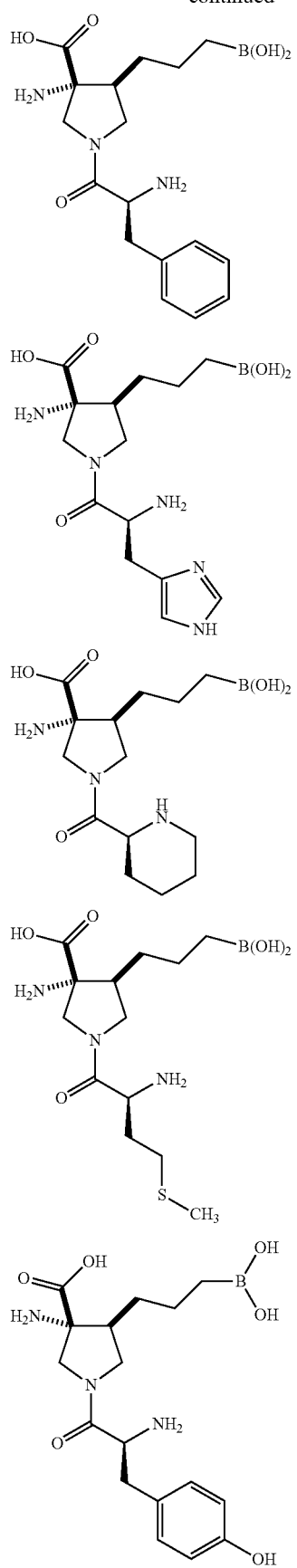
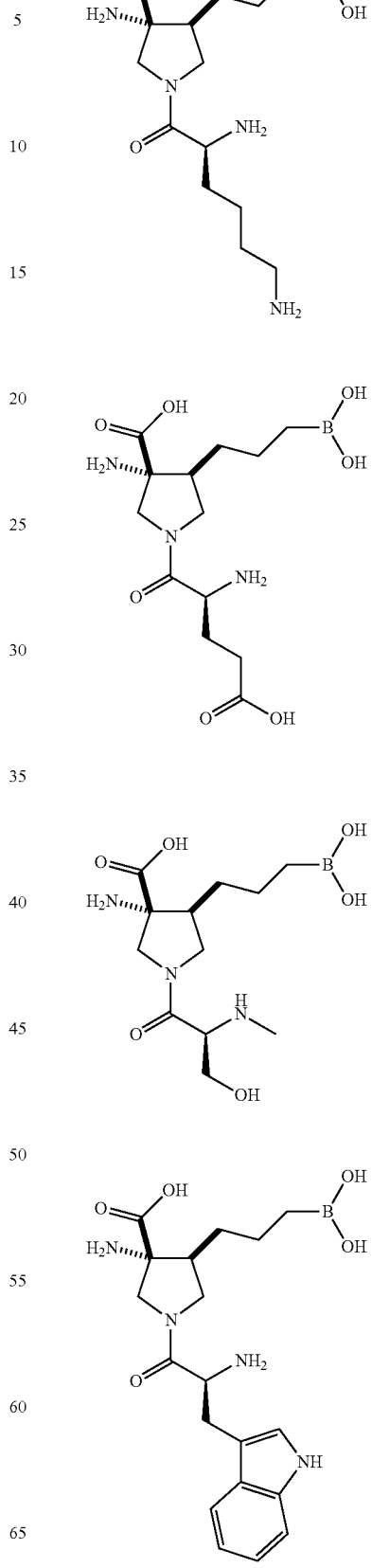

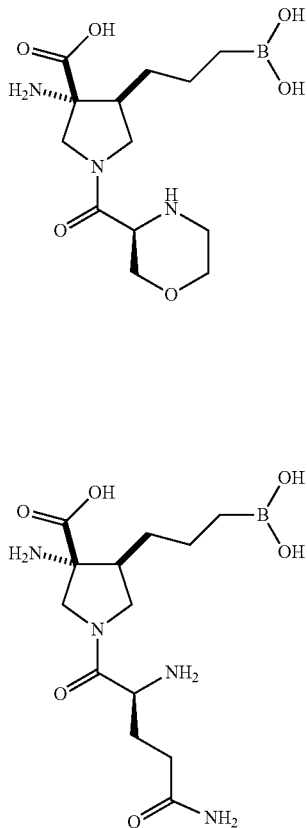

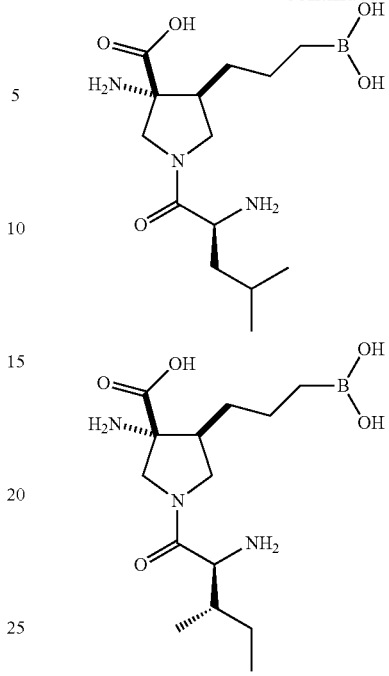

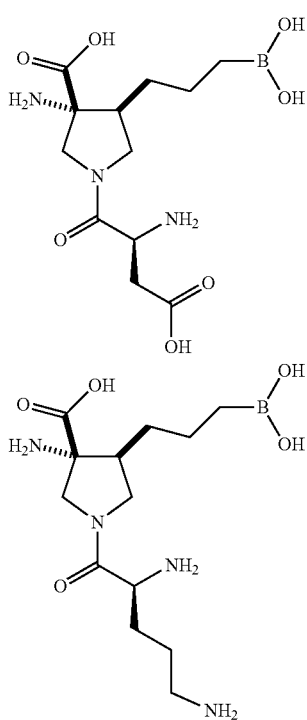

or a pharmaceutically acceptable salt or prodrug thereof.

In certain embodiments, the compound may be a prodrug, e.g., wherein a hydroxyl in the parent compound is presented as an ester or a carbonate, a carboxylic acid present in the parent compound is presented as an ester, or an amino group is presented as an amide. In certain such embodiments, the prodrug is metabolized to the active parent compound in vivo (e.g., the ester is hydrolyzed to the corresponding hydroxyl or carboxylic acid).

In certain embodiments, the boronic acid may exist in the form of a cyclic or linear anhydride. In certain embodiments, the boronic acid exists in the form of a 6-membered ring anhydride, and is also known as a boroxine.

In certain embodiments, arginase inhibitor compounds of the disclosure may be racemic. In certain embodiments, arginase inhibitor compounds of the disclosure may be enriched in one enantiomer. For example, a compound of the disclosure may have greater than 30% ee, 40% ee, 50% ee, 60% ee, 70% ee, 80% ee, 90% ee, or even 95% or greater ee.

The compounds of the invention have more than one stereocenter. Accordingly, the compounds of the disclosure may be enriched in one or more diastereomers. For example, a compound of the disclosure may have greater than 30% de, 40% de, 50% de, 60% de, 70% de, 80% de, 90% de, or even 95% or greater de. In certain embodiments, the compounds of the disclosure have substantially one isomeric configuration at one or more stereogenic centers, and have multiple isomeric configurations at the remaining stereogenic centers.

In certain embodiments, the enantiomeric excess of the stereocenter bearing IV is at least 40% ee, 50% ee, 60% ee, 70% ee, 80% ee, 90% ee, 92% ee, 94% ee, 95% ee, 96% ee, 98% ee or greater ee.

As used herein, single bonds drawn without stereochemistry do not indicate the stereochemistry of the compound. The compound of formula (VI) provides an example of a compound for which no stereochemistry is indicated.

As used herein, hashed or bolded non-wedge bonds indicate relative, but not absolute, stereochemical configuration (e.g., do not distinguish between enantiomers of a given diastereomer). For example, in formula (VIa),

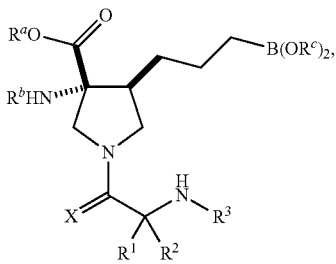

(VIa)

the bold, non-wedge bonds indicate that the —CO$_2$R$^a$ group and the (CH$_2$)$_3$B(OR$^c$)$_2$ group are configured to be cis to one another, but the bold, non-wedge bonds do not represent the absolute (i.e., R or S) configuration of the compound.

As used herein, hashed or bolded wedge bonds indicate absolute stereochemical configuration. For example, in formula (Ic),

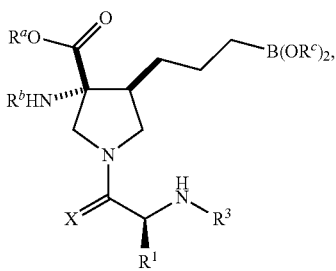

(VIc)

the bold, wedge bond indicates the absolute configuration of the stereocenter to which it is attached, while the bold, non-wedge bonds indicate that the —CO$_2$R$^a$ group and the (CH$_2$)$_3$B(OR$^c$)$_2$ group are configured to be cis to one another, but do not indicate the absolute configuration of those stereocenters. Therefore, the compound of formula (VIc) represents two isomers in total:

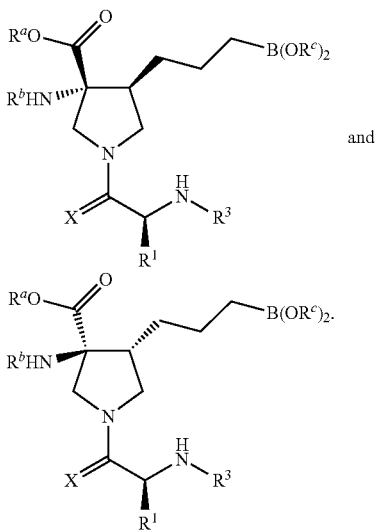

and

Exemplary arginase inhibitors that may be used in the methods of the disclosure described herein include the compounds described in Appendix A, submitted herewith and hereby incorporated by reference.

In certain embodiments, the arginase inhibitor may be a prodrug of a compound of any of the formulae disclosed herein, e.g., wherein a hydroxyl in the parent compound is presented as an ester or a carbonate, or carboxylic acid present in the parent compound is presented as an ester. In certain such embodiments, the prodrug is metabolized to the active parent compound in vivo (e.g., the ester is hydrolyzed to the corresponding hydroxyl or carboxylic acid).

In certain embodiments, arginase inhibitor compounds of the disclosure may be racemic. In certain embodiments, arginase inhibitor compounds of the disclosure may be enriched in one enantiomer. For example, a compound of the disclosure may have greater than 30% ee, 40% ee, 50% ee, 60% ee, 70% ee, 80% ee, 90% ee, or even 95% or greater ee. In certain embodiments, compounds of the disclosure may have more than one stereocenter. In certain such embodiments, compounds of the disclosure may be enriched in one or more diastereomer. For example, a compound of the disclosure may have greater than 30% de, 40% de, 50% de, 60% de, 70% de, 80% de, 90% de, or even 95% or greater de.

In certain embodiments, a therapeutic preparation of the arginase inhibitor may be enriched to provide predominantly one enantiomer of a compound (e.g., of a formula described herein). An enantiomerically enriched mixture may comprise, for example, at least 60 mol percent of one enantiomer, or more preferably at least 75, 90, 95, or even 99 mol percent. In certain embodiments, the arginase inhibitor compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a arginase inhibitor composition or compound mixture contains 98 grams of a first enantiomer and 2 grams of a second enantiomer, it would be said to contain 98 mol percent of the first enantiomer and only 2% of the second enantiomer.

In certain embodiments, a therapeutic preparation may be enriched to provide predominantly one diastereomer of an arginase inhibitor compound (e.g., an arginase inhibitor having a formula disclosed herein). A diastereomerically enriched mixture may comprise, for example, at least 60 mol percent of one diastereomer, or more preferably at least 75, 90, 95, or even 99 mol percent.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$ and $^{131}$I. For example, one or more protium ($^1$H) atoms in a compound of the present disclosure can be replaced by deuterium atoms (e.g., one or more hydrogen atoms of a C$_{1-6}$ alkyl group of Formula (I) can be enriched with deuterium atoms, e.g., —CD$_3$ being substituted for a more common —C($^1$H)$_3$ methyl group).

One or more constituent atoms of the compounds presented herein can be replaced or substituted with isotopes of the atoms in natural or non-natural abundance. In some embodiments, the compound includes at least one hydrogen that is enriched for deuterium atoms, i.e., the compound contains deuterium atoms in excess of the natural abundance of deuterium on Earth. For example, one or more hydrogen atoms in a compound presented herein can be enriched for deuterium (e.g., one or more protium atoms of a $C_{1-6}$ alkyl group can be replaced by deuterium atoms, such as —$CD_3$ being substituted for a more common —$C(^{1}H)_3$ methyl group). In some embodiments, the compound is enriched for two or more deuterium atoms. In some embodiments, the compound includes 1, 2, 3, 4, 5, 6, 7, 8, 9, 10, 11, 12, 13, 14, 15, 16, 17, 18, 19, 20, 21, 22, 23, or 24 deuterium atoms. In some embodiments, all of the hydrogen atoms in a compound can be enriched for deuterium atoms instead of protium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes, such as deuterium for protium, may afford certain therapeutic advantages resulting from greater metabolic stability, for example, increased in vivo half-life or reduced dosage requirements, and hence may be preferred in some circumstances. (see, e.g., A. Kerekes et. al. *J. Med. Chem.* 2011, 54, 201-210; R. Xu et. al. *J. Label Compd. Radiopharm.* 2015, 58, 308-312).

The radionuclide that is incorporated in the instant radio-labeled compounds will depend on the specific application of that radio-labeled compound. For example, for in vitro PI3K labeling and competition assays, compounds that incorporate $^{3}H$, $^{14}C$, $^{82}Br$, $^{125}I$, $^{131}I$ or $^{35}S$ can be useful. For radio-imaging applications, $^{11}C$, $^{18}F$, $^{125}I$, $^{123}I$, $^{124}I$, $^{131}I$, $^{75}Br$, $^{76}Br$, or $^{77}Br$ can be useful.

It is understood that a "radio-labeled" or "labeled compound" is a compound that has incorporated at least one radionuclide. In some embodiments, the radionuclide is selected from $^{3}H$, $^{14}C$, $^{125}I$, $^{35}S$ and $^{82}Br$.

The present disclosure can further include synthetic methods for incorporating radio-isotopes into compounds of the disclosure. Synthetic methods for incorporating radio-isotopes into organic compounds are well known in the art, and one of ordinary skill in the art will readily recognize methods applicable for the compounds of disclosure.

Therapeutic Methods

In some aspects, provided herein are therapeutic methods related to treating or preventing a disease in a subject by administering to the subject an arginase inhibitor disclosed herein and a composition comprising immune cells disclosed herein. In some embodiments, the subject is administered about $1\times10^3$ cells per kg (body weight) to about $1\times10^{20}$ cells per kg (body weight). In some embodiments, at least $1\times10^3$ cells/kg, at least $1\times10^4$ cells/kg, at least $1\times10^6$ cells/kg, at least $1\times10^7$ cells/kg, at least $1\times10^8$ cells/k, at least $1\times10^9$ cells/kg, at least $50\times10^{10}$ cells/kg, at least $1\times10^{11}$ cells/kg, at least $1\times10^{12}$ cells/kg, at least $1\times10^{13}$ cells/kg, at least $1\times10^{14}$ cells/kg, at least $1\times10^{15}$ cells/kg, at least $1\times10^{16}$ cells/kg, at least $1\times10^{17}$ cells/kg, at least $1\times10^{18}$ cells/kg, at least $1\times10^{19}$ cells/kg, or at least $1\times10^{20}$ cells/kg are administered to the subject. The number of immune cells administered to the subject may vary depending on a variety of factors including, but not limited to, the subject's response to immune cell therapy, the subject's medical history, the subject's weight, gender, and/or ethnic background.

In some embodiments, the disease is a viral infection. In some embodiments, the subject may have just undergone a transplantation (e.g., a hematopoietic stem cell transplantation (SCT)). In some embodiments, the subject is immunodeficient.

In some embodiments, the disease is cancer. In certain embodiments, the cancer is Acute Lymphoblastic Leukemia (ALL), Acute Myeloid Leukemia (AML), Adrenocortical Carcinoma, Anal Cancer, Appendix Cancer, Atypical Teratoid/Rhabdoid Tumor, Basal Cell Carcinoma, Bile Duct Cancer, Bladder Cancer, Bone Cancer, Brain Tumor, Astrocytoma, Brain and Spinal Cord Tumor, Brain Stem Glioma, Central Nervous System Atypical Teratoid/Rhabdoid Tumor, Central Nervous System Embryonal Tumors, Breast Cancer, Bronchial Tumors, Burkitt Lymphoma, Carcinoid Tumor, Carcinoma of Unknown Primary, Central Nervous System Cancer, Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma, Ductal Carcinoma In Situ (DCIS), Embryonal Tumors, Endometrial Cancer, Ependymoblastoma, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Fibrous Histiocytoma of Bone, Gallbladder Cancer, Gastric Cancer, Gastrointestinal Carcinoid Tumor, Gastrointestinal Stromal Tumors (GIST), Germ Cell Tumor, Ovarian Germ Cell Tumor, Gestational Trophoblastic Tumor, Glioma, Hairy Cell Leukemia, Head and Neck Cancer, Heart Cancer, Hepatocellular Cancer, Histiocytosis, Langerhans Cell Cancer, Hodgkin Lymphoma, Hypopharyngeal Cancer, Intraocular Melanoma, Islet Cell Tumors, Kaposi Sarcoma, Kidney Cancer, Langerhans Cell Histiocytosis, Laryngeal Cancer, Leukemia, Lip and Oral Cavity Cancer, Liver Cancer, Lobular Carcinoma In Situ (LCIS), Lung Cancer, Lymphoma, AIDS-Related Lymphoma, Macroglobulinemia, Male Breast Cancer, Medulloblastoma, Medulloepithelioma, Melanoma, Merkel Cell Carcinoma, Malignant Mesothelioma, Metastatic Squamous Neck Cancer with Occult Primary, Midline Tract Carcinoma Involving NUT Gene, Mouth Cancer, Multiple Endocrine Neoplasia Syndrome, Multiple Myeloma/Plasma Cell Neoplasm, Mycosis Fungoides, Myelodysplastic Syndrome, Myelodysplastic/Myeloproliferative Neoplasm, Chronic Myelogenous Leukemia (CML), Acute Myeloid Leukemia (AML), Myeloma, Multiple Myeloma, Chronic Myeloproliferative Disorder, Nasal Cavity Cancer, Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip Cancer, Oropharyngeal Cancer, Osteosarcoma, Ovarian Cancer, Pancreatic Cancer, Papillomatosis, Paraganglioma, Paranasal Sinus Cancer, Nasal Cavity Cancer, Parathyroid Cancer, Penile Cancer, Pharyngeal Cancer, Pheochromocytoma, Pineal Parenchymal Tumors of Intermediate Differentiation, Pineoblastoma, Pituitary Tumor, Plasma Cell Neoplasm, Pleuropulmonary Blastoma, Breast Cancer, Primary Central Nervous System (CNS) Lymphoma, Prostate Cancer, Rectal Cancer, Renal Cell Cancer, Clear cell renal cell carcinoma, Renal Pelvis Cancer, Ureter Cancer, Transitional Cell Cancer, Retinoblastoma, Rhabdomyosarcoma, Salivary Gland Cancer, Sarcoma, Sézary Syndrome, Skin Cancer, Small Cell Lung Cancer, Small Intestine Cancer, Soft Tissue Sarcoma, Squamous Cell Carcinoma, Squamous Neck Cancer with Occult Primary, Squamous Cell Carcinoma of the Head and Neck (HNSCC), Stomach Cancer, Supratentorial Primitive Neuroectodermal Tumors, T-Cell Lymphoma, Testicular Cancer, Throat Cancer, Thymoma, Thymic Carcinoma, Thyroid Cancer, Transitional Cell Cancer of the Renal Pelvis and Ureter, Triple Negative Breast Cancer (TNBC), Gestational Trophoblastic Tumor, Unknown Primary, Unusual Cancer of Childhood, Urethral Cancer, Uterine Cancer, Uterine Sarcoma, Waldenström Macroglobulinemia, or Wilms Tumor.

In certain embodiments, the cancer that is treated by the methods of the disclosure is a variety of acute myeloid leukemia (AML), breast cancer, colorectal cancer, chronic myelogenous leukemia (CML), esophageal cancer, gastric cancer, lung cancer, melanoma, non-small cell lung carcinoma (NSCLC), pancreatic cancer, prostate cancer, or renal cancer.

Combination therapy is an important treatment modality in many disease settings, such as cancer. Recent scientific advances have increased our understanding of the pathophysiological processes that underlie these and other complex diseases. This increased understanding has provided impetus to develop new therapeutic approaches using combinations of drugs directed at multiple therapeutic targets to improve treatment response, minimize development of resistance, or minimize adverse events. In settings in which combination therapy provides significant therapeutic advantages, there is growing interest in the development of combinations with new investigational drugs, such as arginase inhibitors.

The methods disclosed herein may further comprise administering an additional agent (e.g., a chemotherapeutic agent or an immune checkpoint inhibitor). In certain embodiments of the disclosure, the additional agent is administered simultaneously with the arginase inhibitor and/or the immune cells. In certain embodiments, the additional agent is administered sequentially with the arginase inhibitor and/or the immune cells.

In some embodiments, the methods for combination therapy in treating or preventing a disease (e.g., cancer) further comprise administering one or more additional chemotherapeutic agents. The chemotherapeutic agent may be aminoglutethimide, amsacrine, anastrozole, asparaginase, AZD5363, Bacillus Calmette-Guérin vaccine (bcg), bicalutamide, bleomycin, bortezomib, buserelin, busulfan, campothecin, capecitabine, carboplatin, carfilzomib, carmustine, chlorambucil, chloroquine, cisplatin, cladribine, clodronate, cobimetinib, colchicine, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, erlotinib, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, nilutamide, nocodazole, octreotide, olaparib, oxaliplatin, paclitaxel, pamidronate, pazopanib, pentostatin, perifosine, plicamycin, pomalidomide, porfimer, procarbazine, raltitrexed, rituximab, rucaparib, selumetinib, sorafenib, streptozocin, sunitinib, suramin, talazoparib, tamoxifen, temozolomide, temsirolimus, teniposide, testosterone, thalidomide, thioguanine, thiotepa, titanocene dichloride, topotecan, trametinib, trastuzumab, tretinoin, veliparib, vinblastine, vincristine, vindesine, or vinorelbine.

In certain embodiments, the chemotherapeutic agent may be abagovomab, adecatumumab, afutuzumab, anatumomab mafenatox, apolizumab, blinatumomab, catumaxomab, durvalumab, epratuzumab, inotuzumab ozogamicin, intelumumab, ipilimumab, isatuximab, lambrolizumab, nivolumab, ocaratuzumab, olatatumab, pembrolizumab, pidilizumab, ticilimumab, samalizumab, or tremelimumab.

In certain embodiments, the chemotherapeutic agent is ipilimumab, nivolumab, pembrolizumab, or pidilizumab.

In certain embodiments, the chemotherapeutic agent is selected from a metabolic enzyme inhibitor, such as glucose transporters, hexokinase, pyruvate kinase M2, lactate dehydrogenase 1 or 2, pyruvate dehydrogenase kinase, fatty acid synthase and glutaminase. In some embodiments, the inhibitor inhibits lactate dehydrogenase 1 or 2, or glutaminase. In certain embodiments, the inhibitor is CB-839.

In some embodiments, the conjointly administered chemotherapeutic agent is an immune-oncology therapeutic, such as epacadostat (incb 24360), CTLA-4, indoleamine 2,3-dioxygenase, and/or PD-1/PD-L1. In certain embodiments, the immune-oncology agent is abagovomab, adecatumumab, afutuzumab, anatumomab mafenatox, apolizumab, blinatumomab, catumaxomab, durvalumab, epratuzumab, indoximod, inotuzumab ozogamicin, intelumumab, ipilimumab, isatuximab, lambrolizumab, nivolumab, ocaratuzumab, olatatumab, pembrolizumab, pidilizumab, ticilimumab, samalizumab, or tremelimumab. In some embodiments, the immune-oncology agent is indoximod, ipilimumab, nivolumab, pembrolizumab, or pidilizumab. In certain embodiments, the immune-oncology agent is ipilimumab.

In certain embodiments, the method of treating or preventing cancer further comprises administering one or more non-chemical methods of cancer treatment, such as radiation therapy, surgery, thermoablation, focused ultrasound therapy, cryotherapy, or a combination of the foregoing.

In some embodiments, the subject is also administered an immune checkpoint inhibitor. Immune checkpoint inhibition broadly refers to inhibiting the checkpoints that cancer cells can produce to prevent or downregulate an immune response. Examples of immune checkpoint proteins include, but are not limited to, CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, HHLA2, butyrophilins, A2aR, and combinations thereof. Immune checkpoint inhibitors can be antibodies or antigen binding fragments thereof that bind to and inhibit an immune checkpoint protein. Examples of immune checkpoint inhibitors include, but are not limited to, nivolumab, pembrolizumab, pidilizumab, AMP-224, AMP-514, STI-A1110, TSR-042, RG-7446, BMS-936559, MEDI-4736, MSB-0020718C, AUR-012 and STI-A1010.

The compositions comprising immune cells, arginase inhibitors, and antibodies disclosed herein may be administered through any route of administration known in the art, including, but not limited to, intravenous or parenteral administration (e.g., intravenous, subcutaneous, or intramuscular), buccal, intranasal, rectal or transdermal administration routes. Arginase inhibitors, compositions comprising immune cells, and antibodies described herein may be co-administered or administered at different times. The compositions comprising immune cells, arginase inhibitors, and antibodies may be administered locally or systemically. In some embodiments, the compositions comprising immune cells, arginase inhibitors, and antibodies disclosed herein are administered locally into a tumor or into the tumor microenvironment.

Pharmaceutical Compositions

In some aspects, the disclosure provides a pharmaceutical composition comprising an arginase inhibitor, such as a compound having a formula disclosed herein or a pharmaceutically acceptable salt thereof, with a pharmaceutically acceptable carrier. In some embodiments, the present disclosure provides a pharmaceutical preparation suitable for use in a human patient, comprising a composition comprising immune cells and an arginase inhibitor, such as a compound of any one of the formulae described herein and one or more pharmaceutically acceptable excipients. In some embodiments, the preparation may further comprise an antibody as disclosed herein. In certain embodiments, the pharmaceutical preparations may be for use in treating or preventing a condition or disease as described herein. In certain embodiments, the pharmaceutical preparations have a low enough pyrogen activity to be suitable for use in a human patient.

The compositions and methods disclosed herein may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the disclosure and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In some embodiments, when such pharmaceutical compositions are for human administration, particularly for invasive routes of administration (i.e., routes, such as injection or implantation, that circumvent transport or diffusion through an epithelial barrier); the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the disclosure. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The combination therapy may comprise administering the compositions and pharmaceutical compositions directly into a tumor present in the subject. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the disclosure, with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this disclosure. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., administration via an implant).

The phrases "parenteral administration" and "administered parenterally" as used herein means modes of administration other than enteral and topical administration, usually by injection (e.g., injection directly into a tumor or into the tumor microenvironment), and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this disclosure, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present disclosure, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the disclosure may be used alone or conjointly administered with another type of therapeutic agent. As used herein, the phrase "conjoint administration" refers to any form of administration of two or more different therapeutic agent such that the second agent is administered while the previously administered therapeutic agent is still effective in the body (e.g., the two agents are simultaneously effective in the patient, which may include synergistic effects of the two agents). For example, the different therapeutic agents can be administered either in the same formulation or in a separate formulation, either concomitantly or sequentially. In certain embodiments, the different therapeutic agents can be administered within one hour, 12 hours, 24 hours, 36 hours, 48 hours, 72 hours, or a week of one another. Thus, an individual who receives such treatment can benefit from a combined effect of different therapeutic agents.

In certain embodiments, conjoint administration of compounds of the disclosure with one or more additional therapeutic agent(s) (e.g., one or more additional chemotherapeutic agent(s)) provides improved efficacy relative to each individual administration of the compound of the disclosure (e.g., compound of formula I, II, or III) or the one or more additional therapeutic agent(s). In certain such embodiments, the conjoint administration provides an additive effect, wherein an additive effect refers to the sum of each of the effects of individual administration of the compound of the disclosure and the one or more additional therapeutic agent(s).

This disclosure includes the use of pharmaceutically acceptable salts of compounds of the disclosure in the compositions and methods of the present disclosure. The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I, II or III. As another example, the salt may comprise less than one inorganic or organic acid molecule per molecule of base, such as two molecules of compound of Formula I, II, or III per molecule of tartaric acid.

In further embodiments, contemplated salts of the disclosure include, but are not limited to, alkyl, dialkyl, trialkyl or tetra-alkyl ammonium salts. In certain embodiments, contemplated salts of the disclosure include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the disclosure include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

5. EXAMPLES

Example 1

Administration of Arginase Inhibitors with Adoptive Immunotherapy

In order to test the effect of arginase inhibitors and adoptive immunotherapy on cancer progression, mice were inoculated with B16.F10 cells to generate a tumor. Approximately $1\times10^6$ cells were implanted in C57.Bl/6 mice. Mice were then treated with non-myeloablative chemotherapy (Cyclophosphamide 250 mg/kg and Fludarabine 50 mg/kg). Cyclophosphamide and Fludarabine were dosed via intraperitoneal injection on day 7 (FIG. 1A, orange arrow). Pmel-1 CD8 T cells ($1\times10^6$) were intravenously transferred on day 8 (FIG. 1A, blue arrow). Recombinant human IL-2 (200,000 UI) was dosed via intraperitoneal injection twice a day on days 8, 9, 10 in mice receiving adoptive immunotherapy. Arginase inhibitor was dosed 100 mg/kg twice a day. FIG. 1B shows tumor volume over 25 days in mice who received combination T cell therapy and arginase inhibitor treatment, versus mice who only received adoptive T cell therapy. Tumor volume in mice receiving combination therapy alone showed a slower tumor progression over time. Survival curves can be seen in FIG. 1C. P value is 0.0137, and was calculated by Mantel-Cox test. (N=9-10 per group).

Example 2

Inhibition of Arginase Blocks Myeloid Cell-Mediated Immune Suppression in the Tumor Microenvironment Myeloid cells in the tumor microenvironment (TME) are associated with poor prognosis across multiple types of cancer, including lung, colorectal, and breast. Tumor infiltrating myeloid cells contribute to an immunosuppressive TME through multiple mechanisms, constraining anti-tumor immunity and hindering immunotherapy. Agents that aim to block myeloid cell-mediated immunosuppression are currently in pre-clinical and clinical development, however there are no approved therapies specifically directed against tumor-associated myeloid cells.

The major populations of tumor infiltrating myeloid cells include tumor-associated macrophages (TAMs), myeloid-derived suppressor cells (MDSCs), and granulocytes. A feature common to all of these immunosuppressive cells is their expression of the enzyme arginase 1 (Arg1). Arg1 catalyzes hydrolysis of the amino acid L-arginine to produce urea and L-ornithine, thereby depleting extracellular L-arginine. T cells are auxotrophic for L-arginine, requiring the amino acid for the rapid and successive rounds of proliferation that follow T cell antigen receptor (TCR)-dependent activation of effector cells. In some inflammatory settings, myeloid-mediated arginine depletion is essential for suppressing excessive T cell proliferation. Blocking Arg1 activity in the context of cancer could therefore shift the balance of L-arginine metabolism to favor lymphocyte proliferation. Pharmacological inhibition of Arg1 is a compelling therapeutic strategy for the treatment of cancer.

In T cell co-cultures, arginase inhibition reversed myeloid cell-mediated immunosuppression and restored T cell proliferation. In murine syngeneic tumor models, arginase inhibitor shifted the tumor immune landscape toward a pro-inflammatory TME, resulting in tumor growth inhibition. Arginase inhibitor augmented the efficacy of other anti-cancer agents, including gemcitabine, anti-programmed death ligand 1 (PD-L1) antibody, adoptive T cell therapy, and adoptive NK cell therapy, to inhibit tumor growth. The therapeutic potential of targeting Arg1 was further supported in a screen of cancer patient samples that revealed an abundance of Arg1-expressing myeloid cells in tumors and high amounts of Arg1 in plasma.

Methods

Chemical compounds. An arginase inhibitor (see WO 2017/075363, compound 13, hereby incorporated by reference) was synthesized at Calithera Biosciences and dissolved in 100% DMSO for biochemical assays or in Milli-Q water (Millipore, Billerica, Mass.) for cell-based assays and in vivo studies. No endotoxin contamination of the arginase inhibitor preparations was observed.

Flow cytometry antibodies. The following anti-mouse antibodies were used for flow cytometry: CD45-V450 (30F11), CD45-BV510 (30F11), CD45-BV605 (30F11), CD8-BV510 (53-6.7), CD25-BV421 ($PC_{61}$), CD25-BV605 ($PC_{61}$) from BD Biosciences (San Jose, Calif.); CD3-PerCP-eFluor710 (17A2), CD45-PE-Cy7 (30F11), NKp46-eFluor660 (29A1.4), CD11b-PE-Cy7 (M1/70), CD68-PE-Cy7 (FA-11) from eBioscience (Thermo Fisher Scientific, Waltham, Mass.); CD3-PE (17A2); CD68-BV421 (FA-11), CD206-AlexaFluor488 ($C068C_2$), CD11b-PerCP-Cy5.5 (M1/70), CD11b-BV605 (M1/70) from BioLegend (San Diego, Calif.); CD11b-PE (M1/70) from Stemcell Technologies (Vancouver, Canada); and Arg1-APC (polyclonal) from R&D Systems (Minneapolis, Minn.). The following anti-human antibodies were used for flow cytometry: CD66b-PE (G10F5), CD4-PerCP-Cy5.5 (SK3), CD8-APC (RPA-T8) from BD Biosciences; and CD15-eF450 (HI98) from eBioscience.

Recombinant arginase activity assays. Recombinant full-length human Arg1 was purchased from Enzo Life Sciences (Farmingdale, N.Y.). Recombinant human arginase 2 (Arg2) comprising amino acids 23-254 was purchased from US Biological (Salem, Mass.). Activity assays using 2 nM Arg1 or 4 nM Arg2 were performed in reaction buffer (137 mM NaCl, 2.7 mM KCl, 8 mM $Na_2HPO_4$, 2 mM $KH_2PO_4$, 0.005% Triton X-100, 0.5 mM DTT, 0.5 mM $MgCl_2$, 0.1 mM $CaCl_2$, and 160 µM L-arginine, pH 7.4) at 37° C. for 30 min with a dose-titration of arginase inhibitor. Activity was determined by a spectrophotometric assay using the QuantiChrom Urea Assay Kit (BioAssay Systems, Hayward, Calif.) or by quantification of the generation of $^{13}C(5)$-L-ornithine from $^{13}C(6)$-L-arginine using a SCIEX API4000 mass spectrometer (Applied Biosystems, Foster City, Calif.). Urea produced or $^{13}C(5)$-L-ornithine peak areas were plotted and fitted to a four-parameter equation using GraphPad Prism software (San Diego, Calif.) to determine $IC_{50}$ values.

Native arginase activity in cell lysates. Human granulocytes or erythrocytes were purified from healthy donor peripheral blood using a pan-granulocyte negative selection kit (Stemcell Technologies) or centrifugation on a Ficoll layer, respectively. Frozen human hepatocytes were purchased from XenoTech (Kansas City, Kans.). Lysates were prepared by microtip sonication followed with clarification by centrifugation. Plasma samples from renal cell carcinoma (RCC) patients were obtained by Ficoll centrifugation of whole blood purchased from Conversant Biologics (Huntsville, Ala.). Granulocyte lysate was assayed at 0.094 mg/mL in reaction buffer, as determined by bicinchoninic acid/BCA protein assay (ThermoFisher). Erythrocyte or hepatocyte lysates were assayed at concentrations empirically determined to consume 10-15% of $^{13}C(6)$-L-arginine in 30 min at 37° C. Arginase activity was determined in lysates and plasma by quantification of the generation of $^{13}C(5)$-L-ornithine from $^{13}C(6)$-L-arginine in the presence of a dose titration of arginase inhibitor.

Native arginase activity in intact cells. Intracellular arginase activity was determined for the arginase-expressing HepG2 and K-562 cell lines as follows. HepG2 cells were seeded at 100,000 cells per well one day prior to treatment with arginase inhibitor and K-562 cells were seeded at 200,000 cells per well on the day of arginase inhibitor treatment in duplicate wells of 96-well plates. Cells were treated with a dose-titration of arginase inhibitor in SILAC RPMI-1640 media (Life Technologies/Thermo Fisher Scientific) containing 5% heat-inactivated and dialyzed FBS, antibiotics/anti-mycotic, 10 mM L-arginine, 0.27 mM L-lysine, and 2 mM L-glutamine. Media were harvested after 24 h and urea generated was determined with the QuantiChrom Urea Assay Kit. Wells containing media without cells were used as background controls. For assessing the effect of arginase inhibitor on Arg1 in primary hepatocytes, frozen human hepatocytes (XenoTech) were thawed, allowed to adhere onto collagen-coated wells for 4 h, and then incubated for 48 h in SILAC-RPMI containing 10 mM L-ornithine, no L-arginine, and a dose-titration of arginase inhibitor, at which time the media were analyzed for urea.

Nitric oxide (NO) synthase (NOS) activity assays. Activity of 50 µM arginase inhibitor against 3 NOS isoforms, recombinant murine inducible NOS, recombinant bovine endothelial NOS, and native rat cerebellar neuronal NOS, was determined at Eurofins/Cerep Panlabs (Taipei, Taiwan) by either quantitation of radiolabeled L-citrulline or spectrophotometric measurement of nitrite.

Cell culture. All cell culture reagents were purchased from Corning (Corning, N.Y.) unless indicated otherwise. The human cell lines, HepG2 and K-562, and the murine cell lines, LLC1 (LLC), B16-F10 (B16), CT26.WT (CT26), and 4T1 were obtained from American Type Culture Collection (ATCC, Manassas, Va.). HepG2, K-562, CT26, and 4T1 were maintained in RPMI-1640 (Corning). B16 was maintained in DMEM (Corning). LLC was maintained in DMEM (ATCC). All media were supplemented with 10% fetal bovine serum (FBS), plus penicillin, streptomycin, and amphotericin. Cell lines were grown at 37° C. in a humidified 5% $CO_2$ atmosphere.

Cytotoxicity assays. Cells were seeded in fully-supplemented RPMI-1640 media, treated with a dose-titration of arginase inhibitor in triplicate wells, and incubated for 72 h. Cytotoxicity was assayed by the addition of CellTiterGlo reagent according to the manufacturer's instructions (Promega, Madison, Wis.) followed by fluorescence quantification on a Molecular Devices plate reader (Sunnyvale, Calif.).

T cell and NK cell proliferation assays. T cells or NK cells were purified from healthy donor human blood or from murine splenocytes using a negative selection kit for the appropriate cell type and species from Stemcell Technologies. Isolated T cells or NK cells were loaded with carboxyfluorescein succinimidyl ester (CFSE, Thermo Fisher) and stimulated for 72-96 h in complete growth media containing a minimum of either 50 M L-arginine (NK cells) or 100 µM L-arginine (T cells). For T cell stimulation, a solution of 10 µg/mL anti-CD3 (human clones UCHT1 or OKT3; murine clone $145\text{-}2C_{11}$) was used to coat the wells of a 96-well plate and then T cells were stimulated on immobilized anti-CD3 in the presence of 2 µg/mL soluble anti-CD28 (human clone CD28.2; murine clone 37.51). NK cells were stimulated with recombinant IL-2. Proliferation was quantified by analyzing CFSE dilution by flow cytometry (Guava flow cytometer, Millipore, Billerica, Mass. or Attune N×T flow cytometer, ThermoFisher).

T cell/myeloid cell co-culture assays. Granulocytes were purified from healthy donor peripheral blood using a pan-granulocyte negative selection kit (Stemcell Technologies) and incubated in SILAC-RPMI containing 10% charcoal-stripped FBS, antibiotics/anti-mycotic, 0.27 mM L-lysine, 20 µM $MnCl_2$, 100 µM L-arginine, pH 7.4, and a dose-titration of arginase inhibitor. Granulocytes were incubated for 48 h at 37° C., during which time they spontaneously activate as determined by surface expression of CD66b and scatter properties. T cells isolated from the same donor using a pan-T cell isolation kit (Stemcell Technologies) were loaded with CFSE and plated with immobilized anti-CD3 and soluble anti-CD28 in the presence of the aged granulocytes. The cells were co-cultured at several ratios of granulocytes to T cells as indicated or at a fixed ratio of 4 T cells to 1 granulocyte. Co-cultures were incubated for 3-4 days, at which time media were analyzed for L-arginine and L-ornithine by mass spectrometry and T cell proliferation was determined by flow cytometry. Granulocytic MDSC (G-MDSC) or granulocytes from cancer patients were isolated from whole blood purchased from Conversant Biologics. G-MDSCs were purified from the PBMC layer of a Ficoll gradient by positive selection for $CD66b^+$ cells. Granulocytes were purified from the RBC layer of a Ficoll gradient using Hetasep (Stemcell Technologies). G-MDSC or granulocytes were incubated in co-culture media containing 100 µM L-arginine for 48 h, at which time the cells were removed and the G-MDSC- or granulocyte-conditioned media were used for incubating healthy donor CFSE-loaded T cells on immobilized anti-CD3/soluble anti-CD28 for 3-4 days. Cytokines were quantified in the media from T cell co-culture assays using the Cytometric Bead Array kit according to the manufacturer's instructions (BD Biosciences).

Murine tumor studies. Female wild-type C57BL/6 and Balb/c mice (5-6 weeks old) were purchased from Charles River Laboratories (Hollister, Calif.). Severe combined immune deficient (SCID, B6.CB17-PrkdcSCID/SzJ) and Pmel-1 TCR transgenic (B6.Cg-Thy1a/Cy Tg(TcraTcrb) 8Rest/J) mice (5-6 weeks old) were purchased from The Jackson Laboratory (Bar Harbor, Me.). All mice were housed and treated in accordance with Institutional Animal Care and Use Committee guidelines. For the 4T1 tumor model, $1 \times 10^5$ cells were injected orthotopically into the mammary fat pad; for all other tumor models, $1 \times 10^6$ cells were injected subcutaneously (s.c.) in the right flank. For all studies, arginase inhibitor was administered by oral gavage twice per day at 100 mg/kg starting on study day 1 (1 day after tumor implant). Control groups received vehicle (water) twice daily by gavage. Tumor volume measured by digital caliper (length×width×width/2) and body weight were recorded three times weekly. Animals were euthanized when tumors necrotized or volumes reached 2000 $mm^3$. Anti-PD-L1 antibody (5 mg/kg, clone 10F.9G2, BioXCell, West Lebanon, N.H.) was injected intraperitoneally (i.p.) on days 5, 7, 9, 11, 13, and 15 for the CT26 model. Gemcitabine (Selleckchem, Houston, Tex.) was dosed 50 mg/kg i.p. on days 10 and 16 for the CT26 model or 60 mg/kg i.p. on days 6 and 10 for the LLC model. For $CD8^+$ cell depletion, mice were injected i.p. with anti-CD8 antibody (25 mg/kg, clone 2.43, BioXCell) on days −1, 0, +5, and +10. For NK cell depletion, mice were injected i.p. with anti-NK1.1 antibody (25 mg/kg, clone PK136, BioXCell) in the LLC and B16 models or with anti-Asialo GM1 sera (20 µL, Wako Chemicals, Richmond, Va.) in the CT26 model, per the same schedule as anti-CD8.

Conditional Arg1 deleted mice. Arg1 floxed mice were crossed to the Tie2-Cre deleter strain (The Jackson Laboratory) as previously described. Experimental mice were generated from crossing $Arg1^{Flox/Flox}$; $Tie2\text{-}Cre^+$ males with $Arg1^{Flox/Flox}$; $Tie2\text{-}Cre^+$ females, with Cre negative littermates serving as wild-type controls. Mice were housed and used in accordance with protocols approved by the Institutional Animal Care and Use Committee at St. Jude Children's Research Hospital. LLC cells ($1 \times 10^6$ per mouse) were injected s.c. in the flank region. Mice were orally gavaged with either 100 mg/kg of arginase inhibitor or an equivalent volume of vehicle control (water) every 12 h for 14 days. Mice were euthanized, and tumors excised and weights recorded. Myeloid deletion of Arg1 was confirmed via western blotting of IL-4-stimulated bone marrow-derived macrophages for all animals.

Adoptive T cell transfer studies. Activated gp100-specific $CD8^+$ (Pmel-1) T cells were generated as described in Ya et al. Briefly, splenocytes from Pmel-1 TCR transgenic mice were isolated, pulsed with 1 μM of murine gp100$_{25-33}$ (Anaspec, Fremont, Calif.) and expanded for 1 week in the presence of 60 IU/mL recombinant human IL-2 (Peprotech, Rocky Hill, N.J.). Cells were >90% CD8$^+$V$_\beta$13$^+$ T cells as determined by flow cytometry. C57BL/6 mice were inoculated s.c. with B16 tumor cells. The arginase inhibitor was administered by oral gavage twice per day at 100 mg/kg starting 1 day after tumor implant. On day 7, lymphopenia was induced by a non-myeloablative chemotherapy regimen of 250 mg/kg cyclophosphamide and 50 mg/kg fludarabine administered i.p. The chemotherapy regimen was administered to all groups. On day 9, mice were administered 1×10$^6$ Pmel-1 T cells intravenously (i.v.). Mice receiving Pmel-1 T cells also received recombinant human IL-2 (200,000 IU/dose) administered i.p. twice daily for 3 days starting the day of T cell transfer.

Adoptive NK cell transfer studies. Balb/c mice were inoculated i.v. with 1×10$^5$ CT26 cells. 1×10$^6$ NK cells (isolated from Balb/c spleens the day before injection and incubated with recombinant IL-2 and IL-15 for 18 h) were transferred on the same day as tumor inoculation. The injected NK cells were profiled by flow cytometry to be CD25$^+$ and 80-90% pure with less than 0.4% T cells. Mice were treated with vehicle or arginase inhibitor for 14 days and then lungs were harvested into Fekete's solution and tumor nodules enumerated visually.

Tumor dissociation and flow cytometry. Tumor-bearing mice treated with vehicle or arginase inhibitor (100 mg/kg BID) were sacrificed for flow cytometry analysis on study day 14 (CT26 and LLC), day 9 (B16), or day 10 (4T1). Excised tumors were placed in RPMI-1640 containing 5% FBS on ice, minced with a razor blade, and dissociated in RPMI-1640 supplemented with mouse tumor dissociation enzymes (Miltenyi Biotec, Bergisch Gladbach, Germany) on a GentleMACS Octo Dissociator With Heat (Miltenyi Biotec) according to the manufacturer's instructions. Dissociated tumors were strained through 70 μm nylon mesh, washed with cold PBS containing 2% FBS, blocked with anti-CD16/CD32 (Fc block antibody, eBioscience), and stained for cell surface antigens. For B16 and 4T1 tumors, washed dissociated tumor cells were incubated with Dead Cell Removal MicroBeads (Miltenyi Biotec) and applied to a magnetic column prior to staining. For intracellular staining, cells were fixed and permeabilized using buffers purchased from R&D Systems or eBioscience for cytoplasmic or nuclear antigens, respectively. All tumor flow experiments were acquired on an Attune N×T flow cytometer and analyzed with FlowJo software version 10 (Ashland, Oreg.), using fluorescence-minus-one controls for gating and single-stained OneComp eBeads (eBioscience) to set compensation matrices.

Gene expression analysis. LLC tumors from mice (N=6 per group) treated with vehicle or arginase inhibitor (100 mg/kg twice daily) for 13 days were collected, placed into neutral buffered formalin overnight, transferred into 70% ethanol, and shipped to Core Diagnostics (Hayward, Calif.) for paraffin embedding. RNA was extracted for gene expression analysis and transcripts were quantified by NanoString Technologies (Seattle, Wash.).

Cytokine analysis. LLC tumors from mice (N=5 per group) treated with vehicle or arginase inhibitor (200 mg/kg twice daily) for 14 days were collected and flash frozen in liquid nitrogen. Tumors were homogenized in 50 mM Tris-HCl buffer containing 2 mM EDTA, pH 7.4 and protease inhibitors. The homogenate was centrifuged and the supernatant was collected and re-frozen. Cytokines in the supernatant were quantified by Myriad Rules Based Medicine (Austin, Tex.).

Immunohistochemistry (IHC). Automated IHC was performed by Indivumed (Hamburg, Germany) using the Discovery XT staining platform (Roche Diagnostics/Ventana Medical Systems, Mountain View, Calif.) on formalin-fixed and paraffin-embedded (FFPE) samples and tumor tissue microarrays (TMA). The rabbit anti-human Arg1 monoclonal antibody clone EPR6672(B) from Abcam/Epitomics (Burlingame, Calif.) was validated using 8 different cases of hepatocellular carcinoma (HCC) and one sample of normal liver tissue as positive control tissue; normal tonsil tissue and isotype control antibody were used as negative controls. IHC was performed on 11 different tumor histologies: non-small cell lung cancer (NSCLC, squamous and adenocarcinoma), breast cancer (triple negative and non-triple negative), gastric adenocarcinoma, colorectal cancer (CRC), prostate adenocarcinoma, pancreatic cancer, ovarian cancer, bladder cancer, and RCC. Arg1$^+$ cells per mm$^2$ were quantified by digital histopathology (Oracle BIO).

Multiparameter immunofluorescence. Tumor TMAs containing samples from patients with lung squamous cell carcinoma, CRC, RCC, esophageal carcinoma, and head and neck cancer were purchased from US Biomax or US Biolabs (Rockville, Md.). Multiparameter immunofluorescence using the MultiOmyx platform for markers including Arg1, CD15, and CD68 was performed and analyzed by GE Clarient/NeoGenomics Laboratories (Aliso Viejo, Calif.).

Plasma Arg1 and L-arginine. Plasma Arg1 protein was determined by enzyme linked immunosorbent assay (ELISA, BioVendor, Asheville, N.C.) in samples from healthy volunteers and patients with head and neck cancer (N=5), HCC (N=3), mesothelioma (N=3), CRC (N=3), T cell prolymphocytic leukemia (N=2), melanoma (N=2), bladder cancer (N=4), NSCLC (N=11), small cell lung cancer (N=17), undefined lung cancer (N=6), acute myeloid leukemia (N=9), RCC (N=9), and breast cancer (N=2). Plasma L-arginine was determined by mass spectrometry in samples from patients with mesothelioma (N=3), CRC (N=3), NSCLC (N=9), small cell lung cancer (N=3), undefined lung cancer (N=3), head and neck cancer (N=3), and T cell prolymphocytic leukemia (N=2). All cancer patient samples were purchased from Conversant Biologics.

Results

The arginase inhibitor was tested in biochemical and cellular assays for the ability to inhibit arginase enzymes from a variety of sources. Arginase inhibitor inhibited recombinant human Arg1 (IC$_{50}$=98 nM) and the related enzyme Arg2 (IC$_{50}$=274 nM) (Table 1). Arg2 catalyzes an identical chemical reaction and shares 60% sequence identity with Arg1, but differs in its tissue distribution and subcellular localization. A second enzyme class that also metabolizes L-arginine and is implicated in inflammation is NOS, which produces L-citrulline and the biological mediator NO. The arginase inhibitor was tested for the ability to inhibit the three NOS isoforms, endothelial NOS, neuronal NOS, and inducible NOS. No inhibition of NOS enzymes was observed in the presence of 50 μM arginase inhibitor (Table 1). These results show arginase inhibitor is a potent inhibitor of arginase with no activity against NOS. Arginase inhibitor was next tested for the ability to inhibit native Arg1 enzymes in lysates of human granulocytes, peripheral blood erythrocytes, and primary hepatocytes. It was found that arginase inhibitor inhibited native arginase in lysates with similar potency to that observed for recombinant arginases (Table 1). In addition, Arg1 protein and activity have been reported to be elevated in the plasma of RCC patients compared to healthy donors and inhibition by arginase inhibitor of arginase activity was observed in plasma isolated from RCC patients (Table 1).

TABLE 1

Biochemical potency of arginase inhibitor on arginase or NOS.

| | Arginase inhibitor, $IC_{50}$ (nM) |
|---|---|
| Purified enzyme assay | |
| Recombinant human Arg1 | 86 (±25) |
| Recombinant human Arg2 | 296 (±5) |
| Recombinant bovine endothelial NOS | N/A |
| Rat cerebellar neuronal NOS | N/A |
| Recombinant murine inducible NOS | N/A |
| Cell lysate assay | |
| Human granulocyte lysate | 178 (±28) |
| Human erythrocyte lysate | 116 |
| Human hepatocyte lysate | 158 (±23) |
| Cancer patient plasma | 122 (±32) |

Mean $IC_{50}$ values in nanomolar for arginase inhibitor activity of purified recombinant arginases or native arginase in cell lysates or patient plasma. Standard deviations are indicated in parentheses. Recombinant Arg1 assays (N=3) were performed in duplicate wells in the presence of 160 µM L-arginine. Recombinant Arg2 assays (N=2) were performed in triplicate wells with 20 mM L-arginine. Arginase activity assays using human granulocyte lysate (N=3), human erythrocyte lysate (N=1), human hepatocyte lysate (N=4), and cancer patient plasma (N=5) were performed in duplicate wells with 160 µM L-arginine. Purified NOS enzyme activity was assayed in the presence 50 µM arginase inhibitor, which showed no inhibitory activity against the three NOS isoforms. N/A=not applicable.

Granulocytic Arg1 is inactive until it is exocytosed, however active Arg1 is localized in the cytoplasm in other cell types, including liver hepatocytes. Arginase inhibitor was next tested for the ability to inhibit endogenous arginase in intact cells. Arginase inhibitor exhibited low potency against intracellular arginase in the hepatocellular carcinoma (HCC) cell line HepG2, the chronic myelogenous leukemia cell line K-562, and primary human hepatocytes (Table 2). The low potency of arginase inhibitor against arginase in intact cells is likely due to inefficient penetration of arginase inhibitor across the cell membrane. These results show that arginase inhibitor is a potent and specific inhibitor of extracellular arginase.

TABLE 2

Potency of arginase inhibitor on arginase activity in intact cells.

| Intact cell assay | Arginase inhibitor, $IC_{50}$ (µM) |
|---|---|
| Human HepG2 cell line | 32 (±5.6) |
| Human K562 cell line | 139 (±8.8) |
| Primary Human Hepatocytes | 210 |

Mean $IC_{50}$ values in micromolar for arginase inhibitor inhibition of arginase activity in intact cells. Standard deviations are indicated in parentheses. HepG2 (N=3) and K562 (N=2) cell lines were plated in duplicate wells in the presence of 10 mM L-arginine. For primary human hepatocytes (N=1), arginase activity was measured in duplicate wells in the presence of media containing 10 mM L-ornithine and lacking L-arginine. Arginase activity was measured as production of urea in the media after 24 h.

To determine if arginase inhibitor can restore lymphocyte proliferation in the context of immunosuppressive arginase-expressing myeloid cells, it was first confirmed that lymphocytes require exogenous L-arginine to proliferate. Purified T cells or NK cells were stimulated with anti-CD3/anti-CD28 or IL-2, respectively, in the presence or absence of L-arginine in the media. Proliferation of human and murine T cells (FIG. 2A, left) and NK cells (FIG. 2A, right) only occurred in media that contained L-arginine, as expected.

Figure 2A:
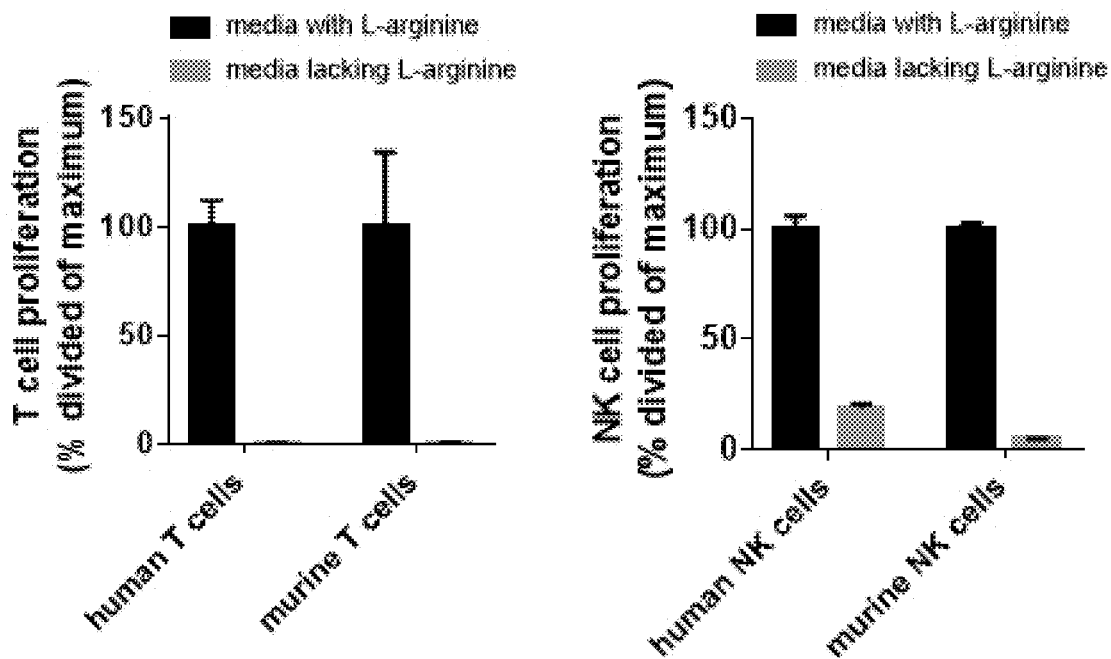
Figure 2B:
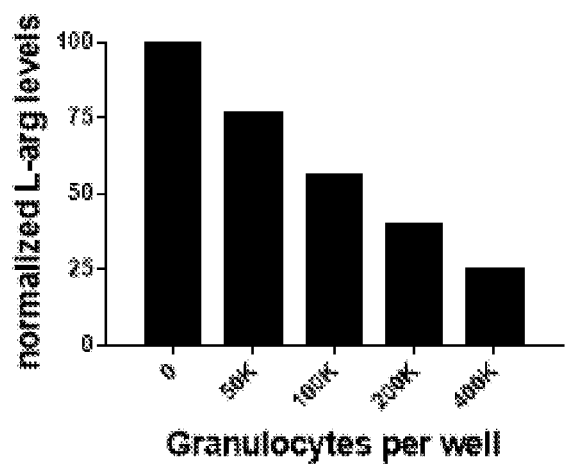
Figure 2C:
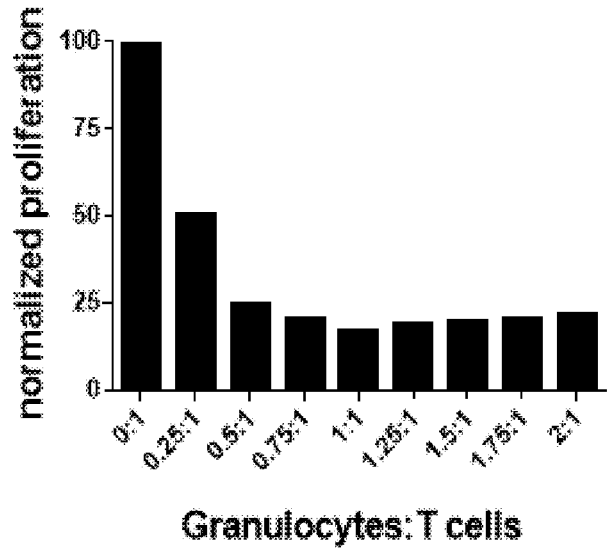
Figure 2D:
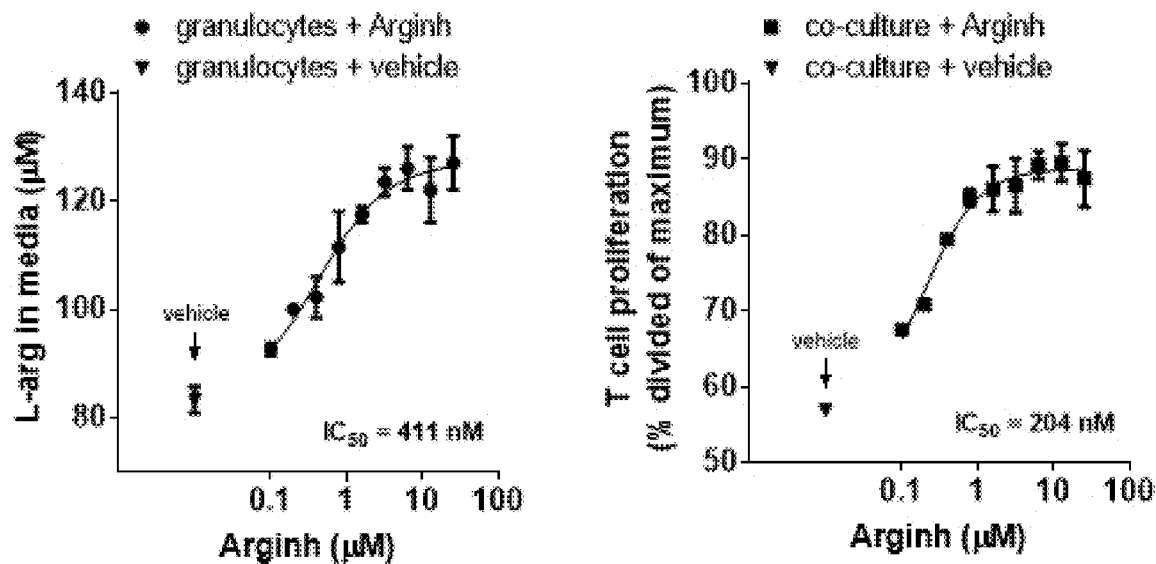

To determine if arginase activity is necessary for myeloid cell-mediated suppression of T cell proliferation, T cell proliferation was assayed in co-culture with human myeloid cells in the presence or absence of arginase inhibitor. Granulocytes are an abundant myeloid cell recruited from peripheral blood to sites of wound healing, infection, and the TME. Arg1 is stored in cytoplasmic granules and upon activation, which occurs spontaneously in vitro, granulocytes release active Arg1 into the extracellular milieu. Purified human granulocytes from a healthy donor consumed L-arginine from the media (FIG. 2B). When activated granulocytes were co-cultured with autologous T cells, T cell proliferation was inhibited (FIG. 2C). The addition of arginase inhibitor blocked depletion of L-arginine from the media (FIG. 2D, left) and restored T cell proliferation to 90% of the proliferation observed for T cells without granulocytes (FIG. 2D, right). These results show that L-arginine depletion by Arg1 is necessary for granulocyte-mediated suppression of T cell proliferation in vitro, and that arginase inhibitor reverses this immunosuppression.

Figure 2E:
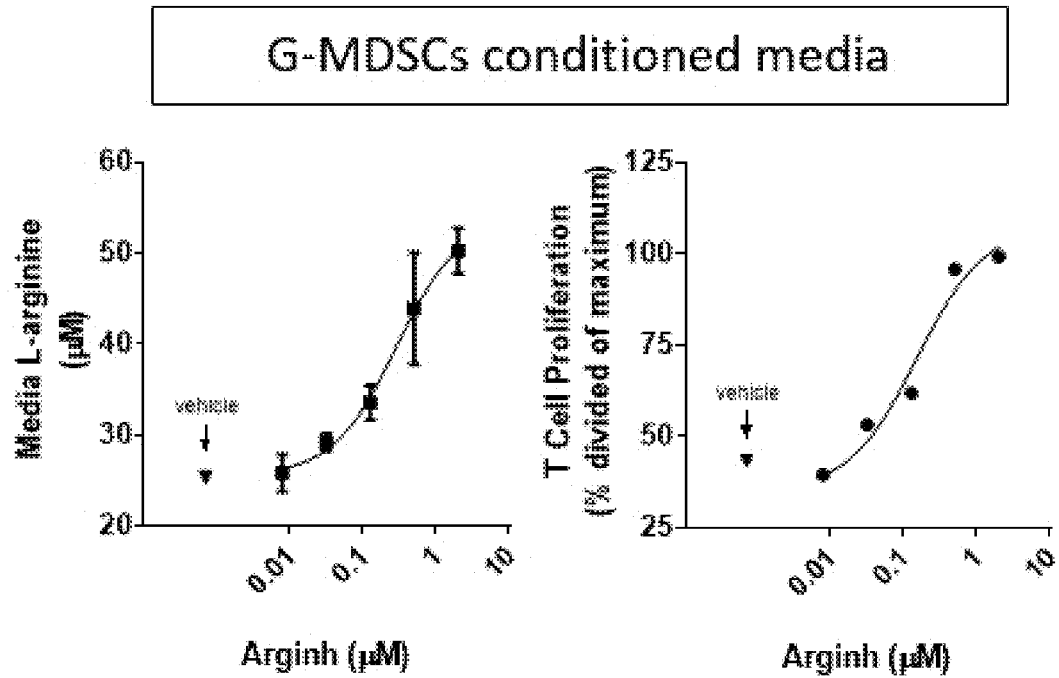
Figure 2F:
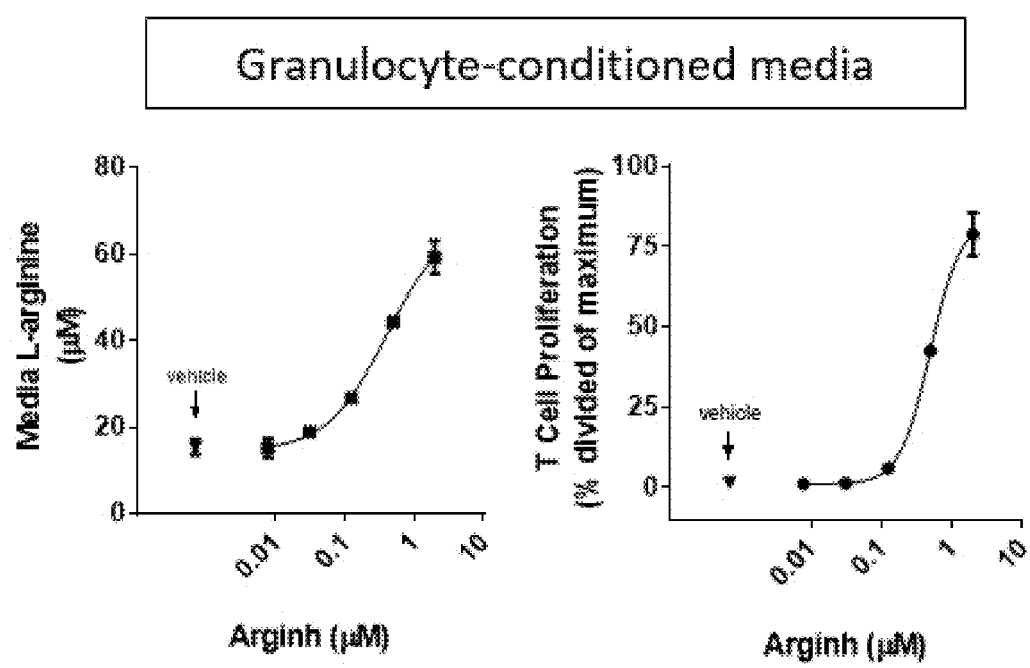
Figure 2G:
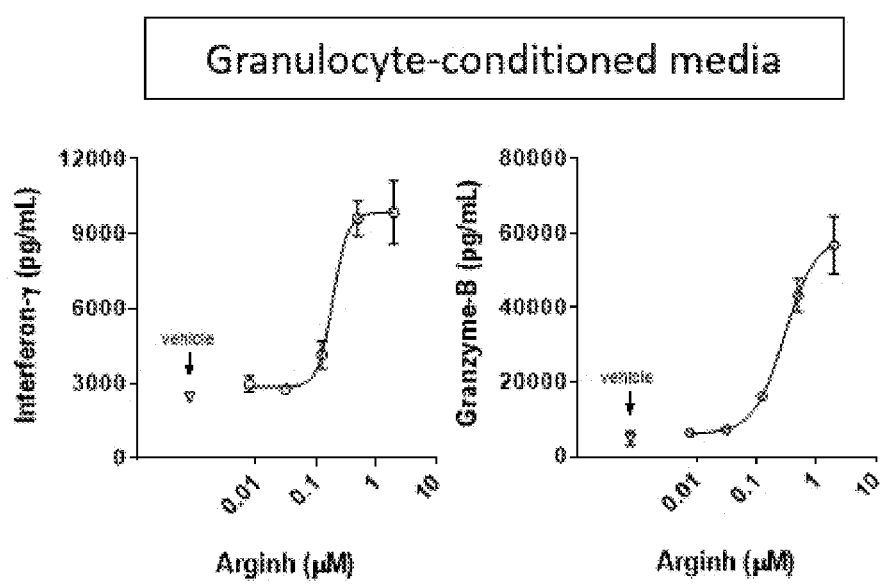

It was then tested to determine whether arginase inhibitor could block T cell suppression conferred by myeloid cells derived from cancer patients. G-MDSC purified from the peripheral blood of a patient with lung cancer or granulocytes purified from a head and neck cancer patient were cultured for 48 h and the conditioned media were then used in T cell proliferation assays. T cells from healthy donors were used in lieu of the cancer patient donors' T cells due to the limited amount of sample available from individual patients. Cancer patient-derived G-MDSCs or granulocytes reduced the amount of L-arginine in the media, and arginine depletion was blocked by arginase inhibitor (FIG. 2E, left and FIG. 2E, left). T cell proliferation was inhibited in the media conditioned by G-MDSC or granulocytes, and proliferation was restored to 99% or 79%, respectively, of control levels by the addition of arginase inhibitor (FIG. 2E, right and FIG. 2E, right). Arginase inhibitor also restored secretion into the media of the T cell inflammatory cytokines interferon-γ and granzyme-B (FIG. 2G). Together these data demonstrate that inhibition of arginase by arginase inhibitor blocks myeloid cell-mediated immunosuppression, rescuing T cell proliferation and cytokine secretion.

To determine if arginase inhibition by arginase inhibitor could be interrogated for anti-tumor efficacy in mouse models of cancer, pharmacokinetic and pharmacodynamic studies were performed in tumor-bearing mice. Following a single dose of arginase inhibitor or BID dosing for 5 days, dose-dependent exposure of arginase inhibitor was observed in both tumor and plasma (FIG. 3A and FIG. 3B, top rows). Oral dosing of arginase inhibitor in tumor-bearing mice also raised the amount of L-arginine in tumor and plasma, indicating an on-target pharmacodynamic effect of arginase inhibitor (FIG. 3A and FIG. 3B, bottom rows). Importantly, arginase inhibitor was well-tolerated at doses of 100 mg/kg twice daily for 23 days, with no significant clinical observations or impact on body weight (FIG. 3C).

Arginase inhibitor was tested in multiple syngeneic murine models of cancer. Blocking arginase with arginase inhibitor significantly inhibited the growth of CT26, LLC, B16, and 4T1 tumors (FIG. 4A). Single-agent activity of arginase inhibitor is noteworthy since many experimental immune oncology agents are largely ineffectual as monotherapies. Confirmation that arginase inhibitor targets Arg1 in vivo was assessed with a genetically altered mouse strain containing a conditional disruption of Arg1 in the myeloid lineage. LLC cells injected into $Arg^{flox/flox}$; Tie2-Cre$^+$ mice (FIG. 4B, indicated as ARG1 $^{\Delta M}$) grew smaller tumors that were similar in size to arginase inhibitor treated $Arg^{flox/flox}$; Tie2-Cre$^-$ mice (FIG. 4B, indicated as ARG1$^{WT}$), and arginase inhibitor treatment of $Arg^{flox/flox}$; Tie2-Cre$^+$ animals conferred no further reduction in tumor growth, consistent with specific on-target inhibition of Arg1 by arginase inhibitor (FIG. 4B). Together, these results provide evidence that Arg1 activity promotes tumor growth and that elimination of myeloid cell Arg1 expression or pharmacological blockade of arginase by arginase inhibitor limits tumor growth in vivo.

Figure 5A:
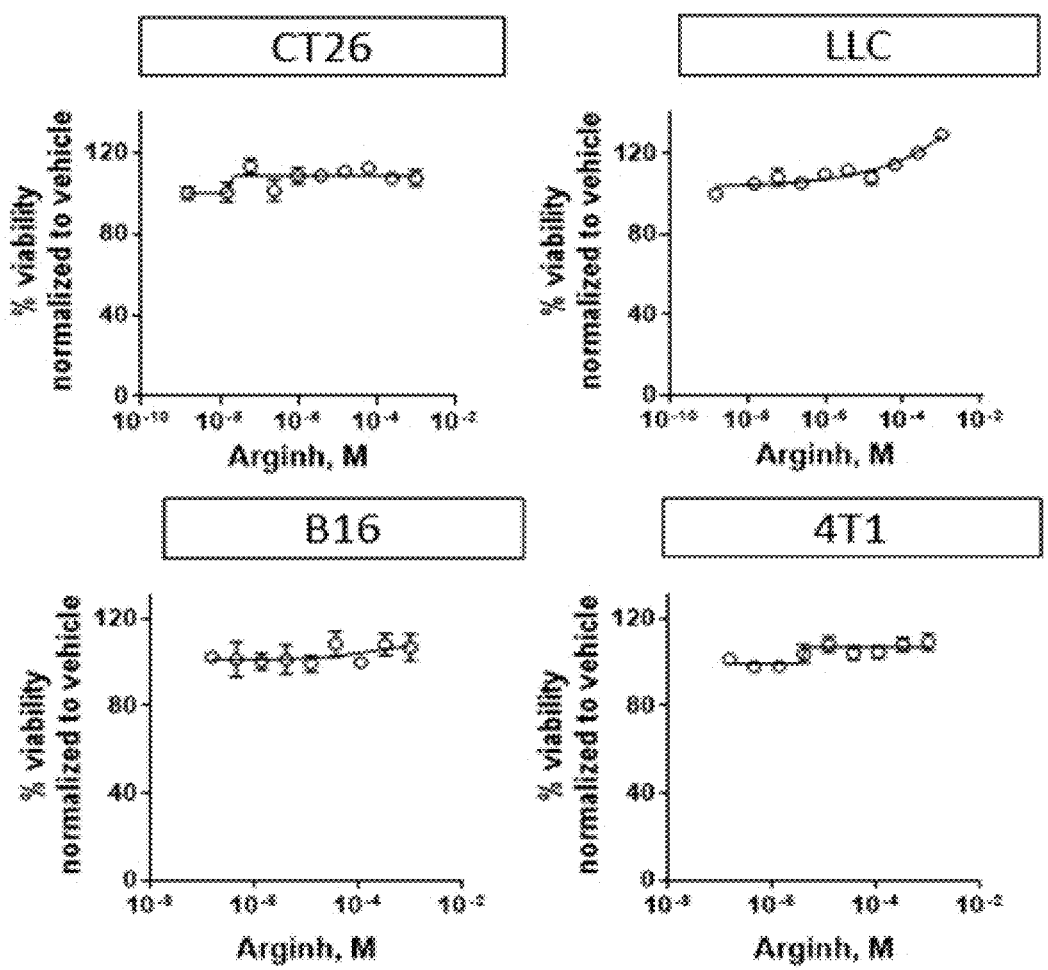
Figure 5B:
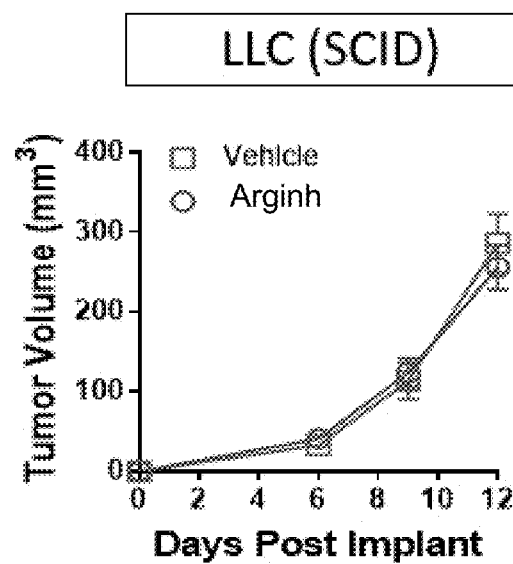
Figure 5C:
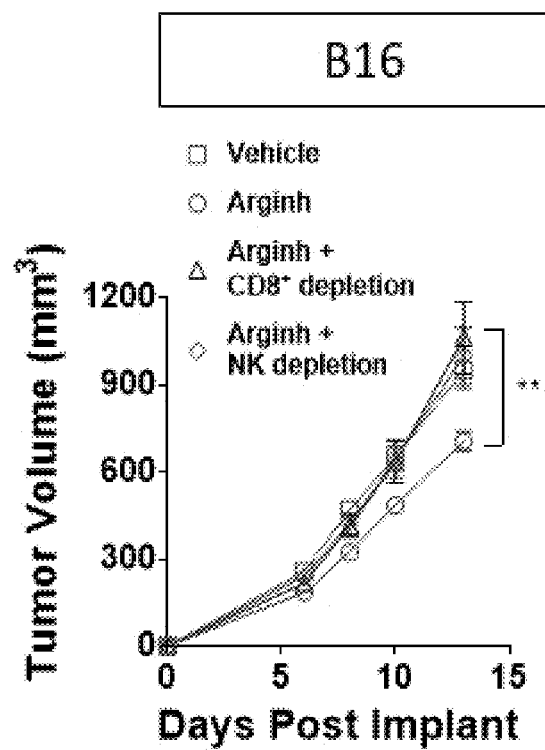
Figure 5D:
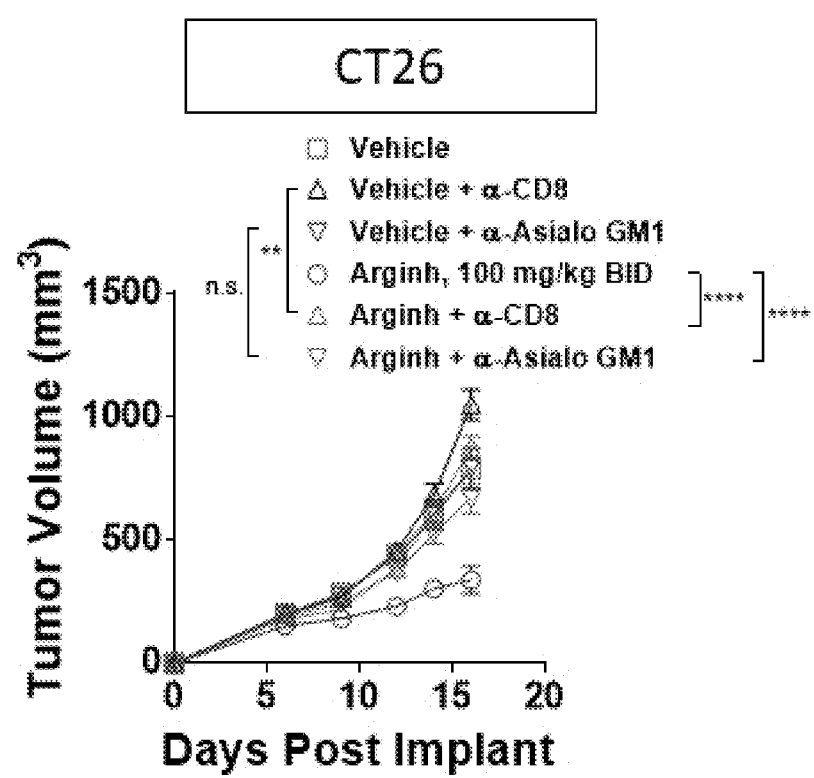
Figure 5E:
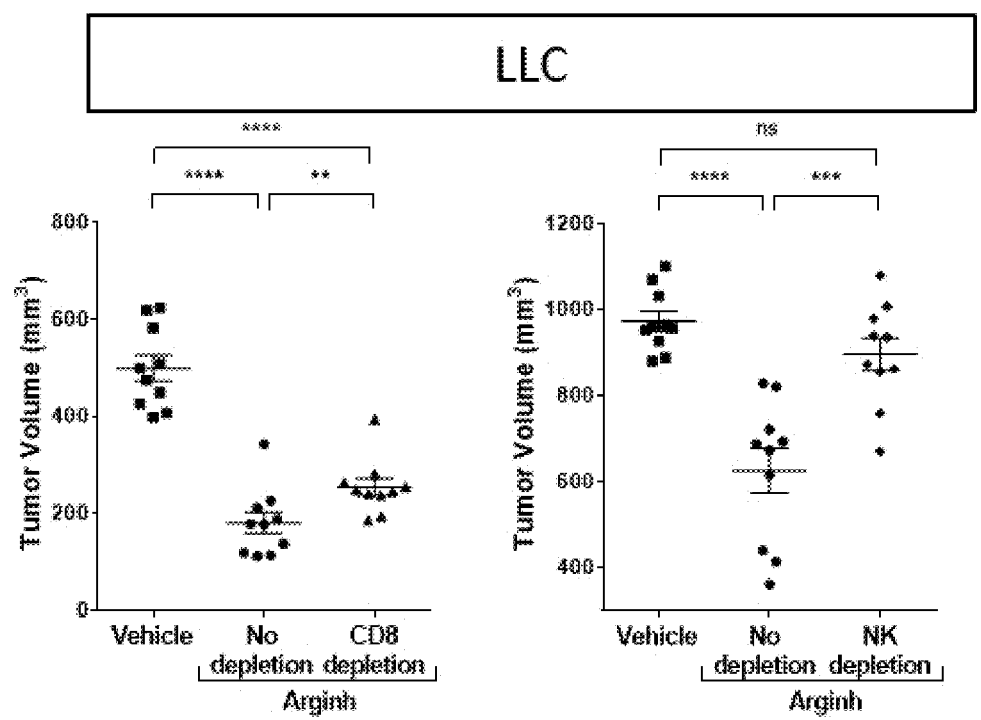

A series of experiments was performed to address the in vivo molecular mechanism of action of arginase inhibitor. Arginase inhibitor is not directly cytotoxic to murine cancer cell lines by assaying the growth of CT26, LLC, B16, and 4T1 cell lines in the presence of a dose-titration of arginase inhibitor. No growth inhibition of murine cancer cell lines was observed in the presence of 1 mM arginase inhibitor (FIG. 5A). To test if the mechanism of in vivo efficacy of arginase inhibitor is immune cell-mediated, arginase inhibitor was administered to LLC tumor-bearing SCID mice. The efficacy of arginase inhibitor was abrogated in the SCID background (FIG. 5B), indicating arginase inhibitor requires an intact immune system to inhibit tumor growth. To further investigate the immune compartments involved in mediating the effect of arginase inhibitor, tumor growth was assessed in mice lacking specific immune cell subsets. Depletion of either CD8$^+$ cells or NK cells in the B16 (FIG. 5C) and CT26 (FIG. 5D) tumor models blocked the efficacy of arginase inhibitor, indicating that both CD8$^+$ cells and NK cells are required for the full anti-tumor effect of arginase inhibitor in these models. In the LLC tumor model, depletion of NK cells resulted in loss of efficacy, while depletion of CD8$^+$ cells had a smaller effect (FIG. 5E). Collectively, these results indicate that the anti-tumor effect of arginase inhibitor is mediated by the immune system and requires cytotoxic lymphocytes.

Figure 6A:
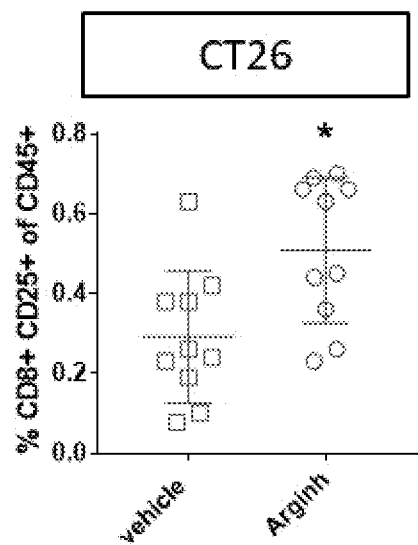
Figure 6B:
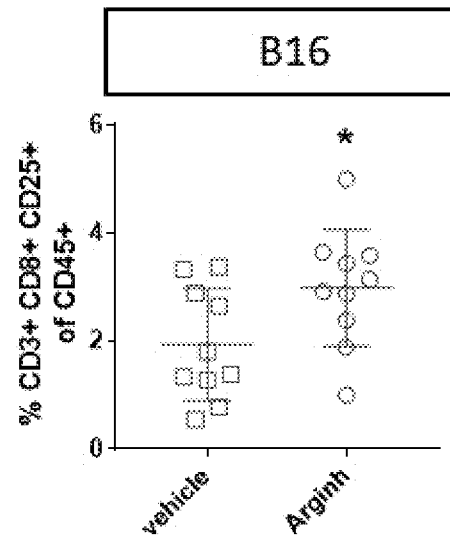
Figure 6C:
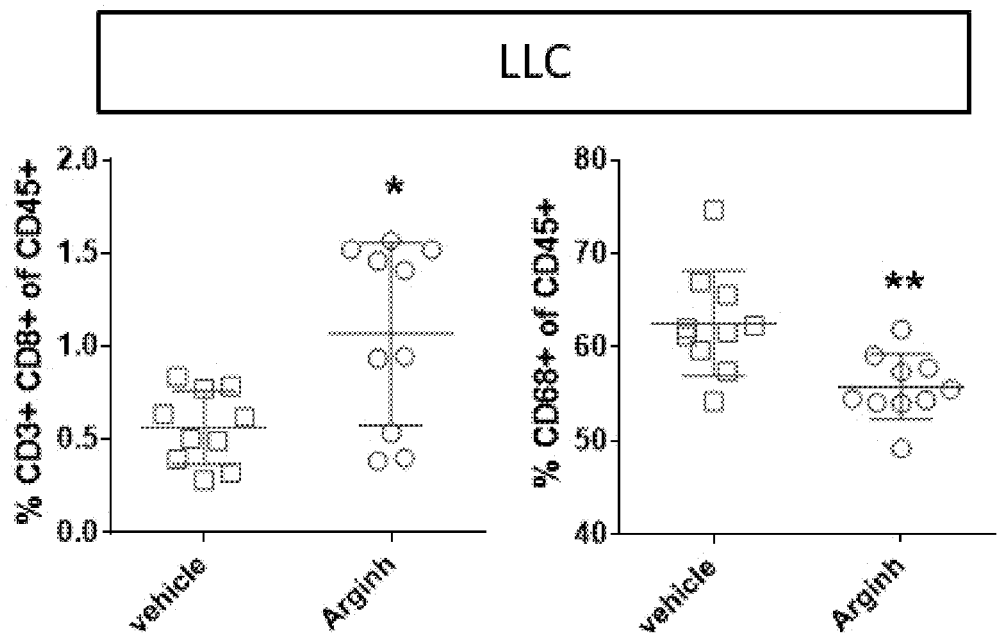
Figure 6D:
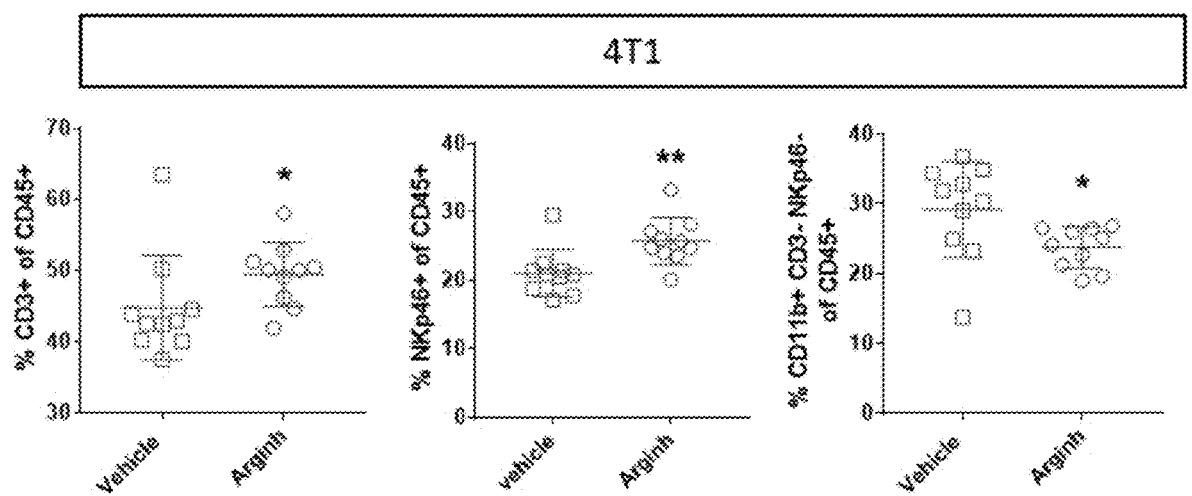
Figure 6E:
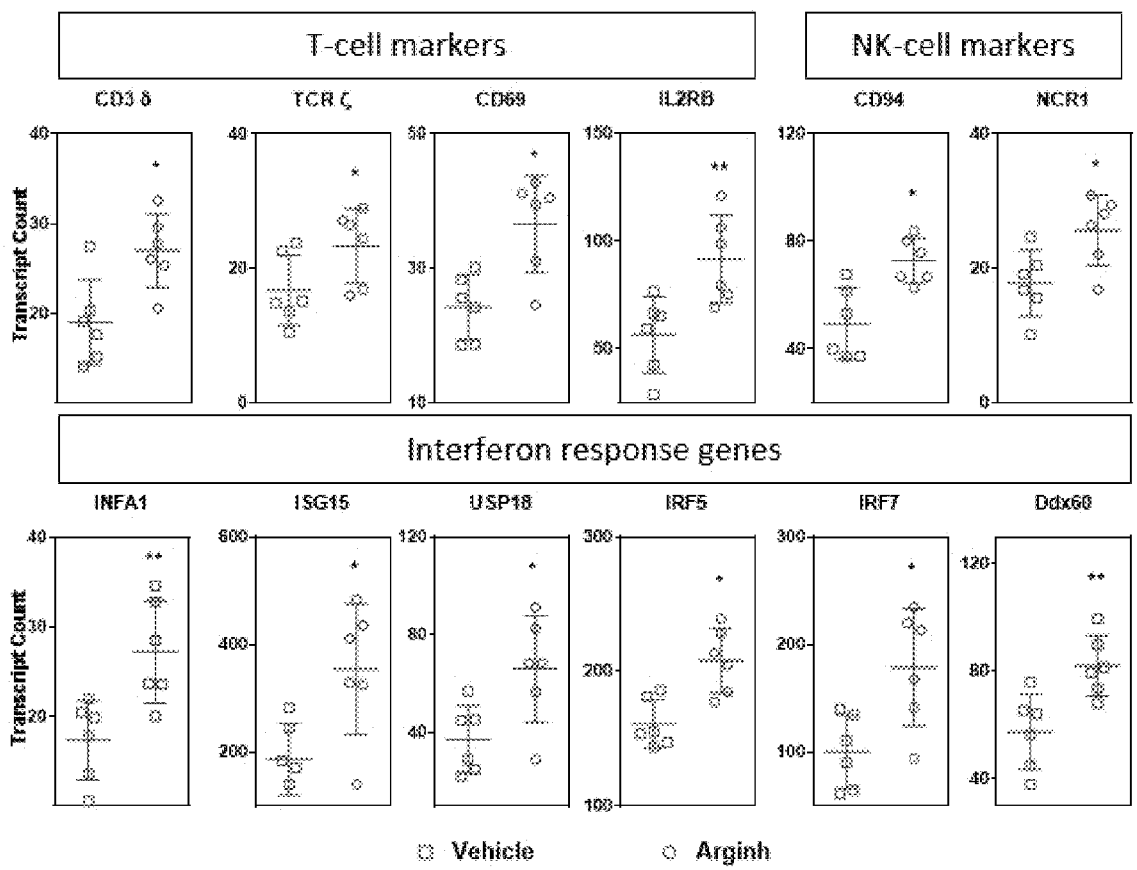
Figure 6F:
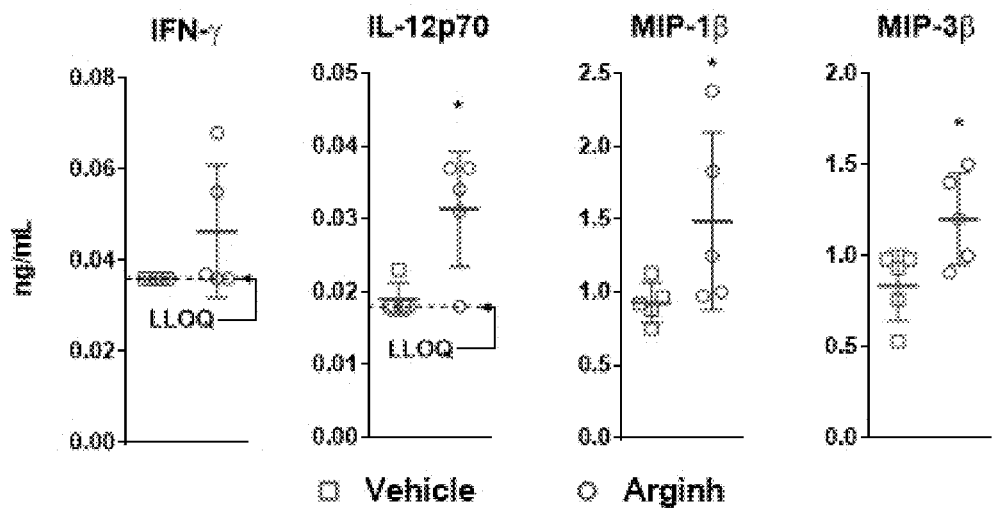

To further probe the immune cell-mediated mechanism of action of arginase inhibitor, flow cytometry was performed on tumors from animals treated with vehicle or arginase inhibitor and changes in specific immune cell populations were quantified. In each of the models where tumor growth was inhibited by arginase inhibitor, statistically significant changes were observed in immune cell populations indicative of an increase in inflammation in the TME (FIG. 6A). In the CT26 (FIG. 6A) and B16 (FIG. 6B) models, arginase inhibitor treatment resulted in an increase in tumor-infiltrating activated CD25$^+$ CD8$^+$ cytotoxic T cells compared to vehicle-treated controls. In the LLC model, arginase inhibitor treatment caused an increase in CD8$^+$ T cells in the tumor, as well as a decrease in CD68$^+$ macrophages, compared to vehicle-treated controls (FIG. 6C). In the 4T1 model, where arginase inhibitor had a modest effect on tumor growth, nevertheless changes were observed in immune cell populations consistent with increased inflammation in the tumor: an increase in CD3$^+$ T cells, an increase in NK cells, and a decrease in myeloid cells in the tumors of arginase inhibitor-treated animals compared to vehicle treated controls (FIG. 6D). Consistent with increased inflammation in the tumors of arginase inhibitor-treated animals compared to vehicle controls, arginase inhibitor was linked to increases in transcripts of interferon-responsive genes (FIG. 6E) and increases in inflammatory cytokines (FIG. 6F). Taken together, this data indicate that the molecular mechanism of tumor growth inhibition by arginase inhibitor is immune cell-mediated and results from an increase in inflammation in the tumor microenvironment that includes an increase in cytotoxic lymphocytes and a decrease in suppressive myeloid cells.

Figure 7A:
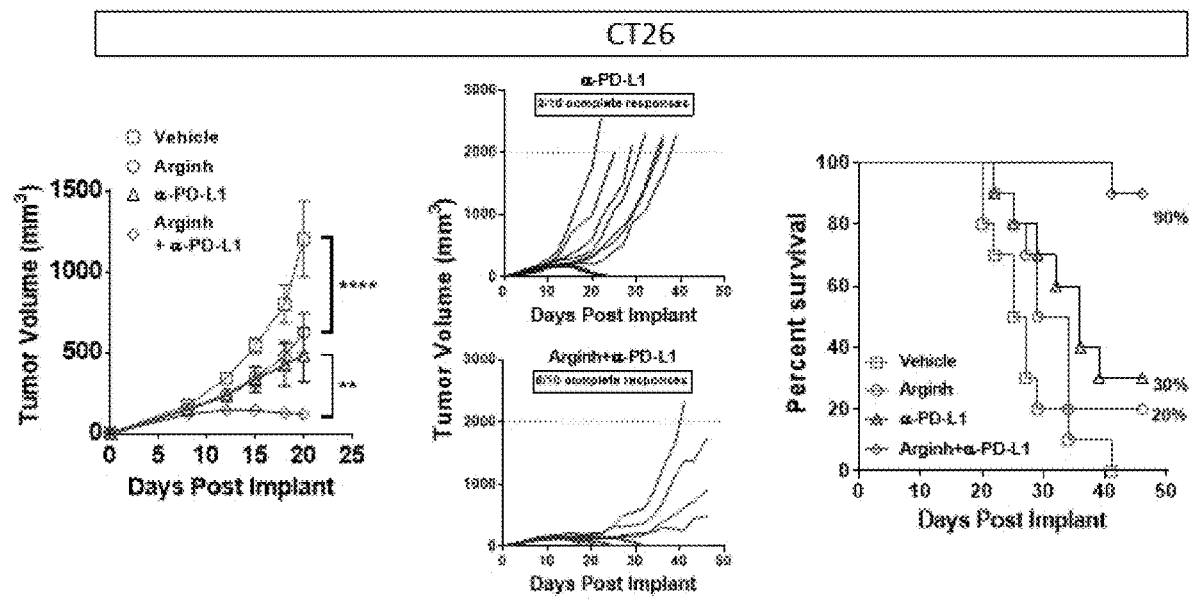
Figure 7B:
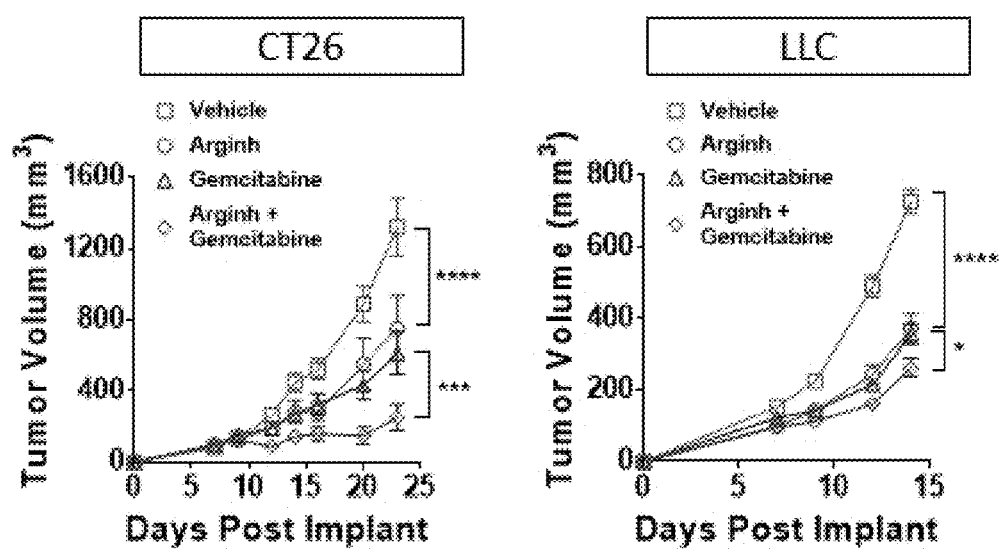
Figure 7C:
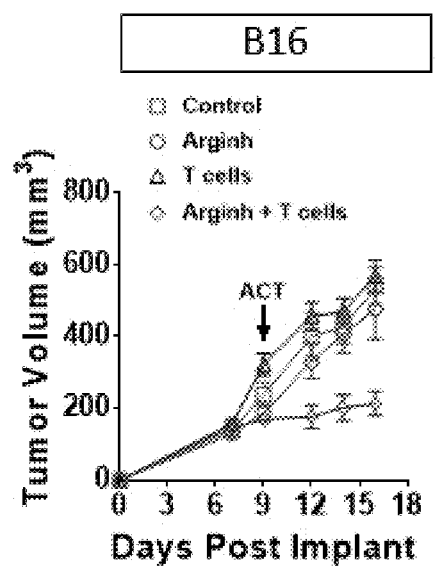
Figure 7D:
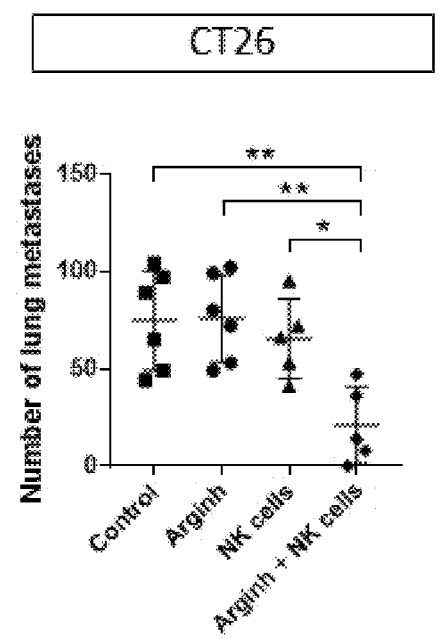
Figure 8D:
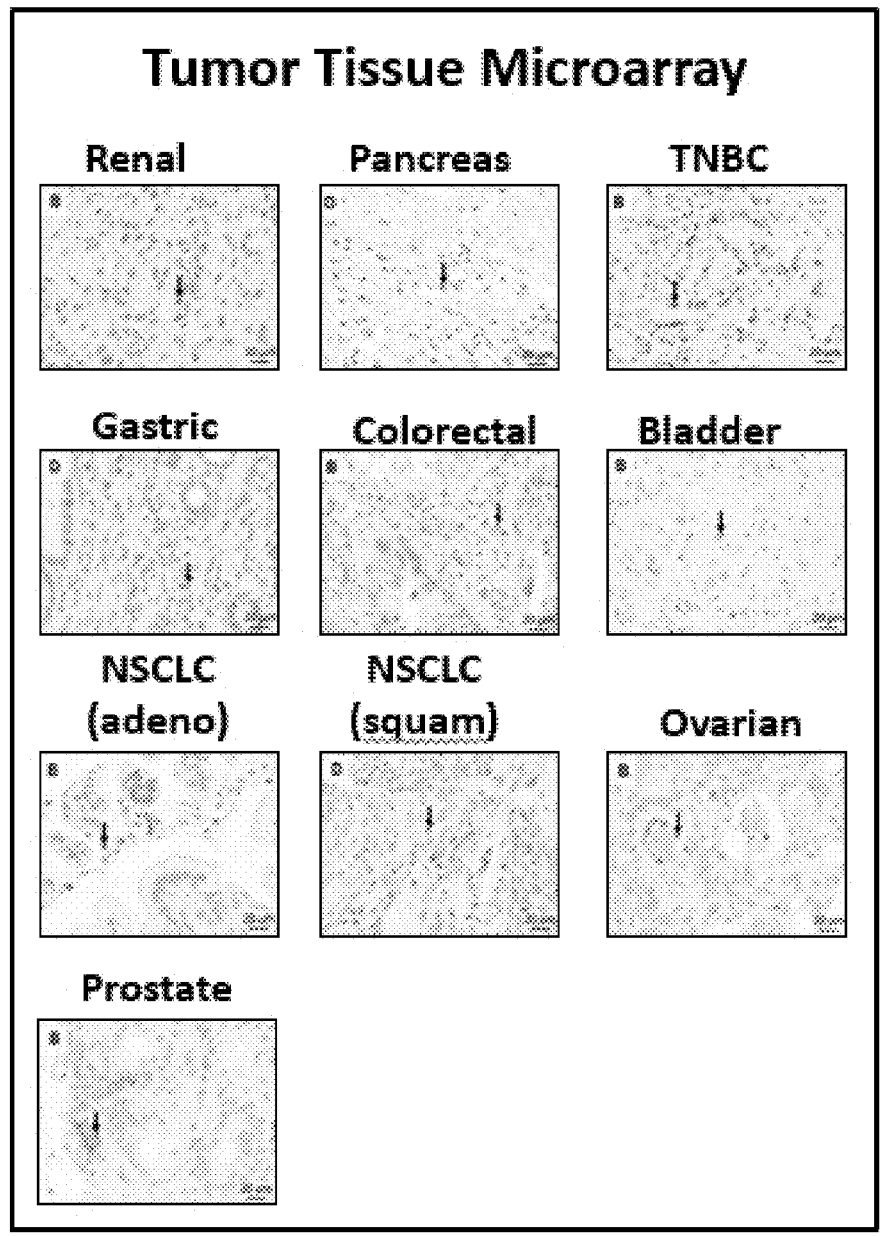
Figure 8E:
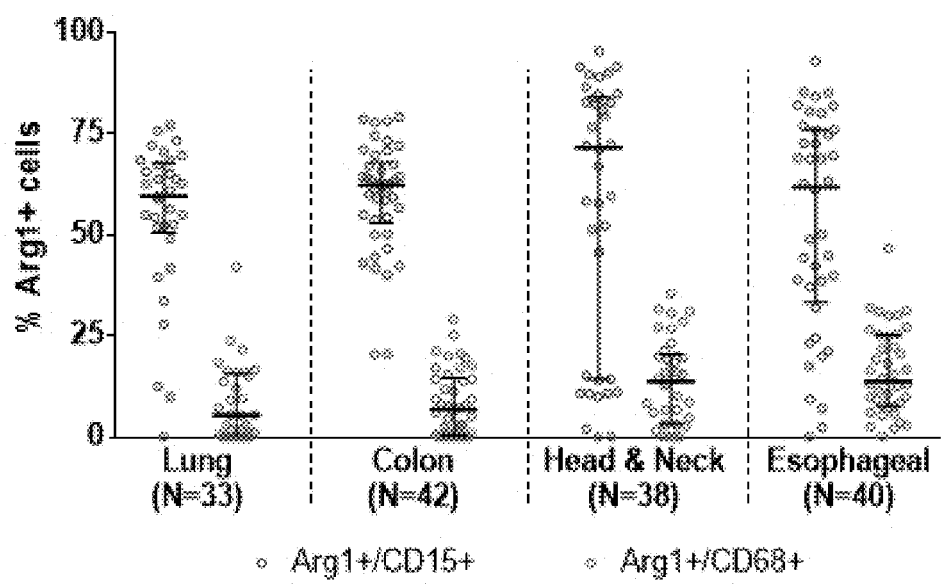
Figure 8F:
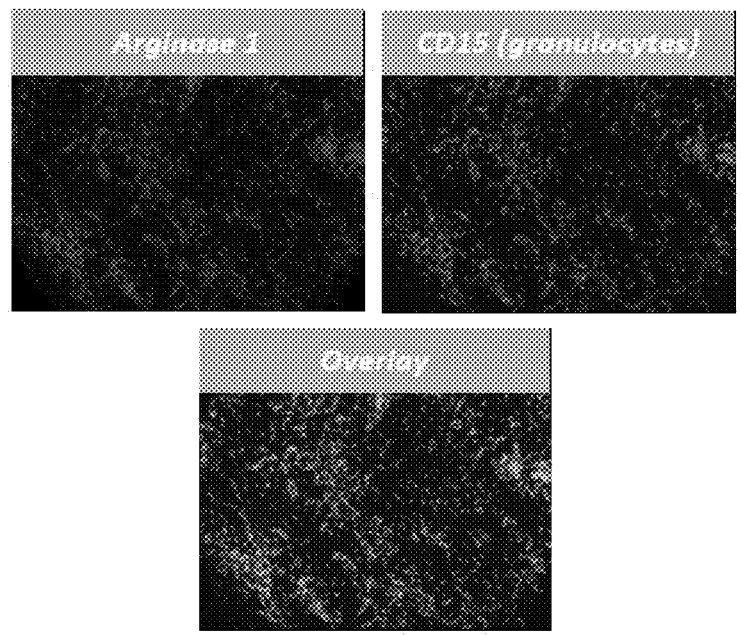

In growing tumors, effective immunity may be blocked by more than one suppressive mechanism, including expression of immune checkpoint proteins and depletion of essential nutrients from the TME. Combining arginase inhibitor with other immune-modulating agents might further reduce tumor growth and this idea was tested with four different combinations. First, CT26 tumor-bearing mice were treated with arginase inhibitor in combination with the checkpoint blockade therapy anti-PD-L1. While tumor growth was reduced with arginase inhibitor or anti-PD-L1 as monotherapies, tumor growth inhibition was enhanced by combining the two agents (FIG. 7A, left). Complete tumor regression was achieved in three out of ten mice treated with anti-PD-L1 alone, whereas the combination therapy resulted in six complete responses (FIG. 7A, center), with 90% survival at study day 46 for the combination group compared to 30% survival for the anti-PD-L1 single agent group (FIG. 7A, right). Some standard-of-care chemotherapeutics have been observed to modulate the immune infiltrate. While the primary mechanism of action of gemcitabine, a nucleoside analog, is considered to be inhibition of DNA synthesis, it has also been observed to suppress MDSCs. Therefore, it was reasoned that gemcitabine may augment the activity of arginase inhibitor. Indeed, arginase inhibitor treatment in combination with gemcitabine resulted in a significant increase in tumor growth inhibition in both the CT26 (FIG. 7B, left) and LLC (FIG. 7B, right) tumor models. Lastly, two different cellular therapies were used in combination with arginase inhibitor. B16 tumor-bearing mice treated with arginase inhibitor in combination with T cells specific for the PMEL tumor antigen exhibited significantly reduced tumor growth compared to mice treated with either single agent (FIG. 7C). Of note, the significant tumor growth inhibition in mice treated with the combination of arginase inhibitor plus T cells is consistent with the striking survival benefit that was observed for T cell therapy in mice deleted for myeloid ARG1. NK cell therapy was used in a lung metastasis model. CT26 tumor-bearing mice treated with arginase inhibitor in combination with NK cells had significantly fewer lung metastases compared to control groups (FIG. 7D). Taken together, these results indicate that arginase inhibitors may be an attractive combination agent with multiple types of anti-cancer therapies To investigate which tumor types may be more likely to respond to arginase inhibition, human tumor microarrays were studied by immunohistochemistry for Arg1 protein expression. An abundance of Arg1$^+$ infiltrating immune cells in multiple tumor types was found (FIGS. 8A-8D), with especially high numbers in tumors of the lung, gastrointestinal tract, and bladder. Tumor cells were largely negative for Arg1 staining with the exception of HCC (FIG. 8C). Tumor tissue microarrays were also stained by multi-parameter immunofluorescence for Arg1 and other immune cell markers, and it was found that Arg1 was more frequently associated with the granulocytic marker CD15 than with the macrophage marker CD68 (FIG. 8E), and in some cases, striking co-localization between Arg1 and CD15 was observed (FIG. 8F). These data confirm Arg1 expression in multiple tumor types.

In addition to tumor expression, Arg1 protein and activity have been observed in the peripheral blood and have been reported to be higher in the plasma of RCC patients compared to healthy volunteers. To investigate whether the amount of Arg1 is higher in cancer patients than in healthy donors, Arg1 protein was measured in the plasma of 31 healthy donors and 76 cancer patients across 12 different histologies (see Methods). Arg1 was significantly higher for cancer patients compared to the healthy volunteers (FIG. 8G). Peripheral blood L-arginine has also been reported to be lower in patients with RCC. Plasma L-arginine was measured for 20 healthy volunteers and 26 cancer patients across 7 different histologies. L-arginine was significantly lower for the cancer patients compared to the healthy individuals (FIG. 8H). These results suggest that cancer patients may experience immune suppression that is associated with higher circulating Arg1 and lower amounts of L-arginine compared to healthy individuals, and that inhibiting circulating Arg1 and raising plasma L-arginine with arginase inhibitor could confer an immune benefit in the context of cancer.

It is believed that raising arginine levels would be immune-stimulatory in the context of cancer for the following reasons: first, cytotoxic lymphocytes require exogenous arginine for proliferation in response to in vitro stimulation; second, many cancer patients are immunosuppressed and have lower plasma arginine compared to healthy individuals; and lastly, activated immunosuppressive myeloid cells consume arginine and compete with other arginine auxotrophs such as cytotoxic lymphocytes in the TME for this amino acid. Thus, raising arginine in cancer patients could be critical for the immune system to mount an effective anti-tumor response.

Arginine depletion by myeloid cells is primarily mediated by the enzymes Arg1 and NOS. Arg1 activity in myeloid cells has clearly been shown to be immunosuppressive and pro-tumorigenic. First, Arg1-expressing myeloid cells consume arginine from the media and suppress T cell activity in co-culture, and importantly, T cell proliferation can be restored either by supplementing the media with arginine or by the addition of an arginase inhibitor, showing that arginase activity is necessary for the observed immune suppression (FIG. 2A). Secondly, genetic ablation of Arg1 in the myeloid compartment was suggested to reduce inflammation or tumor growth, indicative of a pro-tumorigenic and immune suppressive role for Arg1 in vivo. Thirdly, blocking arginase activity pharmacologically with nor-NOHA or arginase inhibitor reduces tumor growth. The present study additionally demonstrates that Arg1 inhibition with arginase inhibitor raises tumor and plasma arginine and increases inflammation in the TME. Together these data argue that arginase activity is immunosuppressive and provide validation for arginase as a cancer immunotherapy drug target. A second arginase isoform, Arg2 is a constitutively-expressed mitochondrial matrix protein found at low levels in many tissues and at high levels in kidney and intestine. Since Arg2 activity also affects plasma L-arginine levels, Arg2 could be a regulator of immune function. In support of this notion, Arg2 has been reported to promote maternal-fetal immune tolerance.

Pharmacological arginase inhibition has been well-tolerated in several animal studies, including one study involving a rat model of hypertension in which nor-NOHA was injected over a period of 10 weeks, as well as multi-day studies in which mice have been treated with nor-NOHA. It was observed that twice-daily oral dosing of arginase inhibitor was well-tolerated in mice for at least 40 days. Lack of apparent hepatic toxicity may be explained by several observations. First, arginase inhibitor does not readily enter cells, exhibiting $IC_{50}$ values for intracellular arginase in the HepG2 and K562 cell lines that are two orders of magnitude higher than for soluble arginases in cell lysates (Tables 1 and 2). Secondly, the subcellular localization and regulation of urea cycle Arg1 may protect it from pharmacological inhibition. In hepatocytes, urea cycle Arg1 is tightly associated at the mitochondria in a multi-enzyme complex, and studies using semi-permeabilized cells and radiolabeled substrate have demonstrated that tight channeling of product and substrate occurs among successive enzymes of the urea cycle: arginosuccinate synthase, argininosuccinate lyase, and arginase. Thus, hepatic Arg1 may be less accessible to arginase inhibitor compared to cytoplasmic or extracellular arginase in plasma, tumors, and inflamed tissues. The arginase inhibitor was tested for the ability to inhibit arginase in intact primary hepatocytes (Table 2), media containing ornithine, but not arginine, was used, and urea generated under these conditions should require a complete urea cycle. Therefore, this assay may be a measure of the Arg1 activity that is exclusively associated with the urea cycle.

Arginine supplementation has been investigated as a potential therapy for cancer patients and the clinical results suggest that raising arginine levels may be beneficial. In one study of 18 colorectal cancer patients undergoing tumor resection, histopathologic analysis of biopsies revealed that supplementation of arginine prior to surgery resulted in an increase in $CD16^+$ and $CD56^+$ NK cells infiltrating the tumors. In another study of 96 breast cancer patients, a significant increase in pathological response was observed in patients with small tumors receiving arginine compared to placebo. These data indicate that supplemental arginine may have an immune-stimulatory and anti-tumor effect in cancer patients, and suggest that raising systemic arginine by pharmacological arginase inhibition would be similarly beneficial. However, major limitations to therapeutic oral arginine supplementation include severe gastrointestinal distress and extensive metabolism of arginine by the intestinal mucosa. Arginase inhibitor treatment has the potential to both augment and maintain arginine levels in patients thereby avoiding the gastrointestinal distress and arginine oscillations inherent to dietary arginine supplementation.

Antibodies to T cell checkpoint proteins CTLA-4, PD-1, and PD-L1 have resulted in durable clinical responses for some cancer patients, but many patients do not respond, suggesting that overcoming other immunosuppressive mechanisms will be necessary to reactivate anti-tumor immunity in resistant patients. The cellular and molecular basis of resistance to checkpoint blockade is an area of intense investigation. Biomarker studies examining responsive and resistant patients point to a suppressive TME as one possibility to explain resistance. Patients with a higher baseline level of T cells infiltrating the tumor (T cell-inflamed tumors) compared to non-responsive tumors (cold tumors) were more likely to respond to anti-CTLA-4 or anti-PD-1 therapies, and patients resistant to anti-PD-1 therapy had higher baseline levels of tumor-infiltrating MDSCs compared to responders. Furthermore, pre-clinical studies have shown that the depletion of essential extracellular metabolites in the TME, such as glucose and amino acids, can block T cell effector function. Together, these results suggest that immunosuppressive myeloid cells and depletion of essential metabolites may give rise to cold tumors that are resistant to checkpoint blockade and therefore targeting these myeloid cells and metabolic regulatory pathways, in combination with checkpoint antibodies, could restore inflammation and increase patient response rates. In support of this hypothesis, epacadostat, which inhibits the enzyme IDO-1 and prevents depletion of the essential amino acid tryptophan from the TME, is exhibiting striking results in combination with anti-PD-1 therapy in patients with melanoma, lung cancer, RCC, or head and neck carcinoma, arguing that targeting T cell checkpoints and immunosuppression by the TME is an efficacious combination.\

Incorporation by Reference

All publications, patents, patent applications and other documents cited in this application are hereby incorporated by reference in their entireties for all purposes to the same extent as if each individual publication, patent, patent application or other document were individually indicated to be incorporated by reference for all purposes.

In particular, suitable compounds for practicing the invention are described in U.S. Patent Application Publication Nos. 2014/0343019, 2012/0083469, 2014/0371175, 2012/0129806, 2015/0080341, and PCT Application Publication Nos. WO 99/19295, WO 2010/085797, and WO 2012/091757, which are hereby incorporated by reference herein in their entirety.

EQUIVALENTS

While various specific embodiments have been illustrated and described, it will be appreciated that various changes can be made without departing from the spirit and scope of the invention(s).

What is claimed is:

1. A method of treating cancer comprising administering to a cancer patient in need thereof an arginase inhibitor conjointly with an adoptive immunotherapy that is an adoptive cytotoxic T cell immunotherapy or an adoptive natural killer (NK) cell immunotherapy,
    wherein the arginase inhibitor is a compound having the structure selected from:

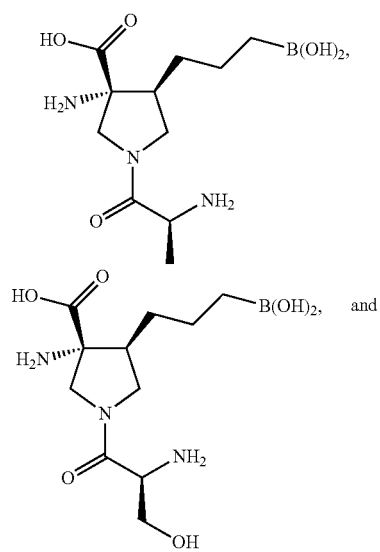

or a pharmaceutically acceptable salt thereof; and
    wherein the patient has a cancer selected from bladder cancer, colorectal cancer, esophageal cancer, gastric cancer, lung cancer, melanoma, breast cancer, mesothelioma, non-small cell lung carcinoma (NSCLC), ovarian cancer, renal cancer, bile duct cancer, multiple myeloma, adrenocortical carcinoma, head and neck cancer, and endometrial cancer.

2. The method of claim 1, wherein the adoptive immunotherapy is an adoptive cytotoxic T cell immunotherapy.

3. The method of claim 2, wherein the adoptive cytotoxic T cell immunotherapy involves transfer of cytotoxic T cells to the patient following stimulation of the cytotoxic T cells.

4. The method of claim 2, wherein the cytotoxic T cells are expanded in the presence of antigen presenting cells (APCs) that present a disease-specific peptide prior to administration to the cancer patient.

5. The method of claim 4, wherein the APCs are B cells.

6. The method of claim 4, wherein the APCs are dendritic cells.

7. The method of claim 1, wherein the adoptive immunotherapy is an adoptive NK cell immunotherapy.

8. The method of claim 1, further comprising administering a PD-1 inhibitor, a PD-L1 inhibitor, or a CTLA-4 inhibitor to the patient.

9. The method of claim 8, further comprising administering a cytokine to the patient.

10. The method of claim 9, wherein the cytokine is IL-2 or IL-5.

11. The method of claim 1, further comprising administering one or more chemotherapeutic agents to the patient, wherein said chemotherapeutic agents are selected from gemcitabine, cyclophosphamide, and fludarabine.

12. The method of claim 11, further comprising administering a cytokine to the patient.

13. The method of claim 12, wherein the cytokine is IL-2 or IL-5.

14. The method of claim 1, further comprising administering an IDO inhibitor to the patient.

15. The method of claim 14, wherein the IDO inhibitor is epacadostat.

16. The method of claim 15, further comprising administering a cytokine to the patient.

17. The method of claim 16, wherein the cytokine is IL-2 or IL-5.

18. The method of claim 1, wherein the patient has melanoma.

19. The method of claim 1, wherein the patient has lung cancer.

20. The method of claim 1, wherein the patient has breast cancer.

21. The method of claim 1, wherein the arginase inhibitor is a compound having the structure:

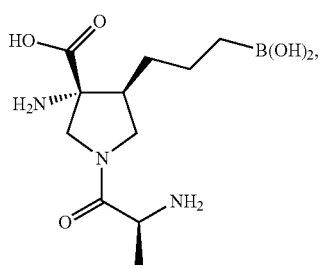 [SMILES: C[C@H](N)C(=O)N1C[C@H](CCCB(O)O)[C@](N)(C(=O)O)C1]

or a pharmaceutically acceptable salt thereof.

22. The method of claim 21, wherein the adoptive immunotherapy is an adoptive cytotoxic T cell immunotherapy.

23. The method of claim 21, wherein the adoptive immunotherapy is an adoptive NK cell immunotherapy.

24. The method of claim 21, further comprising administering a PD-1 inhibitor, a PD-L1 inhibitor, or a CTLA-4 inhibitor to the patient.

25. The method of claim 21, wherein the cancer is selected from lung cancer, melanoma, and breast cancer.

26. The method of claim 1, wherein the arginase inhibitor is a compound having the structure:

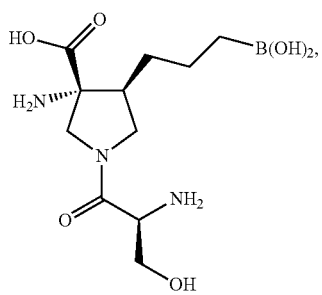 [SMILES: N[C@@H](CO)C(=O)N1C[C@H](CCCB(O)O)[C@](N)(C(=O)O)C1]

or a pharmaceutically acceptable salt thereof.

27. The method of claim 26, wherein the adoptive immunotherapy is an adoptive cytotoxic T cell immunotherapy.

28. The method of claim 26, wherein the adoptive immunotherapy is an adoptive NK cell immunotherapy.

29. The method of claim 26, further comprising administering a PD-1 inhibitor, a PD-L1 inhibitor, or a CTLA-4 inhibitor to the patient.

30. The method of claim 26, wherein the cancer is selected from lung cancer, melanoma, and breast cancer.

31. The method of claim 1, wherein the arginase inhibitor is a compound having the structure:

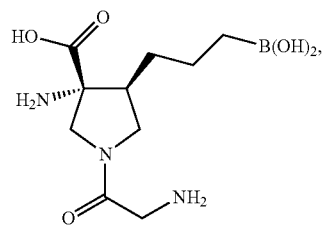 [SMILES: NCC(=O)N1C[C@H](CCCB(O)O)[C@](N)(C(=O)O)C1]

or a pharmaceutically acceptable salt thereof.

32. The method of claim 31, wherein the adoptive immunotherapy is an adoptive cytotoxic T cell immunotherapy.

33. The method of claim 31, wherein the adoptive immunotherapy is an adoptive NK cell immunotherapy.

34. The method of claim 31, further comprising administering a PD-1 inhibitor, a PD-L1 inhibitor, or a CTLA-4 inhibitor to the patient.

35. The method of claim 31, wherein the cancer is selected from lung cancer, melanoma, and breast cancer.

* * * * *